US006867210B2

(12) United States Patent
Hogenkamp et al.

(10) Patent No.: US 6,867,210 B2
(45) Date of Patent: Mar. 15, 2005

(54) ARYL SUBSTITUTED PYRIMIDINES

(75) Inventors: Derk J. Hogenkamp, Carlsbad, CA (US); Phong Nguyen, Placentia, CA (US); Bin Shao, Richboro, PA (US)

(73) Assignee: Euro-Celtique S.A., Luxembourg (LU)

( * ) Notice: Subject to any disclaimer, the term of this patent is extended or adjusted under 35 U.S.C. 154(b) by 0 days.

(21) Appl. No.: 09/803,659

(22) Filed: Mar. 12, 2001

(65) Prior Publication Data

US 2002/0040025 A1 Apr. 4, 2002

Related U.S. Application Data

(60) Provisional application No. 60/188,188, filed on Mar. 10, 2000.

(51) Int. Cl.[7] .................... C07D 239/46; C07D 239/48; A61K 31/505; A61K 31/506; A61P 25/08
(52) U.S. Cl. .................... 514/256; 544/298; 544/315; 544/316; 544/317; 544/319; 544/204; 544/213; 544/217; 544/218; 544/336; 544/408; 514/241; 514/252.1; 514/277; 546/290; 546/296; 546/297
(58) Field of Search ................ 544/298, 315, 544/316, 317, 319; 514/256

(56) References Cited

U.S. PATENT DOCUMENTS

| | | | | |
|---|---|---|---|---|
| 3,149,109 A | * | 9/1964 | Rorig et al. ............. | 260/251 |
| 3,502,673 A | * | 3/1970 | Hepworth et al. ......... | 260/251 |
| 3,631,036 A | * | 12/1971 | Kim et al. .............. | 260/247.2 |
| 3,660,414 A | | 5/1972 | Hardtmann et al. ....... | 260/294.9 |
| 3,709,888 A | | 1/1973 | Hardtmann et al. ....... | 260/256.4 |
| 3,886,167 A | | 5/1975 | Ash et al. .............. | 260/293.52 |
| 3,940,404 A | | 2/1976 | Ash et al. .............. | 260/296 R |
| 4,133,956 A | | 1/1979 | Abdulla et al. .......... | 544/336 |
| 4,293,552 A | | 10/1981 | Miesel ................. | 424/250 |
| 4,332,809 A | | 6/1982 | Honma et al. ........... | 424/266 |
| 4,364,956 A | | 12/1982 | Clark et al. ............ | 424/269 |
| 4,530,842 A | | 7/1985 | Bormann ............... | 514/344 |
| 4,698,091 A | | 10/1987 | Brunner et al. .......... | 71/87 |

(List continued on next page.)

FOREIGN PATENT DOCUMENTS

| | | |
|---|---|---|
| DE | 30 12 597 A1 | 10/1980 |
| DE | 32 39 573 A1 | 5/1983 |
| DE | 32 45 950 A1 | 7/1983 |
| EP | 0 096 657 A2 | 12/1983 |
| EP | 0 123 700 A1 | 11/1984 |
| EP | 0 200 024 B1 | 11/1986 |
| EP | 0 271 195 A1 | 6/1988 |
| EP | 0 362 578 A1 | 4/1990 |
| EP | 0 389 236 A2 | 9/1990 |
| EP | 0 389 236 A3 | 2/1991 |
| EP | 0 428 268 A2 | 5/1991 |
| EP | 0 446 604 A2 | 9/1991 |
| EP | 0 446 604 A3 | 2/1992 |
| EP | 0 480 258 A2 | 4/1992 |

(List continued on next page.)

OTHER PUBLICATIONS

El–Kafrawy et al. J. Chem. Soc. Pak. 14(1) 59–66, 1992.*
Gómez–Parra, V., et a., "New Cardiotonic Agents Related to Amrinone: Synthesis of 1,2–Dihydro–5–arylpyridin–2–ones," *Arch. Pharm (Weinheim)* 325:483–490, VCH Verlagsgesellschaft mbH (1992).
Dialog File 351, Accession No. 3689403, Derwent WPI English language abstract for German Patent Publication No. DE 32 39 573 A1 (Document A07), Derwent Information Ltd. (1983).
Dialog File 351, Accession No. 12589045, Derwent WPI English language abstract for WIPO Publication No. WO 99/31062 A1 (Document AN8), Derwent Information Ltd. (1999).
Dialog File 351, Accession No. 4789463, Derwent WPI English language abstract for European Patent No. EP 0 200 024 B1 (Document AN7).
Chen, C., et al., "A Convenient Synthetic Method for Trisubstituted s–Triazines," *J. Org. Chem.* 60:8428–8430, The American Chemical Society (1995).
Honma, Y., et al., "Antiallergic Agents. 2. N–(1H–Tetrazol–5–yl)–6–phenyl–2–pyridinecarboxamides," *J. Med. Chem.* 26:1499–1504, The American Chemical Society (1983).
Matsumoto, I., "N–Tetrazol–5–yl–6–phenyl–2–pyridinecarboxamides," *Chem. Abstr.* 96:181290v, The American Chemical Society (1982).

(List continued on next page.)

*Primary Examiner*—Richard L. Raymond
*Assistant Examiner*—Venkataraman Balasubramanian
(74) *Attorney, Agent, or Firm*—Sterne, Kessler, Goldstein & Fox P.L.L.C.

(57) ABSTRACT

This invention relates aryl substituted pyridines, pyrimidines, pyrazines and triazines of Formula I:

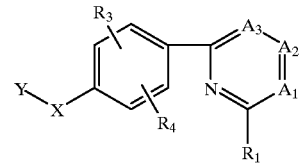

or a pharmaceutically acceptable salt, prodrug or solvate thereof, wherein $A_1$, $A_2$, $A_3$, $R_1$–$R_4$, X and Y are set in the specification. The invention is also directed to the use of compounds of Formula I for the treatment of neuronal damage following global and focal ischemia, for the treatment or prevention of neurodegenerative conditions such as amyotrophic lateral sclerosis (ALS), and for the treatment, prevention or amelioration of both acute or chronic pain, as antitinnitus agents, as anticonvulsants, and as antimanic depressants, as local anesthetics, as antiarrhythmics and for the treatment or prevention of diabetic neuropathy.

57 Claims, 1 Drawing Sheet

U.S. PATENT DOCUMENTS

| | | | | |
|---|---|---|---|---|
| 4,701,208 A | 10/1987 | Los | ................................ | 71/92 |
| 4,912,218 A | 3/1990 | Coyle et al. | ................ | 544/216 |
| 4,920,119 A | 4/1990 | Attwood et al. | ............ | 514/243 |
| 4,968,702 A | 11/1990 | Poletto et al. | ............. | 514/313 |
| 5,084,462 A | 1/1992 | Ackerman et al. | .......... | 514/311 |
| 5,116,989 A | 5/1992 | Hale et al. | ................... | 546/265 |
| 5,250,533 A | 10/1993 | Heinemann et al. | ........ | 514/256 |
| 5,340,701 A | 8/1994 | Desobry | ..................... | 430/325 |
| 5,389,632 A | 2/1995 | Bru-Magniez et al. | ... | 514/233.2 |
| 5,403,934 A | 4/1995 | Batchelor et al. | ........... | 546/290 |
| 5,405,553 A * | 4/1995 | Terada et al. | ............... | 544/298 |
| 5,602,156 A | 2/1997 | Kohn et al. | .................. | 514/359 |
| 5,744,492 A | 4/1998 | Kohn et al. | .................. | 514/359 |
| 6,057,346 A | 5/2000 | Kohn et al. | .................. | 514/359 |
| 6,127,371 A | 10/2000 | Elliott et al. | ........... | 514/252.01 |

FOREIGN PATENT DOCUMENTS

| | | |
|---|---|---|
| EP | 0 480 258 A3 | 9/1992 |
| EP | 0 507 962 A1 | 10/1992 |
| EP | 0 518 798 A2 | 12/1992 |
| EP | 0 550 900 A1 | 7/1993 |
| EP | 0 518 798 A3 | 12/1994 |
| EP | 0 706 795 A2 | 4/1996 |
| EP | 1 052 238 | 11/2000 |
| FR | 1477021 | 4/1967 |
| FR | 1536093 | 9/1967 |
| GB | 2 095 240 A | 9/1982 |
| GB | 2 095 240 A * | 9/1982 |
| JP | 56104883 | 8/1981 |
| JP | 6320234 | 4/1988 |
| JP | 02052360 | 2/1990 |
| JP | 7076542 | 3/1995 |
| WO | WO 92/06085 | 4/1992 |
| WO | WO 95/19358 | 7/1995 |
| WO | WO 96/40628 | 12/1996 |
| WO | WO 98/37068 A1 | 8/1998 |
| WO | WO 98/47869 | 10/1998 |
| WO | WO 99/31062 A1 | 6/1999 |
| WO | WO 99/31088 | 6/1999 |
| WO | WO 99/32468 | 7/1999 |
| WO | WO 99/38829 | 8/1999 |
| WO | WO 00/57877 | 10/2000 |

OTHER PUBLICATIONS

International Search Report for International Patent Application No. PCT/US01/07797, mailed Oct. 9, 2001.

Akopian, A.N., et al., "the tetrodotoxin–resistant sodium channel SNS has a specialized function in pain pathways," *Nat. Neurosci.* 2:541–548, Nature America Inc. (Jun. 1999).

Backonja, M., et al., "Gabapentin for the Symptomatic Treatment of Painful Neuropathy in Patients With Diabetes Mellitus," *J. Am. Med. Assoc.* 280:1831–1836, American Medical Association (1998).

Baker, M.D. and Wood, J.N., "Involvement of $Na^+$ channels in pain pathways," *Trends Pharm. Sci.* 22:27–31, Elsevier Science Ltd. (Jan. 2001).

Bennett, G.J., "Neuropathic Pain: New Insights, New Interventions," *Hosp. Prac.* 33:95–98, 101–104, 107–110, 113–114, The McGraw–Hill Companies (1998).

Bowsher, D., "Neurogenic pain syndromes and their management," *Br. Med. Bull.* 47:644–666, Oxford University Press (1991).

Carver, A.C. and Foley, K.M., "Palliative Care," in: *Cancer Medicine*, Holland, J.F., et al., eds., Williams & Wilkins, Baltimore, Maryland, pp. 992–1000 (1997).

Carver, A.C. and Foley, K.M., "Complications of Cancer and Its Treatment, Management of Cancer Pain," in: *Cancer Medicine*, Holland, J.F., et al., eds., Williams & Wilkins, Baltimore, Maryland, pp. 2204–2223 (1997).

Cavallini, G., et al., "Chemioterapici Antivirali, Nota X—*Mono e bis aldeidi aromatiche,*" *Il Farmaco Ed. Sc.* 19:964–971, Il Farmaco (1964).

Cavallini, G., et al., "Antiviral Compounds. X. Aromatic mono–and dialdehydes," *Chem. Abstracts* 62:Abstract No. 5217h, The American Chemical Society (1965).

Chadda, V.S. and Mathur, M.S., "Double Blind Study of the Effects of Diphenylhydantoin Sodium on Diabetic Neuropathy," *Jr. Asso. Phys. Ind.* 26:403–406, Association of Physician of India (1978).

Clark, M. and Post, R.M., "Carbamazepine, but not caffeine, is highly selective for adenosine $A_1$ binding sites," *Eur. J. Pharmacol.* 164:399–401, Elsevier Science Publishers B.V. (1989).

Collins, S.L., et al., "Antidepressants and Anticonvulsants for Diabetic Neuropathy and Postherpetic Neuralgia: A Quantitative Systematic Review," *J. Pain Symptom Management* 20:449–458, Elsevier (Dec. 2000).

Coward, K., et al., "Plasticity of TTX–sensitive sodium channels PN1 and Brain III in injured human nerves," *Neuroreport* 12:495–500, Lippincott Williams & Wilkins (Mar. 2001).

D'Agostino, V.F., et al., "Absorption Spectra of Tetracyclones. V," *J. Org. Chem.* 23:1539–1544, The American Chemical Society (1958).

Dreixler, J.C., et al., "Block of rat brain recombinant SK channels by tricyclic antidepressants and related compounds," *Eur. J. Pharmacol.* 401:1–7, Elsevier Science B.V. (Jul. 2000).

England, J.D., et al., "Sodium channel accumulation in humans with painful neuromas," *Neurology* 47:272–276, Lippincott–Raven (1996).

Foley, K.M., "Supportive Care and Quality of Life, Management of Cancer Pain," in: *Cancer: Principles & Practice of Oncology*, Fifth Edition, DeVita Jr., V.T., et al., eds. Lippincott–Raven Publishers, Philadelphia, Pennsylvania, pp. 2807–2841 (1997).

Foley, K.M., "Supportive Care and Quality of Life, Management of Cancer Pain," in: *Cancer: Principles & Practice of Oncology*, Sixth Edition, DeVita Jr., V.T., et al., eds. Lippincott–Williams & Wilkins Publishers, Philadelphia, Pennsylvania, pp. 2977–3011 (Jan. 2001).

Grunze, H. et al., "Modulation of Calcium and Potassium Currents by Lamotrigine," *Neuropsychobiology* 38:131–138, S. Karger AG (1998).

Kajander, K.C. and Bennet, G.J., "Onset of a Painful Peripheral Neuropathy in Rat: A Partial and Differential Deafferentation and Spontaneous Discharge in $A\beta$ and $A\delta$ Primary Afferent Neurons," *J. Neurophysiol.* 68:734–744, American Physiological Society (1992).

Keating, M.T. and Sanguinetti, M.C., "Molecular Genetic Insights into Cardiovascular Disease," *Science* 272:681–685, American Association for the Advancement of Science (1996).

Kingery, W.S., "A critical review of controlled clinical trials for peripheral neuropathic pain and complex regional pain syndromes," *Pain* 73:123–139, Elsevier Science B.V. (1997).

Kirsch, G.E., "Na⁺ Channels: Structure, Function, and Classification," *Drug Develop. Res.* 33:263–276, Wiley–Liss, Inc. (1994).

Kuo, C.–C., et al., "Carbamazepine Inhibition of Neuronal Na+ Currents: Quantitative Distinction from Phenytoin and Possible Therapeutic Implications," *Mol. Pharmacol.* 51:1077–1083, American Society for Pharmacology and Experimental Therapeutics (1997).

Lampe, H. and Bigalke, H., "Carbamazepine blocks NMDA–activated currents in cultured spinal cord neurons," *NeuroReport* 1:26–28, Rapid Communications of Oxford Ltd. (1990).

MacFarlane, B.V., et al., "Chronic Neuropathic Pain and Its Control by Drugs," *Pharmacol. Ther.* 75:1–19, Elsevier Science Inc. (1997).

Mackin, G.A., "Medical and Pharmacologic Management of Upper Extremity Neuropathic Pain Syndromes," *J. Hand Ther.* 10:96–109, Hanley & Belfus, Inc. (1997).

Massarani, E. and Mauri, L., "Chemioterapici Antivirali, Nota VIII—*Nuovi gliossali derivati del difeniletere*," *Il Farmaco Ed. Sci.* 19:958–963, Il Farmaco (1964).

Massarani, E. and Mauri, L., "Antiviral Compounds. VIII. New glyoxal derivatives of diphenyl ether," *Chem. Abstracts* 62:Abstract No. 5217e, The American Chemical Society (1965).

McQuay, H.J., et al., "A systematic review of antidepressants in neuropathic pain," *Pain* 68:217–227, Elsevier Science B.V. (1996).

Meadows, H.J., et al., "The neuroprotective agent sipatrigine (BW619C89) potently inhibits the human tandem pore–domain K⁺ channels TREK–1 and TRAAK," *Brain Res.* 892:94–101, Elsevier Science B.V. (Feb. 2001).

Moshé, S.L., "Mechanisms of action of anticonvulsant agents," *Neurology* 55 (*Suppl. 1*):s32–s40, Lippincott Williams & Wilkins (Sep. 2000).

Roden, D.M., "Mechanisms and Management of Proarrhythmia," *Am. J. Cardiol.* 82:49I–57I, Excerpta Medica, Inc. (1998).

Rogawski, M.A. and Porter, R.J., "Antiepileptic Drugs: Pharmacological Mechanisms and Clinical Efficacy with Consideration of Promising Developmental Stage Compounds," *Pharmacol. Rev.* 42:223–286, American Society for Pharmacology and Experimental Therapeutics (1990).

Said, G., "Diabetic neuropathy: an update," *J. Neurol.* 243:431–440, Springer–Verlag (1996).

Saudek, C.D., et al., "Phenytoin in the treatment of diabetic symmetrical polyneuropathy," *Clin. Pharmacol. Ther.* 22:196–199, Mosby Year Book (1997).

Scadding, J.W., "Neuropathic Pain," in: *Diseases of the Nervous System: Clinical Neurobiology*, A.K., et al., eds., W.B. Saunders, Philadelphia, Pennsylvania, pp. 858–872 (1992).

Scadding, J.W., "Peripheral neuropathies," in: *Textbook of Pain. 2ⁿᵈ Edition*, Wall, P.D. and Melzack, R., eds., Churchill Livingstone, Edinburgh, Scotland, pp. 522–534 (1992).

Schirrmacher, K., et al., "Effects of carbamazepine on membrane properties of rat sensory spinal ganglion cells in vitro," *Eur. Neuropsychopharmacol.* 5:501–507, Elsevier Science B.V. (1995).

Seada, M., et al., "Reactions with 2–Amino–3,5–Dicyanopyridines," *Orient. J. Chem.* 5:273–280, Oriental Scientific Publishing Co. (1989).

Sindrup, S.H. and Jensen, T.S., "Pharmacologic treatment of pain in polyneuropathy," *Neurol.* 55:915–920, Lippincott, Williams & Wilkins (Oct. 2000).

Stefani, A., et al., "Lamotrigine inhibits $Ca^{2+}$ currents in cortical neurons: functional implications," *Eur. J. Pharmacol.* 307:113–116, Elsevier Science B.V. (1996).

Taylor, C.P., "Mechanisms of action of gabapentin," *Rev. Neurol.* (*Paris*) 153:1s39–1s45, Masson (1997).

Taylor, C.P., et al., "A summary of mechanistic hypothesis of gabapent in pharmacology," *Epilepsy Res.* 29:233–249, Elsevier Science B.V. (1998).

Veldman, P.H.J.M., et al., "Signs and symptoms of reflex sympathetic dystrophy: prospective study of 829 patients," *The Lancet* 342:1012–1016, The Lancet Publishing Group (1993).

Aggarwal, V., et al., "Reaction of α–Ketoketene S,N–Acetals with Cyanoacetamide: A New General Method for Substituted and Fused 4–(N–Alkylamino–, N–Arylamino–, or N–Morpholino)–3–cyano–2(1H)–pyridones," *Synthesis* 3:214–216, Georg Thieme Verlag (1982).

Al–Omran, F. and Al–Awadi, N., "Studies of Polyfunctionally Substituted Heteroaromatics:Synthesis of New Polyfunctionally Substituted Azabiaryls," *J. Chem. Res. Synop.* 10:392–393, The Royal Society of Chemistry (1995).

Amine, M.S., "Utilities of 4–(4'–Benzyl Phenyl)–6–Arylpyrimidine–2–Thiones for the Synthesis of Biologically Active Condensed and Non–Condensed Heterocycles," *Egypt. J. Chem.* 41:267–276, The National Information and Documentation Centre (1998).

Baldwin, J.E., et al., "Concise Syntheses of Acromelic Acid A and Allo–Acromelic Acid A," *Tetrahedron Lett.* 39:707–710, Pergamon (1998).

Bensimon, G., et al., "A Controlled Trial of Riluzole in Amyotrophic Lateral Sclerosis," *New Eng. J. Med.* 330:585–591, The Massachusetts Medical Society (1994).

Benson, S.C., et al., "Indole as a Dienophile in Inverse Electron Demand Diels–Alder Reactions:Reactions with 1,2,4–Triazines and 1,2–Diazines," *J. Org. Chem.* 55:3257–3269, The American Chemical Society (1990).

Berg, K.E., et al., "Covalently Linked Ruthenium(II)–Manganese(II) Complexes: Distance Dependence of Quenching and Electron Transfer," *Eur. J. Inorg. Chem.* 4:1019–1029, Wiley–VCH Verlag GmbH (2001).

Bettman, B., et al., "Dissociation Constants of Organic Boric Acids," *J. Am. Chem. Soc.* 56:1865–1870, Mack Printing Company (1934).

Brown, C.M., et al., "Neuroprotective properties of lifarizine compared with those of other agents in a mouse model of focal cerebral ischaemia," *Br. J. Pharmacol.* 115:1425–1432, Stockton Press (1995).

Buchan, A.M., et al., "AMPA Antagonists: Do They Hold More Promise for Clinical Stroke Trials Than NMDA Antagonists?" *Suppl. Stroke* 24:I–148–I–152, American Heart Association (1993).

Burdeska, K., et al., "Über die Herstellung von Styryl– und Stilbenyl–Derivaten des Pyrimidins," *Helv. Chim. Acta.* 64:113–152, Schweizerische Chemische Gesellschaft (1981).

Cabrerizo, M., et al., "Sintesis De Heterociclos. III. 2–Amino–3,5–diciano–4–aril–6–alcoxipiridines a partir de bencilidenmalononitrilos," *An. Quim.* 70:951–958, La Real Sociedad Española de Fisica y Química (1974).

Catterall, W.A., "Neurotoxins That Act on Voltage–Sensitive Sodium Channels in Excitable Membranes," *Ann. Rev. Pharmacol. Toxicol 20*:15–43, Annual Reviews Inc. (1980).

Catteral, W.A., "Common modes of drug action on Na+ channels: local anesthetics, antiarrhythmics and anticonvulsants," *Trends Pharmacol. Sci. 8*:57–65, Elsevier Publications Cambridge (1987).

Catteral, W.A., "Structure and Function of Voltage–Sensitive Ion Channels," *Science 242*:50–61, American Association for the Advancement of Science (1988).

Chacóon, M. del C., et al., "Synthèse d'hétérocycles. XX (1). Réaction du malononitrile avec quelques cinnamonitriles," *J. Heterocycle. Chem. 19*:421–423, The Journal of Heterocyclic Chemistry (1982).

Chambers, R.J., et al., "Biarylcarboxamide Inhibitors of Phosphodiesterase IV and Tumor Necrosis Factor–α," *Bioorg. Med. Chem. Lett. 7*:739–744, Pergamon Press (1997).

Creveling, C.R., et al., "Batrachotoxin–Induced Depolorization and [$^3$H]Batrachotoxinin–A 20α–Benzoate Binding in a Vesicular Preparation from Guinea Pig Cerebral Cortex," *Mol. Pharmacol. 23*:350–358, The American Society for Pharmacology and Experimental Therapeutics (1983).

Daines R.A., et al., "Quinine Analogs as Non–Peptide Calcitonin Gene–Related Peptide (CGRP) Receptor Antagonists," *Bioorg. Med. Chem. Lett. 7*:2673–2676, Pergamon Press (1997).

Daves, G.D., et al., "Pyrimidines. XIII. 2– and 6–Substituted 4–Pyrimidinecarboxylic Acids (1a)," *J. Heterocyclic Chem. 1*:130–133, The Journal of Heterocyclic Chemistry (1964).

Denicoff, K.D., et al., "Efficacy of Carbamazepine Compared With Other Agents: A Clinical Practice Survey," *J. Clin. Psychiatry 55*:70–76, Physicians' Postgraduate Press, Inc. (1994).

DeWald, H.A., et al., "Pyrazolodiazepines. 3. 4–Aryl–1,6, 7,8–tetrahydro–1,3–dialkylpyrazolo[3,4–e][1,4]diazepines as Antidepressant Agents," *J. Med. Chem. 24*:982–987, The American Chemical Society (1981).

Domagala, J.M. and Peterson, P., "New 7–Substituted Quinolone Antibacterial Agents. II. The Synthesis of 1–Ethyl–1, 4–dihydro–4–oxo–7–(pyrazolyl, isoxazolyl, and pyrimidinyl)–1,8–naphthyridine and quinolone–3–carboxylic Acids," *J. Heterocyclic Chem. 26*:1147–1158, The Journal of Heterocyclic Chemistry (1989).

Donaldson, I., "Tegretol: A double blind trial in tinnitus," *J. Laryngol. Otol. 95*:947–951, Headley Brothers Ltd. (1981).

El–Kafrawy, A.F., et al., "A Facile One–step Conversion of β–Benzoylacrylic Acids into Some Interesting Heterocycles and Study of their Microbiological Activity," *J. Chem. Soc. Pak. 14*:59–66, (1992).

Fischer, G.W., "Tetrazole Compounds. 8[1]. Synthesis of Tetrazolylpyrimidines from Tetrazolyl–substituted Enamino Ketones," *J. Heterocyclic Chem. 30*:1517–1519, The Journal of Heterocyclic Chemistry (1993).

Fuentes, L., et al., "Sintesis de Heterociclos. XVI Reaccion del Malonitrolo con Bencilidenmalonitrilos en Presencia de Aminas," *An. Quim. Ser. C 76*:68–69, Real Sociedad Española de Fisica y Quimica (1980).

Fuentes, L., et al., "Amalgam (Na.Hg) Reduction of some 4–Substituted–2–amino–3,5–dicyano–6–methoxypyridines. New Evidence Regarding the Oxidation Step in their Synthesis," *J. Heterocycl. Chem. 36*:481–483, The Journal of Heterocyclic Chemistry (Mar./Apr. 1999).

Gainer, H., "Synthesis of Pyrazinoic Acid," *J. Org. Chem. 24*:691, The American Chemical Society (1959).

Giroux, A., et al., "One Pot Biaryl Synthesis via in situ Boronate Formation," *Tetrahedron Lett. 38*:3841–3844, Pergamon Press (1997).

Görlitzer, K. and Düwel, W., "Pyridin–Verbindungen aus Etacrynsäure, 2. Mitteilung," *Arch. Pharm. (Weinheim) 325*:357–359, VCH Verlagsgesellschaft mbH (1992).

Görlitzer, K. and Diers, K., "Pyridine und Pyrimidine aus Etacrynsäure," *Pharmazie 52*:97–100, Eschborn Govi–Verlag Pharmazeutischer Verlag GmbH (1997).

Graham, S.H., et al., "Neuroprotective Effects of a Use–Dependent Blocker of Voltage–Dependent Sodium Channels, BW619C89, in Rat Middle Cerebral Artery Occlusion," *J. Pharmacol. Exp. Ther. 269*:854–859, Williams and Wilkins (1994).

Graham, S.H. et al., "A Dose–Response Study of Neuroprotection Using the AMPA Antagonist NBQX in Rat Focal Cerebral Ischemia," *J. Pharmacol. Exp. Ther. 276*:1–4, Williams and Wilkins (1996).

Hamill, O.P., et al., "Improved Patch–Clamp Techniques for High–Resolution Current Recording from Cells and Cell–Free Membrane Patches," *Pflügers Arch. 391*:85–100, Springer–Verlag (1981).

Hunskaar, S., et al., "Formalin test in mice, a useful technique for evaluating mild analgesics," *J. Neurosci. Methods 14*:69–76, Elsevier Science Publishers B.V. (1985).

Hussain, S.M., et al., "New Synthesis of Polyfunctionally Substituted 2–Mercaptopyridines and Fused Pyridines," *Gazz. Chim. Ital. 124*:97–101, Società Chimica Italiana (1994).

Iwamoto, K., et al., "Ring Transformation of Fused Pyridazines. III. 1–Substituted Phthalazines with Ynamines," *Chem. Pharm. Bull. 43*:679–682, Pharmaceutical Society of Japan (1995).

Iwasaki, Y., et al., "CNQX prevents spinal motor neuron death following sciatic nerve transection in newborn rats," *J. Neuro. Sci. 134*:21–25, Elsevier Science B.V. (1995).

Kagabu, S. and Mizoguchi, S., "A Unique Synthetic Method for Pyridine–Ring Containing Ter–, Quater– and Quinquearyl and Vinylogues by Thermolysis of 2,2–Dichlorocyclopropylmethyleneamines," *Synthesis 3*:372–376, Thieme (1996).

Karamysheva, L.A., et al., "New Heterocyclic Liquid Crystalline Compounds," *Mol. Cryst. Liq. Cryst. 67*:241–251, Gordon and Breach Science Publishers, Inc. (1981).

Katagiri, N., et al., "Cycloadditions in Syntheses. XXXVII. Syntheses of 6–Trifluoromethyl–1,2,4–triazines and –1,2, 4–triazin–5–ones and Their Pericyclic Reactions with Olefins," *Chem. Pharm. Bull. 36*:3354–3372, Pharmaceutical Society of Japan (1988).

Kauffmann, T. and Wolf, D., "Synthese von Amidrazonen aus Nitrilen und Natriumhydrazid," *Angew. Chem. 75*:344, Verlag Chemie GmbH (1963).

Kim, S.H. and Chung, J.M., "An experimental model for peripheral neuropathy produced by segmental spinal nerve ligation in the rat," *Pain 50*:355–363, Elsevier Science Publishers B.V. (1992).

Klauschenz, E., et al., "Potentielle Kardiotonika. 2. Mitteilung: Synthese und pharmakologische Eigenschaften von 5–(pyrid–4–yl)–und 5–phenylsubstituierten 3–Cyan–6–methyl–2–oxaalkylamino–pyridinen" *Pharmazie 44*:23–25, VEB Verlag Volk und Gesundheit (1989).

Konakahara, T., et al., "One–pot synthesis of 2–(trifluoromethyl)pyridines from N–silyl–1–aza–allyl anions with trifluoroacetylketene diethyl ketal or (E)–1,1,1–trifluoro–4–phenylbut–3–en–2–one," *J. Chem. Soc., Perkin Trans. 1*:2803–2806, The Royal Society of Chemistry (Oct. 1999).

Kono, S., et al., "Studies on as–Triazine Derivatives. VI. Introduction of Aryl Groups to the 5–Position of 1,2,4–Triazines," *Heterocycles 23*:2807–2810, Elsevier Science (1985).

Kumar, A., et al., "Keten Dithioacetals. Part 11. Reaction of 3–Cyano–4–methylthio–2(1H)–pyridones with Hydrazine and Guanidine: Synthesis of Novel Substituted and Fused Pyrazolo[4,3–c]pyridone and Pyrido[4,3–d]pyrimidine derivatives," *J. Chem. Soc., Perkin Trans. 1*:857–862, The Royal Society of Chemistry (1978).

Kuo, C.–C. and Bean, B.P., "Slow Binding of Phenytoin to Inactivated Sodium Channels in Rat Hippocampal Neurons," *Mol. Pharmacol. 46*:716–725, Williams and Wilkins (1994).

Latif, N., et al., "Malononitriles & Cyanoesters: Part VI–Synthesis of New Biologically Active Cyanopyridines," *Indian J. Chem. 20B*:147–149, Publications and Information Directorate (1981).

Leff, P. and Dougall, I.G., "Further concerns over Cheng–Prusoff analysis," *TiPS 14*:110–112, Elsevier Science Publishers Ltd. (1993).

Li, J.J., et al., "1,2–Diarylcyclopentenes as Selective Cyclooxygenase–2 Inhibitors and Orally Active Anti–inflammatory Agents," *J. Med. Chem. 38*:4570–4578, The American Chemical Society (1995).

Liao, T.K., et al., "Synthetic Studies of the Antitumor Antibiotic Streptonigrin. II. Synthesis of the C–D Ring Portion of Streptonigrin," *J. Heterocycl. Chem. 13*:1283–1288, The Journal of Heterocyclic Chemistry (1976).

Majumdar, B., et al., "An electrocochleographic study of the effects of lignocaine on patients with tinnitus," *Clin. Otolaryngol 8*:175–180, Blackwell Scientific Publications (1983).

Mano, M., et al., "Anticoccidials. V. Synthesis and Anticoccidial Activity of 2(1H)–Pyrazinone 4–Oxide Derivatives," *Chem. Pharm. Bull. 28*:2734–2747, Pharmaceutical Society of Japan (1980).

Marcoux, J.–F., et al., "A General Copper–Catalyzed Synthesis of Diaryl Ethers," *J. Am. Chem. Soc. 119*:10539–10540, The American Chemical Society (1997).

Møller, A.R., "Similarities Between Chronic Pain and Tinnitus," *Am. J. Otol. 18*:577–585, Lippincott–Raven Publishers (1997).

Murata, M., et al., "Palladium–Catalyzed Borylation of Aryl Halides or Triflates with Dialkoxyborane: A Novel and Facile Synthetic Route to Arylboronates," *J. Org. Chem. 65*:164–168, The American Chemical Society (Dec. 1999/Jan. 2000).

Nezu, Y., et al., "Dimethoxypyrimidines as Novel Herbicides. Part 1. Synthesis and Herbicidal Activity of Dimethoxyphenoxyphenoxypyrimidines and Analogues," *Pestic. Sci. 47*:103–113, John Wiley and Sons Ltd. (1996).

Ohizumi, Y., et al., "Specific Inhibition of [$^3$H] Saxitoxin Binding to Skeletal Muscle Sodium Channels by Geographutoxin II, a Polypeptide Channel Blocker," *J. Biol. Chem. 261*:6149–6152, The American Society of Biological Chemists, Inc. (1986).

Ohta, A., et al., "Reactions of the Monoxides of 2,6–Distributed Pyrazines with Phosphoryl Chloride and Acetic Anhydride," *J. Heterocyclic Chem. 20*:311–320, The Journal of Heterocyclic Chemistry (1983).

Pallas, M., et al., "Chemical synthesis of new pyridine derivatives acting as inhibitors of phosphodiesterase," *Pharm. Pharmacol. Lett. 3*:36–39, Springer–Verlag (1993).

Pavlyuchenko, A.I., et al., "Synthesis and Structure of Mesomorphic 2–cyano–5–[p–alkyl(alkoxy)phenyl]–pyridines," *Chem. Heterocycl. Compounds 16*:681–684, Plenum–Publishing Corporation (1981).

Petrovskii, A.S., et al., "Phosphazoreaction in the Series of 2–Amino–3,5–dicyano–4–aryl–6–methoxypyridines," *Zh. Obshch. Khim. 53*:1187–1188, Nauka (1983).

Piettre, S.R., et al., "Monoaryl– and Bisaryldihydroxytropolones as Potent Inhibitors of Inositol Monophosphatase," *J. Med. Chem. 40*:4208–4221, The American Chemical Society (1997).

Quintela, J.M. and Peinador, C., "A Ready One–pot Preparation for 7–Oxa(or thia)–3,4,6–triazabenz[d,e]anthracene and 7–Oxa–3,4,6,9–tetrabenz[d,e]anthracene Derivatives," *Tetrahedron 52*:10497–10506, Pergamon Press (1996).

Ragsdale, D.S., et al., "Frequency and Voltage–Dependent Inhibition of Type 11A Na+Channels, Expressed in a Mammalian Cell Line, by Local Anesthetic, Antiarryhthmic, and Anticonvulsant Drugs," *Mol. Pharmacol. 40*:756–765, Williams & Wilkins (1991).

Rätz, R. and Schroeder, H., "Products from Reaction of Hydrazine and Thionooxamic Acid and Their Conversion into Heterocyclic Compounds," *J. Org. Chem. 23*:1931–1934, The American Chemical Society (1958).

Reddy, A.C.S., et al., "Fluoro–organics: trifluoromethyl group–induced O–alkylation of pyridin–2–ones," *J. Fluorine Chem. 78*:21–25, Elsevier Science S.A. (1996).

Reddy, A.C.S., et al., "A Novel Method for the Synthesis of Isoxazolo and Pyrazolo Pyridines Using Hypervalent Iodine Reagent," *Synth. Commun. 27*:2217–2222, Marcel Dekker, Inc. (1997).

Rottländer, M. and Knochel, P., "Multiple Cross–Coupling Reactions of Aryl and Benzylic Zinc Halides with Aryl Halides and Triflates in Solid–Phase Synthesis of Polyfunctional Aromatics," *Synlett 9*:1084–1086, Thieme (1997).

Rykowski, A. and Makosza, M., "Reaction of 1,2,4–Triazines with Nitronate Anions, Direct Nucleophilic Acylation of 1,2,4–Triazines," *Tetrahedron Lett. 25*:4795–4796, Pergamon Press Ltd. (1984).

Rykowski, A., et al., "Reactions of 1,2,4–Triazines with Nitromethide Ion. A Convenient Method of Preparation of 1,2,4–Triazin–5–ylcarbaldehyde Oximes and their Synthetic Applications," *J. Heterocycl. Chem. 33*:1567–1571, The Journal of Heterocyclic Chemistry (1996).

Sakamoto, T., et al., "Studies on Pyrimidine Derivatives. XVI. Site Selectivity in the Homolytic Substitution of Simple Pyrimidines," *Chem. Pharm. Bull. 28*:571–577, Pharmaceutical Society of Japan (1980).

Salman, A.S.S., "Synthesis and reaction of cyanopyridone derivatives and their potential biological activities," *Pharmazie 54*:178–183, Eschborn Govi–Verlag Pharmazeutischer Verlag GmbH (Mar. 1999).

Sammour, A., et al., "Some reactions of the 2 (1H)–Pyridones Prepared from 4,4 Dimethoxychalcone and Anisal Acetone," *U.A.R.J. Chem. 14*:581–598, The National Information and Documentation Centre (1971).

Sato, N., et al., "Studies on pyrazines. Part 34. Synthetic approach, stability and tautomerism of 2,6–dihydroxypyrazines," *J. Chem. Soc., Perkin Trans. 1*:3167–3172, The Royal Society of Chemistry (1997).

Satyanarayana, J., "Cyclocondensation of α–Oxoketone N,S–Acetals with β–Lithioamino–β–Substituted Acrylonitriles: A Facile Route to 2,6–Substituted 4–Amino–3–cyanopyridines," *Synthesis 10*:889–890, Georg Thieme Verlag (1991).

Seada, M., et al., "Synthesis and Biological Activities of Some New Pyridazine Derivatives," *J. Chin. Chem. Soc. 36*:241–249, Chinese Chemical Society (1989).

Senga, K., et al., "New Syntheses of Pyrido[3,2–d]pyrimidines," *J. Heterocycl. Chem. 19*:805–808, The Journal of Heterocyclic Chemistry (1982).

Sheardown, M.J., et al., "AMPA, but not NMDA, receptor antagonism is neuroprotective in gerbil global ischaemia, even when delayed 24 h," *Eur. J. Pharmacol. 236*:347–353, Elsevier Science Publishers B.V. (1993).

Shkurko, O.P., et al., "Electronic Spectra of asym–Triazinyl Groups," *Chem. Heterocycl. Compd. 23*:216–221, Plenum Publishing Corporation (1987).

Simpson, J.J. and Davies, W.E., "Recent advances in the pharmacological treatment of tinnitus," *Trends Pharmacol. Sci. 20*:12–18, Elsevier Science London (Jan. 1999).

Singh, G., et al., "Synthesis of nucleosides of pyrido–[2,3–d]pyrimidines and their microbial activity," *Indian J. Chem. 37B*:517–520, National Institute of Science Communication (1998).

Stys, P.K., et al., "Ionic Mechanisms of Anoxic Injury in Mammalian CNS White Matter: Role of $Na^+$ Channels and $Na^+$–$Ca^{2+}$ Exchanger," *J. Neurosci. 12*:430–439, Society for Neuroscience (1992).

Tanaka, A., et al., "Inhibitors of Acyl–CoA:Cholesterol O–Acyltransferase. 3. Discovery of a Novel Series of N–Alkyl–N–[(flurophenoxy)benzyl]–N'–arlyureas with Weak Toxicological Effects on Adrenal Glands," *J. Med. Chem. 41*:4408–4420, The American Chemical Society (1998).

Taylor, C.P. and Meldrum, B.S., "$Na^+$ channels as targets for neuroprotective drugs," *Trends Pharmacol. Sci. 16*:309–316, Elsevier Science Ltd. (1995).

Tonndorf, J., "The analogy between tinnitus and pain: A suggestion for a physiological basis of chronic tinnitus," *Hear Res. 28*:271–275, Elsevier Science Publishers B.V. (1987).

Troschütz, V.R. and Nietsch, K.–H., "Einfache Synthese von 6–Aryl–2–methyl–nicotinsäure–Derivaten," *Chem. Ztg. 114*:321–322, Huethig Publishing Ltd. (1990).

Verndoorn, T.A., et al., "Functional Properties of Recombinant Rat $GABA_A$ Receptors Depend upon Subunit Composition," *Neuron 4*919–928, Cell Press (1990).

Wasfy, A.A.F., et al., "Novel Pyrimidine Congeners as Antimicrobial Agents," *Sulfur Lett. 19*:45–53, Harwood Academic Publishers GmbH (1995).

Wasfy, A.A.F., et al., "Synthesis and Reactions of 6(4)–(P–Benzylphenyl)–4(6)–Phenylpyrimidine–2(1H) Thione," *Heterocycl. Commun. 2*:375–381, Freund Publishing House Ltd. (1996).

Woodward, R.M., et al., "Effects of Steroids on γ–Aminobutyric Acid Receptors Expressed in *Xenopus* Oocytes by Poly(A)$^+$ RNA from Mammalian Brain and Retina," *Mol. Pharmacol. 41*:89–103, Williams and Wilkins (1992).

Wrathall, J.R., et al., "Amelioration of Functional Deficits from Spinal Cord Trauma with Systemically Administered NBQX, an Antagonist of Non–N–methyl–D–aspartate receptors," *Exp. Neurol. 137*:119–126, Academic Press, Inc. (1996).

Petrovskii, A.S., et al., "Phosphazo reaction in a series of 2–amino–3,5–dicyano–4–aryl–6–methoxypyridines," *CAPLUS Accession No. 1983*:505364, Chemical Abstracts Service (1983).

Chemical Abstracts English language abstract of JP 02052360 (Document AM7), *Database CAPLUS Accession No. 1990*:523850, Chemical Abstracts Service (1990).

Seada, M., et al., "Reactions with 2–amino–3,5–dicyanopyridines," *Database CAPLUS Accession No. 114*:81740, Chemical Abstracts Service (1991).

Troschütz, R., et al., "Easy synthesis of 6–aryl–2–methylnicotinic acid derivatives," *Database CAPLUS Accession No. 114*:101664, Chemical Abstracts Service (1991).

Chemical Abstracts English language abstract of EP 0 480 258 A2 (Document AP6), *Database CAPLUS Accession No. 1992*:426351, Chemical Abstracts Service (1992).

Dialog File 351, Accession No. 3212225, Derwent WPI English language abstract for JP 56104883 (Document AN2).

Dialog File 351, Accession No. 3689403, Derwent WPI English language abstract for EP 0 123 700 A1 (Document AO2).

Dialog File 351, Accession No. 3710355, Derwent WPI English language abstract for DE 32 45 950 A1 (Document AL3).

Dialog File 351, Accession No. 3159675, Derwent WPI English Language abstract for JP 6320234 (Document AM3).

Dialog File 351, Accession No. 9527161, Derwent WPI English language abstract for EP 0 550 900 A1 (Document AN4).

Dialog File 351, Accession No. 10250554, Derwent WPI English language abstract for JP 7076542 (Document AO4).

Chemical Abstracts English language abstract of FR 1,477,021 (Document AO5), *Database CAPLUS Accession No. 1967*:521357, Chemical Abstracts Service (1967).

Chemical Abstracts English language abstract of FR 1,536,093 (Document AL2), *Database CAPLUS Accession No. 1969*:481429, Chemical Abstracts Service (1969).

Chemical Abstracts English language abstract of EP 0 480 258 A2 (Document AP6), Database CAPLUS Accession No. 1992:426351, Chemical Abstracts Service (1992).

Dialog File 351, Accession No. 3212225, Derwent WPI English language abstract for JP 56104883 (Document AW2).

Dialog File 351, Accession No. 3689403, Derwent WPI English language abstract for EP 0 123 700 A1 (Document AO2).

* cited by examiner

ARYL SUBSTITUTED PYRIMIDINES

This application claims the priority benefit under 35 U.S.C. §119 of U.S. Provisional application Ser. No. 60/188,188, filed Mar. 10, 2000, the entirety of which is incorporated by reference herein.

BACKGROUND OF THE INVENTION

1. Field of the Invention

This invention is in the field of medicinal chemistry. In particular, the invention relates to novel aryl substituted pyridines, pyrimidines, pyrazines and triazines, and the discovery that these compounds are anticonvulsants and act as blockers of sodium ($Na^+$) channels.

2. Related Art

Several classes of therapeutically useful drugs, including local anesthetics such as lidocaine and bupivacaine, antiarrhythmics such as propafenone and amioclarone, and anticonvulsants such as lamotrigine, phenytoin and carbamazepine, have been shown to share a common mechanism of action by blocking or modulating $Na^+$ channel activity (Catterall, W. A., *Trends Pharmacol. Sci.* 8:57–65 (1987)). Each of these agents is believed to act by interfering with the rapid influx of $Na^+$ ions.

Recently, other $Na^+$ channel blockers such as BW619C89 and lifarizine have been shown to be neuroprotective in animal models of global and focal ischemia and are presently in clinical trials (Graham et al., *J. Pharmacol. Exp. Ther.* 269:854–859 (1994); Brown et al., *British J Pharmacol.* 115:1425–1432 (1995)).

The neuroprotective activity of $Na^+$ channel blockers is due to their effectiveness in decreasing extracellular glutamate concentration during ischemia by inhibiting the release of this excitotoxic amino acid neurotransmitter. Studies have shown that unlike glutamate receptor antagonists, $Na^+$ channel blockers prevent hypoxic damage to mammalian white matter (Stys et al., *J Neurosci.* 12:430–439 (1992)). Thus, they may offer advantages for treating certain types of strokes or neuronal trauma where damage to white matter tracts is prominent.

Another example of clinical use of a $Na^+$ channel blocker is riluzole. This drug has been shown to prolong survival in a subset of patients with ALS (Bensimm et al., *New Engl. J Med.* 330:585–591 (1994)) and has subsequently been approved by the FDA for the treatment of ALS. In addition to the above-mentioned clinical uses, carbamazepine, lidocaine and phenytoin are occasionally used to treat neuropathic pain, such as from trigeminal neurologia, diabetic neuropathy and other forms of nerve damage (Taylor and Meldrum, *Trends Pharmacol. Sci.* 16:309–316 (1995)), and carbamazepine and lamotrigine have been used for the treatment of manic depression (Denicott et al., *J. Clin. Psychiatry* 55: 70–76 (1994)). Furthermore, based on a number of similiarities between chronic pain and tinnitus, (Moller, A. R. *Am. J. Otol.* 18: 577–585 (1997); Tonndorf, *J. Hear. Res.* 28: 271–275 (1987)) it has been proposed that tinnitus should be viewed as a form of chronic pain sensation (Simpson, J. J. and Davies, E. W. *Tip.* 20: 12–18 (1999)). Indeed, lignocaine and carbamazepine have been shown to be efficacious in treating tinnitus (Majumdar, B. et al. *Clin. Otolaryngol.* 8: 175–180 (1983); Donaldson, I. *Laryngol. Otol.* 95: 947–951 (1981)).

It has been established that there are at least five to six sites on the voltage-sensitive $Na^+$ channels which bind neurotoxins specifically (Catterall, W. A., *Science* 242:50–61 (1988)). Studies have further revealed that therapeutic antiarrhythmics, anticonvulsants and local anesthetics whose actions are mediated by $Na^+$ channels, exert their action by interacting with the intracellular side of the $Na^+$ channel and allosterically inhibiting interaction with neurotoxin receptor site 2 (Catterall, W. A., *Ann. Rev. Pharmacol. Toxicol.* 10:15–43 (1980)).

Yukio et al. (*Pestic. Sci.*, 47:103–113 (1996)) disclose a compound of the following Formula:

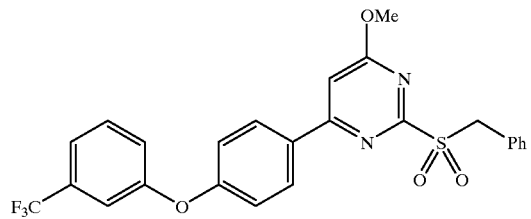

The compounds are disclosed to be useful as herbicides.

FR 1477021 discloses a compound of the following formula:

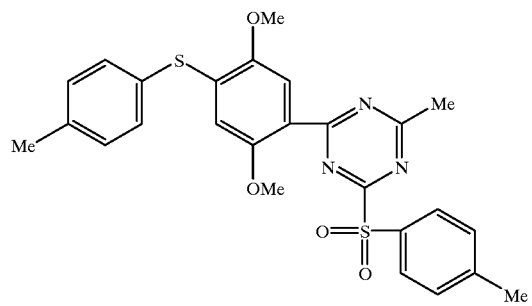

This compound is included in photographic materials.

FR 1536093 discloses a compound of the following formula:

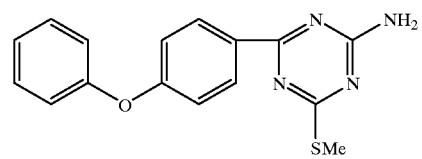

This compound is used as a dye intermediate.

U.S. Pat. No. 4,912,218 discloses a compound of the formula:

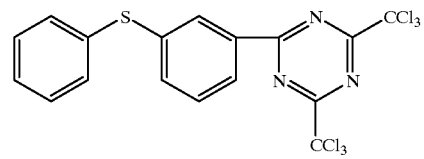

This compound is used for photopolymerizable compositions.

WO 9931088 discloses compounds of the formula:

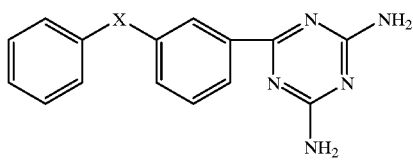

wherein X is O or S. These compounds are stated to be useful as angiogenesis inhibitors.

SUMMARY OF THE INVENTION

The present invention is related to the discovery that aryl substituted pyridines, pyrimidines, pyrazines and triazines represented by Formula I are anticonvulsants and act as blockers of sodium ($Na^+$) channels.

The invention is also related with treating a disorder responsive to the blockade of sodium channels in a mammal suffering from excess activity of said channels by administering an effective amount of a compound of Formula I as described herein.

The present invention is also directed to the use of a compound of Formula I for the treatment of neuronal damage following global and focal ischemia, and for the treatment or prevention of neurodegenerative conditions such as amyotrophic lateral sclerosis (ALS), for the treatment of tinnitus, as antimanic depressants, as local anesthetics, as antiarrhythmics, as anticonvulsants and for the treatment or prevention of diabetic neuropathy and for the treatment of pain including both acute and chronic pain and migraine headache.

A number of compounds useful in the present invention have not been heretofor reported. Thus, one aspect of the present invention is directed to the novel aryl substituted pyridines, pyrimidines, pyrazines and triazines of Formula I.

Another aspect of the present invention is directed to the novel compounds of Formula I as blockers of sodium channels.

A further aspect of the present invention is to provide a method for treating, preventing or ameliorating neuronal loss following global and focal ischemia; treating, preventing or ameliorating pain including acute and chronic pain, and neuropathic pain; treating, preventing or ameliorating convulsion and neurodegenerative conditions; treating, preventing or ameliorating manic depression; using as local anesthesics and anti-arrhythmics, and treating tinnitus by administering a compound of Formula I to a mammal in need of such treatment or use.

Also, an aspect of the present invention is to provide a pharmaceutical composition useful for treating disorders responsive to the blockade of sodium ion channels, containing an effective amount of a compound of Formula I in a mixture with one or more pharmaceutically acceptable carriers or diluents.

Additional embodiments and advantages of the invention will be set forth in part in the description that follows, and in part will be obvious from the description, or may be learned by practice of the invention. The embodiments and advantages of the invention will be realized and attained by means of the elements and combinations particularly pointed out in the appended claims.

It is to be understood that both the foregoing general description and the following detailed description are exemplary and explanatory only and are not restrictive of the invention, as claimed.

BRIEF DESCRIPTION OF THE DRAWINGS

FIG. 1A: IV-curves, FIG. 1C: steady-state inactivation, FIG. 1B: repriming kinetics, and FIG. 1D: time course of binding.

DETAILED DESCRIPTION OF THE INVENTION

Figure 1A:
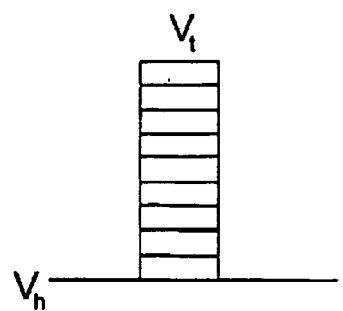
FIGS. 1A, 1B, 1C, and 1D are voltage pulse protocols used to assess the potency and kinetics of inhibition of the $Na^+$ channels by the compounds as follows.

The present invention arises out of the discovery that aryl substituted pyridines, pyrimidines, pyrazines and triazines of Formula I are anticonvulsants and act as blockers of $Na^+$ channels. In view of this discovery compounds of Formula I are useful for treating disorders responsive to the blockade of sodium ion channels.

The compounds useful in this aspect of the present invention are aryl substituted pyridines, pyrimidines, pyrazines and triazines represented by Formula I:

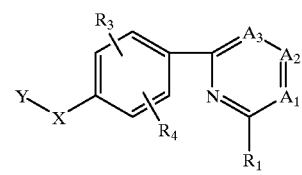

I or a pharmaceutically acceptable salt, prodrug or solvate thereof, wherein:

Y is

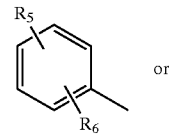

or $R_7$;

provided that when Y is $R_7$, $R_1$ is aminocarbonyl;

$A_1$, $A_2$ and $A_3$ are independently $CR_2$ or N, provided that A1, $A_2$ and $A_3$ are not all N at the same time;

$R_1$ is selected from the group consisting of an optionally substituted alkyl, amino, alkylthiol, $C(O)R_8$, $SO_2R_8$, $OC(O)NH_2$, 2-imidazolinyl, 2-imidazolyl, 3-pyrazolyl, 5-isoxazolyl, and 3-(1,2,4)-triazolyl;

each $R_2$ is independently selected from the group consisting of hydrogen, an optionally substituted alkyl, such as aminoalkyl, haloalkyl and hydroxyalkyl, alkenyl or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino; or $R_1$ and $R_2$ are taken together with the carbon atoms to which they are attached to form a heterocyclic ring;

$R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, carbonylamido and alkylthiol; and $R_7$ is an optionally substituted alkyl;

$R_8$ is selected from the group consisting of alkyl, alkenyl, alkynyl, $OR_9$, amino, alkylamino, dialkylamino, alkenylamino, dialkylaminoalkenyl, dialkylaminoalkylamino, dialkylaminoalkenylamino, alkylaminoalkenylamino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted, provided that $R_8$ is not $OR_9$ when $R_1$ is $SO_2R_8$; wherein $R_9$ is selected from the group consisting of hydrogen, optionally substituted alkyl, and an alkali metal; and X is one of O, S, NH, or $CH_2$ when Y is other than $R_7$; or X is one of O, S, NH, $CH_2$ or absent when Y is $R_7$.

Accordingly, compounds useful in the present invention are aryl substituted pyridines, pyrimidines, pyrazines and triazines represented by Formula II:

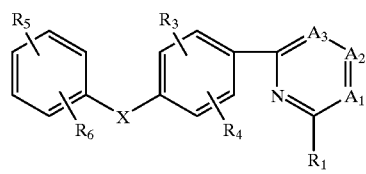

II or a pharmaceutically acceptable salt, prodrug or solvate thereof, wherein:

$A_1$, $A_2$ and $A_3$ are independently $CR_2$ or N, provided that $A_1$, $A_2$ and $A_3$ are not all N at the same time;

$R_1$ is selected from the group consisting of an optionally substituted alkyl, amino, alkylthiol, $C(O)R_8$, $SO_2R_8$, $OC(O)NH_2$, 2-imidazolinyl, 2-imidazolyl, 3-pyrazolyl, 5-isoxazolyl, and 3-(1,2,4)-triazolyl;

each $R_2$ is independently selected from the group consisting of hydrogen, an optionally substituted alkyl, such as aminoalkyl, haloalkyl and hydroxyalkyl, alkenyl or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino; or $R_1$ and $R_2$ are taken together with the carbon atoms to which they are attached to form a heterocyclic ring;

$R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, carbonylamido and alkylthiol;

$R_8$ is selected from the group consisting of alkyl, alkenyl, alkynyl, $OR_9$, amino, alkylamino, dialkylamino, alkenylamino, dialkylaminoalkenyl, dialkylaminoalkylamino, dialkylaminoalkenylamino, alkylaminoalkenylamino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted, provided that $R_8$ is not $OR_9$ when $R_1$ is $SO_2R_8$; wherein $R_9$ is selected from the group consisting of hydrogen, optionally substituted alkyl, and an alkali metal; and X is one of O, S, NH, or $CH_2$.

Another group of compounds useful in this aspect of the present invention are aryl substituted pyridines, pyrimidines, pyrazines and triazines represented by the general Formula II, wherein $A_1$, $A_2$, $A_3$, $R_1$–$R_6$ and $R_8$–$R_{11}$ are as described above, with the provisos that 1) $R_2$ is not methoxy if $R_5$ is trifluoromethyl, $R_6$ is H, X is O and $R_1$ is $SO_2CH_2Ph$;

2) $R_2$ is not $NH_2$ if $R_1$ is methylthio, X is O and two of $A_1$, $A_2$ and $A_3$ are N;

3) $R_2$ is not methyl if $R_1$ is $SO_2R_8$, wherein $R_8$ is methylphenyl, $R_3$ and $R_4$ are methoxy, X is S and two of $A_1$, $A_2$ and $A_3$ are N;

4) $R_2$ is not $CCl_3$ if $R_1$ is $CCl_3$, X is S and two of $A_1$, $A_2$ and $A_3$ are N; or 5) $R_1$ and $R_2$ are not both $NH_2$ if X is O or S and two of $A_1$, $A_2$ and $A_3$ are N.

Examples of bridges formed by $R_1$ and $R_2$ taken together are —$CH_2NCH_2$—, —$C(O)NC(O)$— and —$C(NH_2)$=NH—CH=CH—.

Preferably, $A_1$, $A_2$ and $A_3$ are each $CR_2$ (pyridyl); or A1 is N and $A_2$ and $A_3$ are $CR_2$ (pyrimidinyl); or $A_3$ is N and $A_1$ and $A_2$ are $CR_2$ (pyrimidyl); or $A_2$ is N and $A_1$ and $A_3$ are $CR_2$ (pyrazinyl); or $A_1$ and $A_3$ are N and $A_2$ is $CR_2$ (1,3,5-triazinyl). More preferably, $A_1$, $A_2$ and $A_3$ are each $CR_2$ (pyridyl); or $A_1$ is N and $A_2$ and $A_3$ are $CR_2$ (pyrimidinyl); or $A_3$ is N and $A_1$ and $A_2$ are $CR_2$ (pyrimidyl); or $A_2$ is N and $A_1$ and $A_3$ are $CR_2$ (pyrazinyl). Most preferably, $A_1$, $A_2$ and $A_3$ are each $CR_2$ (pyridyl); or $A_1$ is N and $A_2$ and $A_3$ are $CR_2$ (pyrimidinyl); or $A_3$ is N and $A_1$ and $A_2$ are $CR_2$ (pyrimidyl).

Preferably, $R_1$ is selected from the group consisting of an alkyl optionally substituted by halogen or hydroxy, thiomethyl, $C(O)R_8$, $SO_2R_8$, 2-imidazolinyl, 2-imidazolyl, 3-pyrazolyl, and 5-isoxazolyl, wherein $R_8$ is selected from the group consisting of alkyl, alkenyl, $OR_9$, amino, alkylamino, dialkylamino, alkenylamino, dialkylaminoalkenyl, dialkylaminoalkylamino, and heterocycloalkylamino, all of which can be optionally substituted, provided that $R_8$ is not $OR_9$ when $R_1$ is $SO_2R_8$.

Preferably, $R_2$ is selected from the group consisting of hydrogen, alkyl, alkenyl, alkynyl, aminoalkyl, amino, hydroxyalkyl, alkoxy, aminocarbonyl, alkylaminocarbonyl, arylaminocarbonyl, aralkylaminocarbonyl, alkylcarbonylamino, arylcarbonylamino, and aralkylcarbonylamino, more preferably hydrogen, alkyl, alkoxy, aminoalkyl and aminocarbonyl.

Preferably, $R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, and cyano. More preferably, $R_3$, $R_4$, $R_5$ and $R_6$ are independently selected from the group consisting of hydrogen, alkyl, halogen, haloalkyl, and nitro. Preferred values of $R_3$–$R_6$ include hydrogen, halo, $C_1$–$C_6$ haloalkyl, $C_1$–$C_6$ alkyl, $C_2$–$C_6$ alkenyl, $C_2$–$C_6$ alkynyl, $C_1$–$C_6$ hydroxyalkyl, nitro, amino, ureido, cyano, $C_1$–$C_6$ acylamido, hydroxy, thiol, $C_1$–$C_6$ acyloxy, azido, $C_1$–$C_6$ alkoxy, or carboxy. The groups $R_3$–$R_6$ each take the place of a hydrogen atom that would otherwise be present in any position on the aryl ring to which the R group is attached. Especially preferred are compounds where $R_3$ and $R_4$ are both hydrogen, $R_6$ is hydrogen and $R_5$ is a fluoro in the para-position.

Preferably, $R_7$ is a straight or a branched alkyl group of $C_{1-10}$ carbon atoms, more preferably $C_{1-6}$ carbon atoms, optionally substituted with one or more of halogen, hydroxy, nitro, amino, cyano, and alkoxy.

Preferably, $R_8$ is selected from the group consisting of alkyl, alkenyl, $OR_9$, amino, alkylamino, dialkylamino, alkenylamino, dialkylaminoalkenyl, dialkylaminoalkylamino, and heterocycloalkylamino, all of which can be optionally substituted, wherein $R_9$ is as defined above, provided that $R_8$ is not $OR_9$ when $R_1$ is $SO_2R_8$.

Preferably X is O or S, more preferably X is O.

When X is $CH_2$, $R_1$ is preferably aminocarbonyl.

When $A_1$, $A_2$ and $A_3$ are each $CR_2$ and one $R_2$ is other than H, said $R_2$ is preferably in the position of $A_2$. When $A_1$ is N, $A_2$ and $A_3$ both are $CR_2$ and one $R_2$ is other than H, said $R_2$ is preferably in the position of $A_2$. When $A_3$ is N, $A_1$ and $A_2$ both are $CR_2$ and one $R_2$ is other than H, said $R_2$ is preferably in the position of $A_2$. When $A_2$ is N, $A_1$ and $A_3$ both are $CR_2$ and one $R_2$ is other than H, said $R_2$ is preferably in the position of $A_1$.

In one aspect of the invention, preferred compounds falling within the scope of Formula II include compounds wherein X is O or S. In this aspect of the invention $R_1$ is preferably aminocarbonyl, and $R_2$ is preferably hydrogen.

Preferred $R_3$–$R_6$ groups are as described above.

Since the compounds of Formula I are blockers of sodium ($Na^+$) channels, a number of diseases and conditions mediated by sodium ion influx can be treated employing these compounds. Therefore, the invention is related to a method of treating, preventing or ameliorating neuronal loss associated with stroke, global and focal ischemia, CNS trauma, hypoglycemia and surgery, spinal cord trauma; as well as treating or ameliorating neurodegenerative diseases including Alzheimer's disease, amyotrophic lateral sclerosis, Parkinson's disease, treating or ameliorating anxiety, convulsions, glaucoma, migraine headache, and muscle spasm. The compounds of Formula I are also useful as antitinnitus agents, antimanic depressants, as local anesthetics, and as antiarrhythmics; as well as for treating, preventing or ameliorating pain including surgical, chronic and neuropathic pain. In each instance, the methods of the present invention require administering to an animal in need of such treatment an effective amount of a sodium channel blocker of the present invention, or a pharmaceutically acceptable salt or prodrug thereof.

The invention also relates to aryl-substituted pyridines, pyrimidines, pyrazines and triazines represented by Formula III:

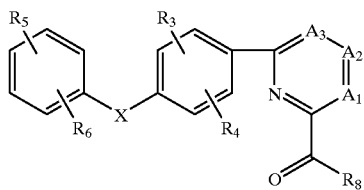

III or a pharmaceutically acceptable salt, prodrug or solvate thereof, wherein:

$A_1$–$A_3$, $R_2$–$R_6$, $R_8$ and X are defined previously with respect to Formulae I-II.

Preferred compounds falling within the scope of Formula III include compounds wherein $R_2$ is hydrogen, $R_8$ is amino, and X is O and S. $R_3$ through $R_6$ have preferred values as described above for Formula II. Further, preferably $R_8$ is selected from the group consisting of alkyl, alkenyl, amino, alkylamino, dialkylamino, alkenylamino, dialkylaminoalkenyl, dialkylaminoalkylamino, and heterocycloalkylamino, all of which can be optionally substituted.

Further, the invention relates to aryl-substituted pyridines, pyrimidines, pyrazines and triazines represented by Formula IV:

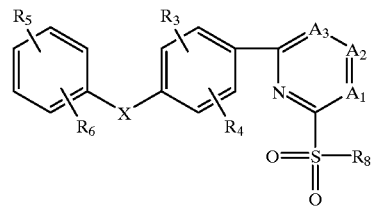

IV or a pharmaceutically acceptable salt, prodrug or solvate thereof, wherein:

$A_1$–$A_3$, $R_2$–$R_6$, and X are defined previously with respect to Formulae I-III and $R_8$ is selected from the group consisting of alkyl, alkenyl, alkynyl, amino, alkylamino, dialkylamino, alkenylamino, dialkylaminoalkenyl, dialkylaminoalkylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted. Preferably, $R_8$ is selected from the group consisting of alkyl, alkenyl, amino, alkylamino, dialkylamino, alkenylamino, dialkylaminoalkenyl, dialkylaminoalkylamino, and heterocycloalkylamino, all of which can be optionally substituted. More preferably, $R_8$ is selected from the group consisting of optionally substituted alkyl, cycloalkyl, aryl and amino. $R_3$ through $R_6$ have preferred values as described above for Formula III Preferred compounds falling within the scope of Formula IV include compounds wherein $R_2$ is hydrogen, $R_8$ is amino, and X is O and S.

Also, the present invention relates to compounds of Formula V:

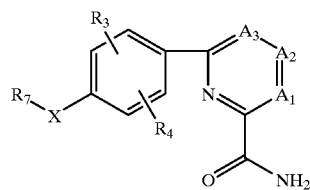

V or a pharmaceutically acceptable salt, prodrug or solvate thereof, wherein:

$A_1$–$A_3$, $R_2$–$R_4$, and $R_7$ are defined previously with respect to Formula I-IV, and X is one of O, S, NH, $CH_2$ or absent.

Preferred compounds falling within the scope of Formulae V include compounds wherein $R_2$ is hydrogen, and X is O and S. Preferably, $R_7$ is a straight or branched chain C, more preferably $C_{1-4}$ alkyl, optionally substituted with one or more of halogen, especially fluoro or chloro. $R_3$ and $R_4$ have preferred values as described above for Formula II.

Exemplary preferred compounds that may be employed in this method of invention include, without limitation:

4-[4-(4-fluorophenoxy)phenyl]pyrimidine-2-carboxamide;
4-[4-(4-nitrophenoxy)phenyl]pyrimidine-2-carboxamide;
4-[4-(4-methoxyphenoxy)phenyl]pyrimidine-2-carboxamide;
4-[4-(4-trifluoromethylphenoxy)phenyl]pyrimidine-2-carboxamide;
4-[4-(3-chloro-2-cyanophenoxy)phenyl]pyrimidine-2-carboxamide;
4-[4-(4-chloro-2-fluorophenoxy)phenyl]pyrimidine-2-carboxamide;

4-[4-(2,4-difluorophenoxy)phenyl]pyrimidine-2-carboxamide;
4-[4-(2-chloro-4-fluorophenoxy)phenyl]pyrimidine-2-carboxamide;
1-[4-[4-(4-fluorophenoxy)phenyl]pyrimidine-2-yl]-ethanone;
2-[4-(4-fluorophenoxy)phenyl]pyrimidine-4-carboxamide;
2-[4-(4-fluorophenoxy)phenyl]-4-methylpyrimidine;
2-methyl-4-[4-(4-fluorophenoxy)phenyl]pyrimidine;
4-[4-(4-fluorophenoxy)phenyl]pyrimidine-2-carboxylic acid;
4-[4-(4-fluorophenoxy)phenyl]pyrimidine-2-carboxylic acid sodium salt;
4-[4-(4-fluorophenoxy)phenyl]pyrimidine-2-carboxylic acid methylamide;
4-[4-(4-fluorophenoxy)phenyl]pyrimidine-2-carboxylic acid dimethylamide;
4-[4-(4-fluorophenoxy)phenyl]pyrimidine-2-carboxylic acid tert-butylamide;
2-[4-(4-chloro-2-fluorophenoxy)phenyl]pyrimidine-4-carboxamide;
2-[4-(4-chloro-2-fluorophenoxy)phenyl]pyrimidine-4-carboxylic acid;
2-(4-phenoxyphenyl)-6-(dimethylamino)pyrimidine-4-carboxylic acid dimethylamide;
4-[4-(4-fluorophenoxy)phenyl]pyrimidine-2-carboxylic acid 2-hydroxyethylamide;
4-[4-(4-fluorophenoxy)phenyl]pyrimidine-2-carboxylic acid hydroxymethyleneamide;
2-(2-hydroxyprop-2-yl)-4-[4-(4-fluorophenoxy)phenyl]pyrimidine;
4-[4-(2,4-difluorophenoxy)phenyl]pyrimidine-2-carboxylic acid 2-morpholin-4-yl-ethyl amide;
2-(4,5-dihydro-1H-imidazol-2-yl)-4-[4-(4-fluorophenoxy)phenyl]-pyrimidine hydrochloride salt;
2-(3-pyrazolyl)-4-[4-(4-fluorophenoxy)phenyl]pyrimidine;
2-(5-isoxazolyl)-4-[4-(4-fluorophenoxy)phenyl]pyrimidine;
2-(1-methyl-3-pyrazolyl)-4-[4-(4-fluorophenoxy)phenyl]pyrimidine;
2-[4-(4-chloro-2-fluorophenoxy)phenyl]pyrimidine-4-carboxylic acid methylamide;
3-dimethylamino-1-{4-[4-(4-fluorophenoxy)phenyl}pyrimidin-2-yl]propenone;
2-thiomethyl-4-[4-(4-fluorophenoxy)phenyl]pyrimidine;
2-methanesulfonyl-4-[4-(4-fluorophenoxy)phenyl]pyrimidine;
2-[4-(4-chloro-2-fluorophenoxy)phenyl]-4-methyl-pyrimidine;
4-[4-(4-fluorophenoxy)-3-fluorophenyl]pyrimidine-2-carboxamide; and
2-[4-(4-fluorophenoxy)-3-fluorophenyl]pyrimidine-4-carboxamide.

Additional useful compounds of the present invention include:
2-methyl-6-(4-phenoxyphenyl)pyridine;
6-(4-phenoxyphenyl)pyridine-2-carboxamide;
2-methyl-6-[4-(4-fluorophenoxy)phenyl]pyridine;
6-(4-phenoxyphenyl)pyridine-2-carboxylic acid;
6-(4-phenoxyphenyl)pyridine-2-carboxylic acid methylamide;
6-[4-(4-fluorophenoxy)phenyl]pyridine-2-carboxamide;
6-[(4-trifluoromethoxy)phenyl]pyridine-2-carboxamide;
6-[4-(2,4-difluorophenoxy)phenyl]pyridine-2-carboxamide;
6-[4-(4-chloro-2-fluorophenoxy)phenyl]pyridine-2-carboxamide;
6-[4-(4-fluorophenoxy)-3-fluorophenyl]pyridine-2-carboxamide;
6-[4-(4-trifluoromethylphenoxy)phenyl]pyridine-2-carboxamide;
6-(4-phenoxyphenyl)pyrazine-2-carboxamide;
3,5-diamino-6-(4-phenoxyphenyl)pyrazine-2-carboxamide; and
2-[4-(4-nitrophenoxy)phenyl]-4-methyl-[1,3,5]-triazine.

Further useful compounds of the invention include:
6-[4-(4-fluorophenoxy)phenyl]pyridine carboxylic acid N-piperidinylethylamide;
6-(4-tert-butylphenyl)pyridine-2-carboxamide;
6-(4-n-butylphenyl)pyridine-2-carboxamide;
6-(4-i-propylphenyl)pyridine-2-carboxamide;
6-(4-thiomethylphenyl)pyridine-2-carboxamide;
6-(4-ethoxyphenyl)pyridine-2-carboxamide; and
6-(4-methoxyphenyl)pyridine-2-carboxamide.

Furthermore, useful compounds of the invention include:
2-dimethylamino-4-[4-(4-fluorophenoxy)phenyl]pyrimidine;
4-[4-(4-fluorophenoxy)phenyl]pyrimidine-2-carboxylic acid ethyl ester;
4-[4-(4-fluorophenoxy)phenyl]pyrimidine-2-carbamate;
4-[4-(4-fluorophenoxy)phenyl]pyrimidine-2-carboxylic acid 2-chloroethylamide;
1-[4-[4-(4-fluorophenoxy)phenyl]pyrimidine-2-yl]-2,2-dibromoethanone;
4-[4-(4-fluorophenoxy)phenyl]pyrimidine-2-carboxylic acid methylaminomethyleneamide hydrochloride;
2-[3-(1,2,4-triazolyl)]-4-[4-(4-fluorophenoxy)phenyl]pyrimidine;
2-[4-(4-chloro-2-fluorophenoxy)phenyl]pyrimidine-4-carboxylic acid dimethylaminomethyleneamide;
4-[4-(2,4-difluorophenoxy)phenyl]pyrimidine-2-carboxylic acid methyl ester;
2-[4-(4-fluorophenoxy)phenyl]pyrimidine-4-carboxylic acid methyl ester;
2-[4-(4-fluorophenoxy)phenyl]-4-[3-(1,2,4-triazolyl)]pyrimidine;
4-[4-(4-fluorophenoxy)phenyl]pyrimidine-2-carboxylic acid hydroxymethyleneamide;
2-(4-phenoxyphenyl)-6-(dimethylamino)pyrimidine-4-carboxamide;
2-(4-phenoxyphenyl)-6-(dimethylamino)pyrimidine-4-carboxylic acid dimethylamide;
2-methyl-3-cyano-6-[4-(4-fluorophenoxy)phenyl]pyridine;
6-[4-(4-fluorophenoxy)phenyl]pyridine-2,3-dicarboxamide;
2-methyl-6-[4-(4-fluorophenoxy)phenyl]pyridine-3-carboxamide;
6-(4-phenoxyphenyl)pyridine-2-carboxylic acid dimethylamide;
5-cyano-6-(4-phenoxyphenyl)pyridine-2-carboxamide;
5-hydroxy-6-(4-phenoxyphenyl)pyridine-2-carboxamide; and
5-methoxy-6-(4-phenoxyphenyl)pyridine-2-carboxamide.

Useful aryl groups are $C_{6-14}$ aryl, especially $C_{6-10}$ aryl. Typical $C_{6-14}$ aryl groups include phenyl, naphthyl, phenanthryl, anthracyl, indenyl, azulenyl, biphenyl, biphenylenyl and fluorenyl groups.

Useful cycloalkyl groups are $C_{3-8}$ cycloalkyl. Typical cycloalkyl groups include cyclopropyl, cyclobutyl, cyclopentyl, cyclohexyl and cycloheptyl.

Useful halo or halogen groups include fluorine, chlorine, bromine and iodine.

Useful alkyl groups include straight-chained and branched $C_{1-10}$ alkyl groups, more preferably $C_{1-6}$ alkyl groups. Typical $C_{1-10}$ alkyl groups include methyl, ethyl, propyl, isopropyl, butyl, sec-butyl, tert-butyl, 3-pentyl, hexyl and octyl groups. Also contemplated is a trimethylene group substituted on two adjoining positions on the benzene ring of the compounds of the invention.

Useful alkenyl groups are $C_{2-6}$ alkenyl groups, preferably $C_{2-4}$ alkenyl. Typical $C_{2-4}$ alkenyl groups include ethenyl, propenyl, isopropenyl, butenyl, and sec-butenyl.

Useful alkynyl groups are $C_{2-6}$ alkynyl groups, preferably $C_{2-4}$ alkynyl. Typical $C_{2-4}$ alkynyl groups include ethynyl, propynyl, butynyl, and 2-butynyl groups.

Useful arylalkyl groups include any of the above-mentioned $C_{1-10}$ alkyl groups substituted by any of the above-mentioned $C_{6-14}$ aryl groups. Useful values include benzyl, phenethyl and naphthylmethyl.

Useful arylalkenyl groups include any of the above-mentioned $C_{2-4}$ alkenyl groups substituted by any of the above-mentioned $C_{6-14}$ aryl groups.

Useful arylalkynyl groups include any of the above-mentioned $C_{2-4}$ alkynyl groups substituted by any of the above-mentioned $C_{6-14}$ aryl groups. Useful values include phenylethynyl and phenylpropynyl.

Useful cycloalkylalkyl groups include any of the above-mentioned $C_{1-10}$ alkyl groups substituted by any of the above-mentioned cycloalkyl groups.

Useful haloalkyl groups include $C_{1-10}$ alkyl groups substituted by one or more fluorine, chlorine, bromine or iodine atoms, e.g. fluoromethyl, difluoromethyl, trifluoromethyl, pentafluoroethyl, 1,1-difluoroethyl and trichloromethyl groups.

Useful hydroxyalkyl groups include $C_{1-10}$ alkyl groups substituted by hydroxy, e.g. hydroxymethyl, hydroxyethyl, hydroxypropyl and hydroxybutyl groups.

Useful alkoxy groups include oxygen substituted by one of the $C_{1-10}$ alkyl groups mentioned above.

Useful alkylthio groups include sulfur substituted by one of the $C_{1-10}$ alkyl groups mentioned above.

Useful acylamino groups are any acyl group, particularly $C_{2-6}$ alkanoyl or $C_{6-10}$ aryl($C_{2-6}$)alkanoyl attached to an amino nitrogen, e.g. acetamido, propionamido, butanoylamido, pentanoylamido, hexanoylamido, and benzoyl.

Useful acyloxy groups are any $C_{1-6}$ acyl (alkanoyl) attached to an oxy (—O—) group, e.g. acetoxy, propionoyloxy, butanoyloxy, pentanoyloxy, hexanoyloxy and the like.

The term heterocyclic is used herein to mean saturated or wholly or partially unsaturated 3–7 membered monocyclic, or 7–10 membered bicyclic ring system, which consists of carbon atoms and from one to four heteroatoms independently selected from the group consisting of O, N, and S, wherein the nitrogen and sulfur heteroatoms can be optionally oxidized, the nitrogen can be optionally quaternized, and including any bicyclic group in which any of the above-defined heterocyclic rings is fused to a benzene ring, and wherein the heterocyclic ring can be substituted on carbon or on a nitrogen atom if the resulting compound is stable. Examples include, but are not limited to, pyrrolidine, piperidine, piperazine, morpholine, imidazoline, pyrazolidine, benzodiazepines, and the like.

Useful heterocycloalkyl groups include any of the above-mentioned $C_{1-10}$ alkyl groups substituted by any of the above-mentioned heterocyclic groups.

Useful heterocycloalkylamino groups include any of the above-mentioned heterocycloalkyl groups attached to an amino nitrogen, such as N-piperidinylethylamino.

Useful alkylamino and dialkylamino groups are —$NHR_{10}$ and —$NR_{10}R_{11}$, wherein $R_{10}$ and $R_{11}$ are $C_{1-10}$ alkyl groups.

Useful dialkylaminoalkyl groups include any of the above-mentioned $C_{1-10}$ alkyl groups substituted by any of the above-mentioned dialkylamino groups.

Useful dialkylaminoalkylamino groups include any of the above-mentioned dialkylaminoalkyl groups attached to an amino nitrogen, such as dimethylaminoethylamino.

Aminocarbonyl group is —$C(O)NH_2$.

Useful alkylaminocarbonyl groups are carbonyl groups substituted by —$NHR_{10}$ and —$NR_{10}R_{11}$, wherein $R_{10}$ and $R_{1-10}$ are $C_{1-10}$ alkyl groups.

Useful alkylthiol groups include any of the above-mentioned $C_{1-10}$ alkyl groups substituted by a —SH group.

A carboxy group is —COOH.

An azido group is —$N_3$.

An ureido group is —NH—C(O)—$NH_2$.

An amino group is —$NH_2$.

An amide group is an organic radical having —NHC(O)— as a functional group.

Optional substituents on $R_1$, $R_2$, and $R_{7-R11}$, include any one of halo, halo($C_{1-6}$) alkyl, aryl, heterocycle, cycloalkyl, $C_{1-6}$ alkyl, $C_{2-6}$ alkenyl, $C_{2-6}$ alkynyl, aryl($C_{1-6}$)alkyl, aryl($C_{2-6}$)alkenyl, aryl($C_{2-6}$)alkynyl, cycloalkyl($C_{1-6}$)alkyl, heterocyclo($C_{1-6}$)alkyl, hydroxy($C_{1-6}$)alkyl, amino($C_{1-6}$) alkyl, carboxy($C_{1-6}$)alkyl, alkoxy($C_{1-6}$)alkyl, nitro, amino, ureido, cyano, acylamino, hydroxy, thiol, acyloxy, azido, alkoxy, carboxy, aminocarbonyl, and $C_{1-6}$ alkylthiol groups mentioned above. Preferred optional substituents include: halo, halo($C_{1-6}$)alkyl, hydroxy($C_{1-6}$)alkyl, amino($C_{1-6}$)alkyl, hydroxy, nitro, $C_{1-6}$ alkyl, alkoxy and amino.

Certain of the compounds of Formulae I-V may exist as optical isomers and the invention includes both the racemic mixtures of such optical isomers as well as the individual enantiomers that may be separated according to methods that are well know to those of ordinary skill in the art.

Examples of pharmaceutically acceptable addition salts include inorganic and organic acid addition salts such as hydrochloride, hydrobromide, phosphate, sulphate, citrate, lactate, tartrate, maleate, fumarate, mandelate, acetate, dichloroacetate and oxalate.

Examples of prodrugs include esters or amides of Formulae I-V with $R_2$, $R_3$, $R_4$, $R_5$ and $R_6$ as hydroxyalkyl or aminoalkyl, and these may be prepared by reacting such compounds with anhydrides such as succinic anhydride.

The invention is also directed to a method for treating disorders responsive to the blockade of sodium channels in animals suffering thereof.

Particular preferred embodiments of the aryl substituted heteraryl compounds for use in method of this invention are represented by previously defined Formulae I-V.

The compounds of this invention may be prepared using methods known to those skilled in the art. 4-Aryl pyrimidine derivatives of compounds of Formula III can be prepared as illustrated by exemplary reactions in Scheme 1. Formation of the pyrimidine ring was accomplished as described by Fischer, G. W. (*J. Heterocyclic Chem.* 30: 1517–1519 (1993)), and Domagala, J. M. et al. (*J. Heterocyclic. Chem.* 26: 1147–1158 (1989)). Oxidation of the methyl pyrimidine employed the method of Sakamoto, T. et al. (*Chem. Pharm. Bull.* 28: 571–577 (1980)).

Scheme 1

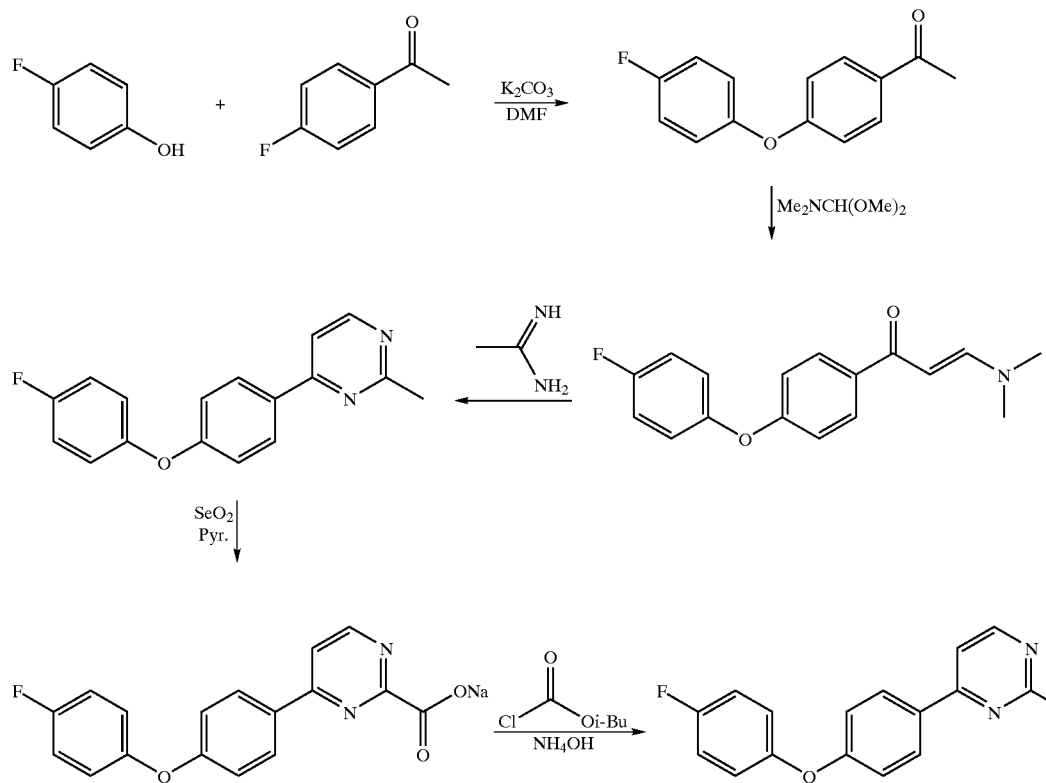

Pyrazine derivatives of compounds of Formula III can be prepared as illustrated by exemplary reactions in Scheme 2 using the method of Ohta, A. et al. (*J. Heterocycl. Chem.* 20: 311–320 (1983)), Sato, N. et al. (*J. Chem. Soc. Perkin Trans.* 121: 3167–3172 (1997)) and Gainer, (*J. Org. Chem.* 24: 691 (1959)).

2-Aryl pyrimidine derivatives of compounds of Formula III can be prepared as shown in Scheme 3. The pyrimidine ring was prepared as described by Burdeska, K. et al. (*Helv. Chim. Acta.* 64: 113–152 (1981)).

Scheme 2

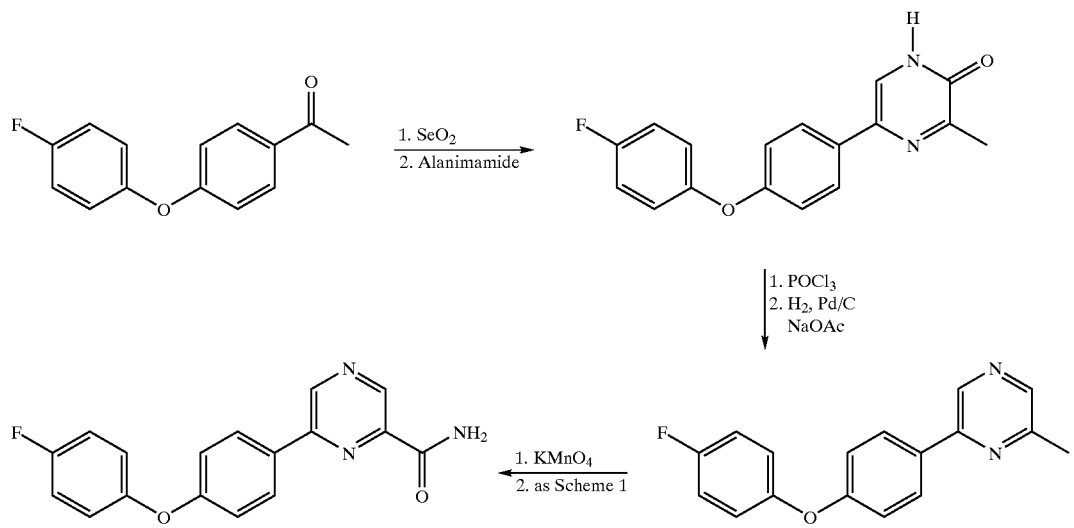

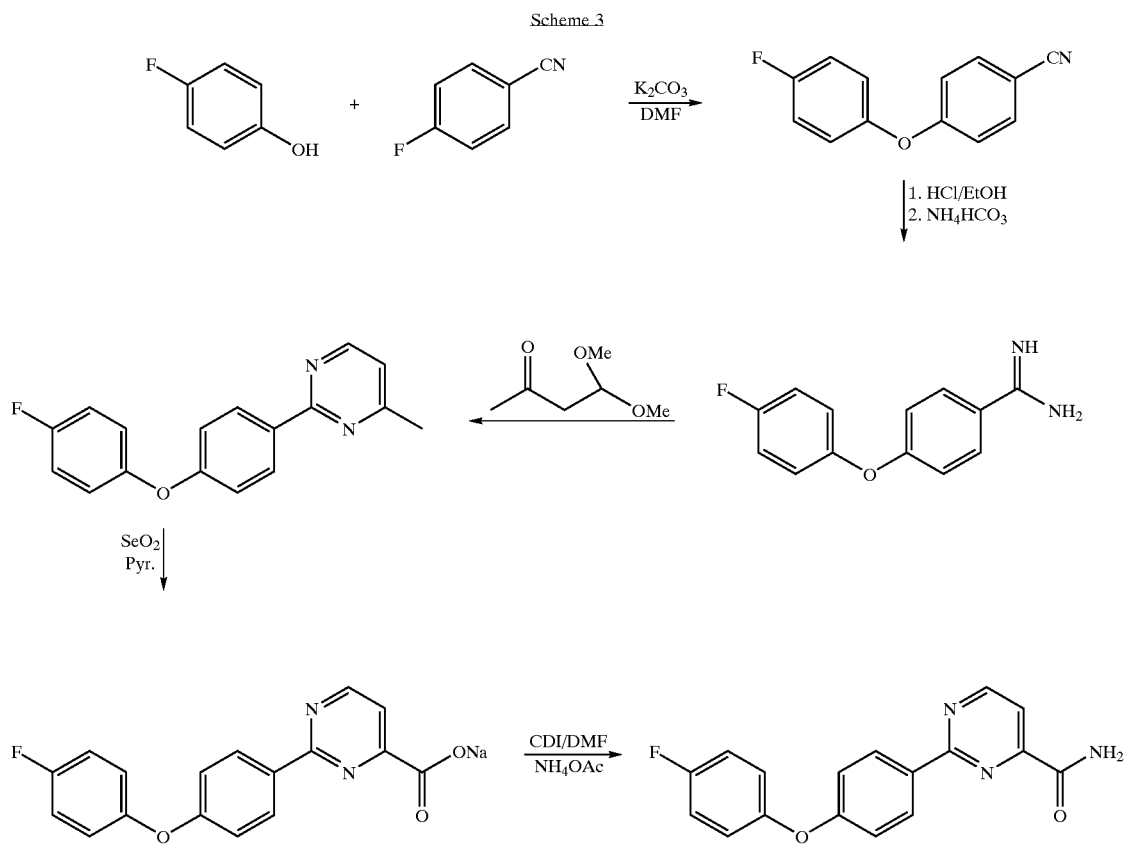
The 2-arylpyrimidine-4-carboxamides can also be prepared by coupling 2-chloropyrimidine-4-carboxamide and a boronic acid or boronate as shown in Scheme 4.
2-Chloropyrimidine-4-carboxamide is prepared from 4-methyl-2-pyrimidinol hydrochloride using the procedure of Daves et al. (*J. Heterocycl. Chem.* 1: 130–133 (1964)).
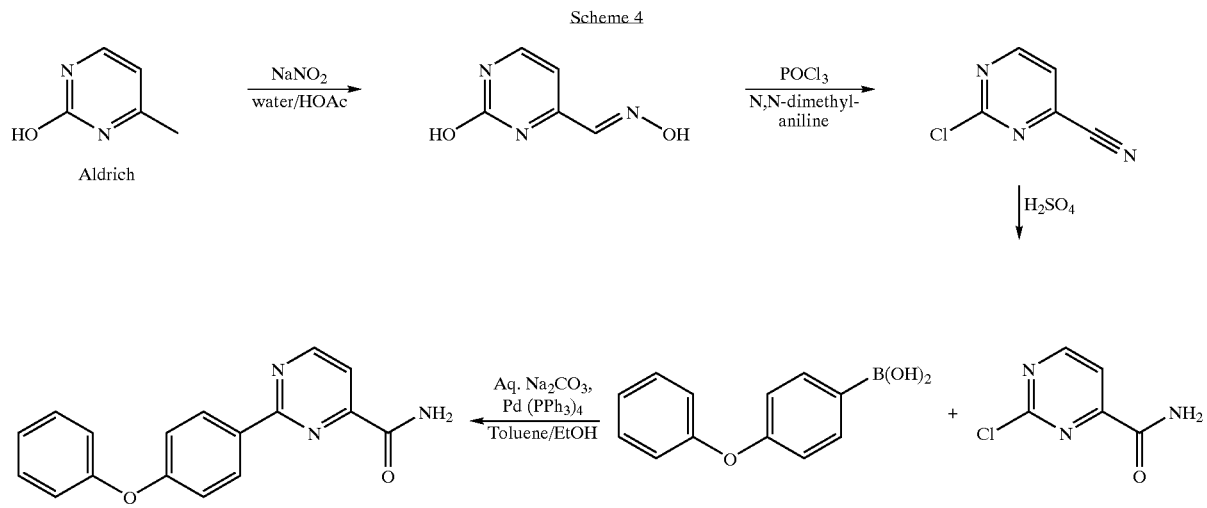

The chloride is then coupled with a boronic acid or boronate using the procedure described above.

Pyridine amides of Formula III can be synthesized as shown in Scheme 5:

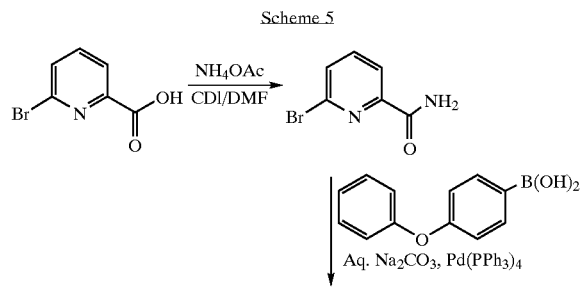

Scheme 5

6-Bromopicolinic acid (commercially available, marketed by, e.g., Aldrich) is converted to the corresponding amide and coupled with aryl boronic acids in the presence of catalytic $Pd(PPh_3)_4$. See for example Damnes, K. A. et al. (*Bioorg. Med. Chem. Lett.* 7:2673–2676 (1997)). The boronic acids are commercially available, or they can also be prepared from the corresponding bromides or iodides via the Grignard reagent or organolithium species using the procedures of Bettman, et al. (*J. Am. Chem. Soc.* 56:1865–1866 (1934)), Baldwin, J. E. et al. (*Tetrahedron Lett.* 39:707–710 (1998)), Li, J. J. et al. (*J. Med. Chem.* 38:4570–4578 (1995)) and Piettre, S. R. et al. (*J. Med. Chem.* 40:4208–4221 (1997)). Rather than using boronic acids, aryl boronates can be used and are prepared from aryl bromides, iodides and triflates using the method of Murata, M. et al. (*J. Org. Chem.* 65:164–168 (2000)) and coupled using the method of Giroux, A. et al. (*Tetrahedron* 38:3841 (1997)).

Alternatively, 2-bromo-6-methylpyridine can be coupled with 4-bromoboronic acid and the bromide formed subjected to Ullmann coupling with a phenol in the presence of $Cs_2CO_3$ and copper powder (Buchwald, S. L. et al., *J. Am. Chem. Soc.* 119:10539–10540 (1997)). The methyl group on the pyridine is then converted in two steps to the desired amide using the method described above.

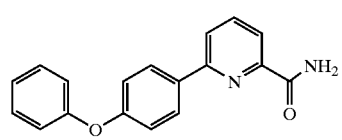

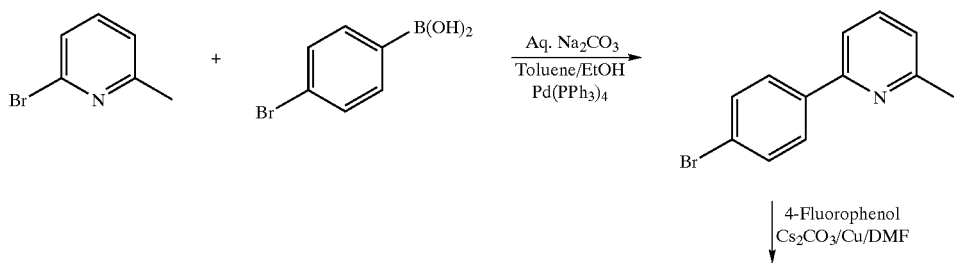

Scheme 6

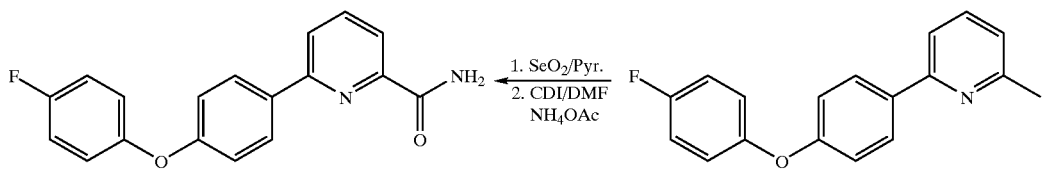

Pyrazines can be prepared by coupling a suitably substituted 6-halopyrazine with an aryl boronic acid using the method described in the synthesis of the corresponding pyridine as shown in the Scheme 7 below.
Scheme 7
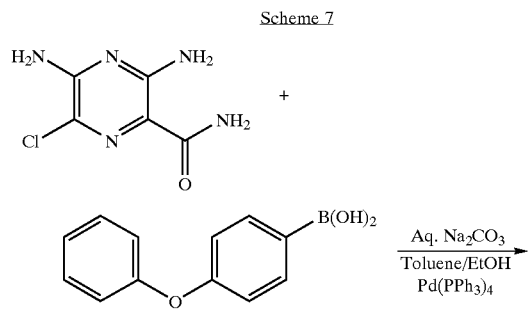
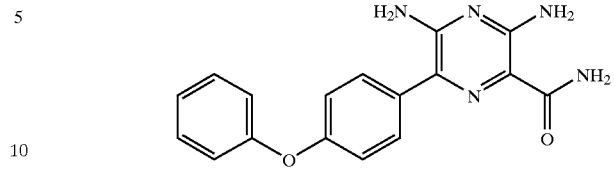
1,3,5-Triazines of the present invention can be prepared, for example, using the method of Chen et al. (*J. Org. Chem.* 60:8428–8430 (1995)) as follows:
Scheme 8
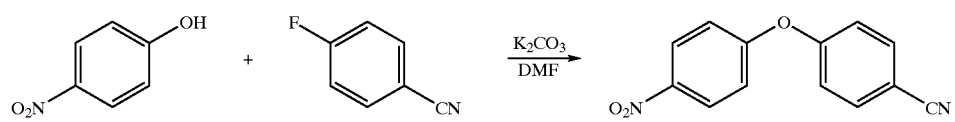
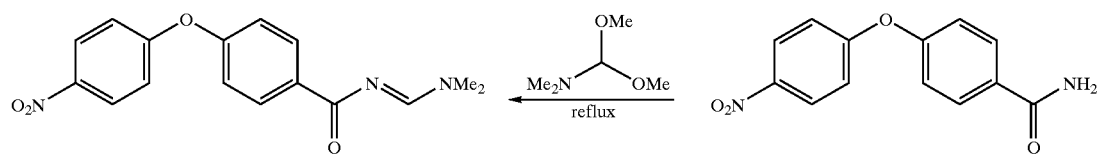
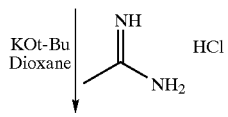
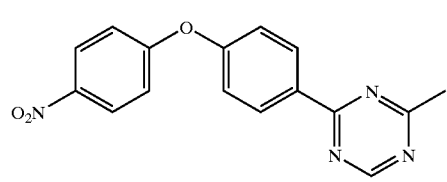

5-Aryl-1,2,4-triazines of the invention can be prepared using the procedure of Benson, S. et al. (*J. Org. Chem.* 55: 3257–3269 (1990)) as shown in Scheme 9. Ethyl thiooxamate (Aldrich) can be converted to the corresponding hydrazone using the method of Raetz and Schroeder (*J. Org. Chem.* 23: 1931–1933 (1958)).

Scheme 9

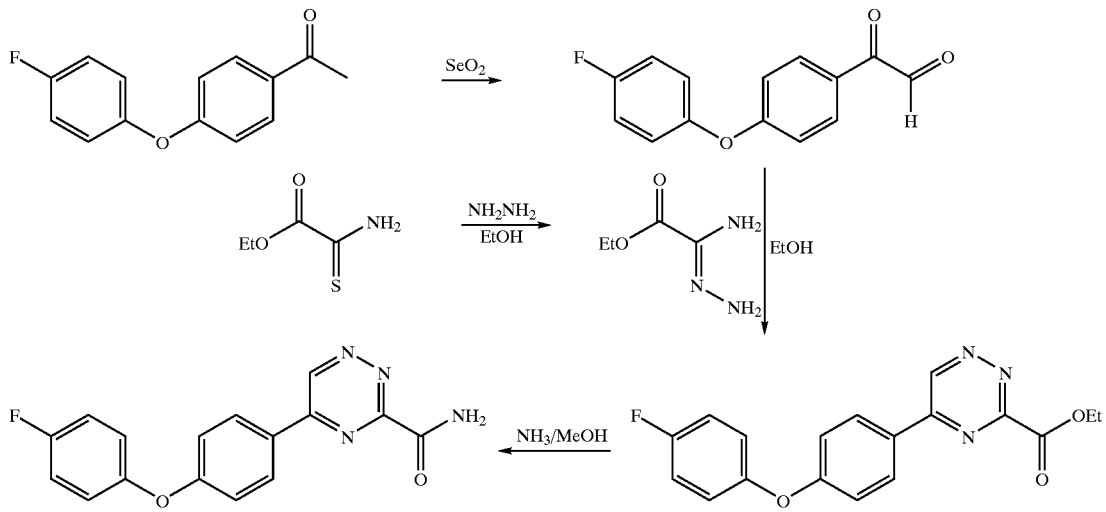

3-Aryl-1,2,4-triazines of the invention can be prepared as shown in Scheme 10. The sodium salt of hydrazine can be added to a benzonitrile using the method of Kauffmann, T. et al. (*Angew. Chem.* 75: 344 (1963)). Formation of the triazine ring can be accomplished as described by Shkurko, O. P. et al. (*Chem. Heterocycl. Compd.* (*Engl. Transl.*) 23: 216–221 (1987)). Conversion to the desired amide can be carried out as disclosed in Rykowski and Makosza (*Tetrahedron Lett.* 25: 4795–4796 (1984)) and Rykowski, A. et al. (*J. Heterocycl. Chem.* 33: 1567–1572 (1996)).

Scheme 10

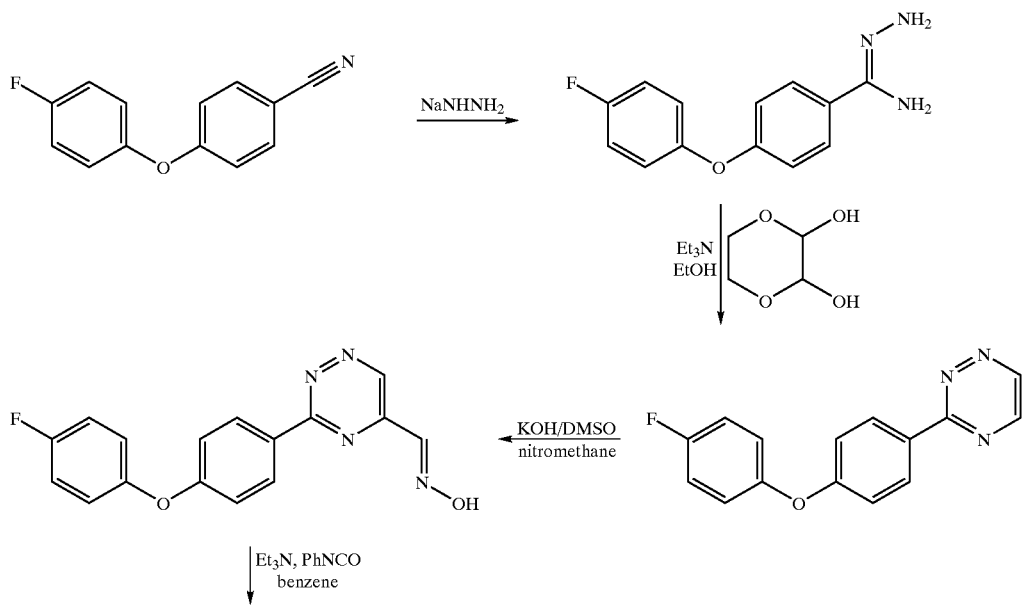

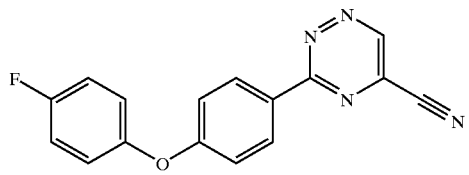 →H₂SO₄→ 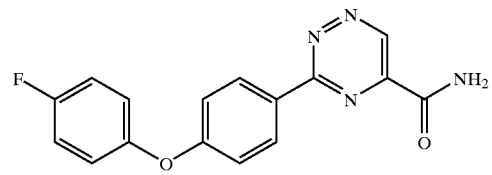

The compounds of Formula V can be prepared by the methods described above using suitable starting compounds.

The compounds of the present invention were assessed by electrophysiological assays in dissociated hippocampal neurons for sodium channel blocker activity. These compounds also could be assayed for binding to the neuronal voltage-dependent sodium channel using rat forebrain membranes and [$^3$H]BTX-B.

Sodium channels are large transmembrane proteins that are expressed in various tissues. They are voltage sensitive channels and are responsible for the rapid increase of $Na^+$ permeability in response to depolarization associated with the action potential in many excitable cells including muscle, nerve and cardiac cells.

One aspect of the present invention is the discovery of the mechanism of action of the compounds herein described as specific $Na^+$ channel blockers. Based upon the discovery of this mechanism, these compounds are contemplated to be useful in treating or preventing neuronal loss due to focal or global ischemia, and in treating or preventing neurodegenerative disorders including ALS, anxiety, and epilepsy. They are also expected to be effective in treating, preventing or ameliorating neuropathic pain, surgical pain, chronic pain and tinnitus. The compounds are also expected to be useful as antiarrhythmics, anesthetics and antimanic depressants.

The present invention is directed to compounds of Formulae I-V that are blockers of voltage-sensitive sodium channels. According to the present invention, those compounds having preferred sodium channel blocking properties exhibit an $IC_{50}$ of about 100 $\mu$M or less in the electrophysiological assay described herein. Preferably, the compounds of the present invention exhibit an $IC_{50}$ of 10 $\mu$M or less. Most preferably, the compounds of the present invention exhibit an $IC_{50}$ of about 1.0 $\mu$M or less. Substituted heteroaryl compounds of the present invention may be tested for their $Na^+$ channel blocking activity by the following electrophysiological and binding assays.

Electrophysiological Assay 1:

Cell preparation: HEK-293 (NaIIA-B2) cell line stably expressing the rBIIA isoform of $Na^+$ channels was established in-house. The cells were cultured using standard techniques, as described previously (Verdoom, T. A, et al., Neuron 4:919–928 (1990)). For electrophysiology, cells were plated onto poly-D-lysine pre-coated Cellware 35 mm Petri dishes (BIOCOAT, Becton Dickinson) at a density of ~10$^4$ cells/dish on the day of re-seeding from confluent cultures. Our experience has been that cells are suitable for recordings for 2–3 days after plating.

Patch-clamp recordings of voltage-sensitive $Na^+$ currents: Whole-cell voltage-clamp recordings were made using conventional patch-clamp techniques (Hamill et al., Pfluegers Arch. 391:85–100 (1981)) with an Axopatch 200A amplifier (Axon Instruments, Foster City, Calif.). The recording chamber was continuously superfused with the external solution (150 mM NaCl, 5.4 mM KCl, 1.8 mM CaCl$_2$, 1 mM MgCl$_2$, 10 mM HEPES, 10 mM glucose, pH 7.4 adjusted with NaOH, osmolality ~320 mmol/kg) at a speed of about 1 mL/min. Recording pipettes were pulled from the thick-walled capillaries (WPI, Sarasota, Fla.) and fire-polished. The pipette resistances ranged from 1 to 3 MΩ when the pipettes were filled with internal solution containing (in mM): 130 CsF, 20 NaCl, 2 MgCl$_2$, 10 EGTA, 10 HEPES, pH adjusted to 7.4 with CsOH, osmolality ~310 mmol/kg. Drugs and intervening wash-outs were applied through a linear array of flow pipes (Drummond Microcaps, 2 $\mu$L, 64-mm length). Compounds are dissolved in dimethylsulfoxide (DMSO) to make a 30 mM stock solution, which was subsequently diluted into the external solution to give final concentrations of 0.1–100 $\mu$M. At the highest (1%) concentration, DMSO inhibited the size of $Na^+$ current only slightly. Currents were recorded at room temperature (22–25° C.), filtered at 3 kHz with an active 8-pole Bessel filter (Frequency Devices, Haverhill, Mass.), digitized at 10–50 $\mu$s intervals, and stored using Digidata 1200 analog/digital interface with Pclamp6/Clampex software (Axon Instruments). Series resistance was cancelled typically by ~75% when necessary.

Figure 1B:
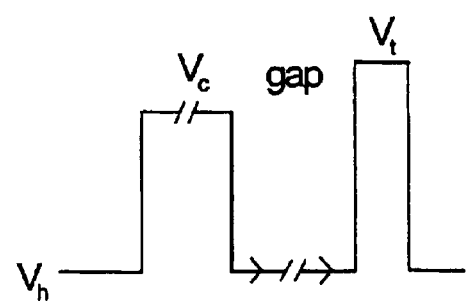
Figure 1C:
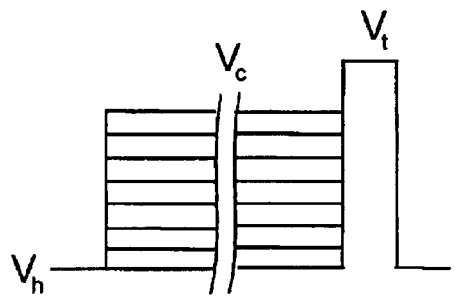
Figure 1D:
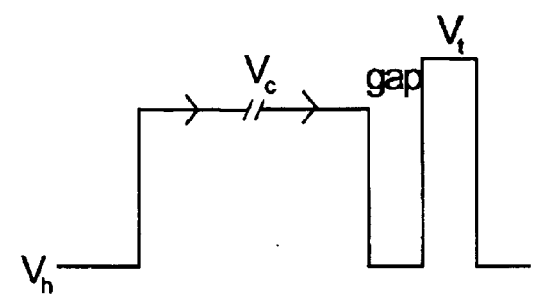

The following voltage pulse protocols A, B, C, and D were used to assess the potency and kinetics of inhibition of the $Na^+$ channels by the compounds (FIGS. 1A–1D). Current-voltage relationship (IV-curve), protocol A (FIG. 1A), was used to report the voltage at which the maximal inward $Na^+$ current is achieved. This voltage was used throughout the experiment as testing voltage, $V_t$. The steady-state inactivation (or, availability) curve, protocol C (FIG. 1C), was used to get the voltage at which almost complete ($\geq$95%) inactivation of $Na^+$ channels occurs; it served as voltage for conditioning prepulse, $V_c$, throughout the experiment. Protocol B (FIG. 1B) reports how fast the channels recover from inactivation at hyperpolarized voltages. This permitted us to set up the duration of the hyperpolarization gap which is used in measurement of the kinetics of binding of compounds to inactivated $Na^+$ channels (protocol D (FIG. 1D)). Channel repriming under control conditions was fast ($\geq$90% recovery during first 5–10 ms). If a drug substantially retards the repriming process then it becomes possible (protocol D) to accurately measure the kinetics of binding of the inhibitor to inactivated channels as well as the steady-state affinity ($k_+$ and $K_i$). To estimate $k_+$ values the reduction in peak currents in successive trials with varying pre-pulse duration was plotted as a function of pre-pulse duration and the time constant ($\tau$) measured by mono-exponential fit. A plot of 1/$\tau$ as a function of antagonist concentration then allowed calculating of the macroscopic binding rates of the antagonists. To determine $K_i$ values the partial inhibition curves measured by fractional responses in steady-state was fitted with the logistic equation:

$$I/I_{control}=1/(1+([antagonist]/K_i)^p), \quad \text{Eq. 1}$$

where $I_{control}$ is the maximal $Na^+$ current in the absence of antagonist, is the drug concentration, $K_j$ is the concentration of antagonist that produces half maximal inhibition, and p is the slope factor.

Electrophysiological Assay 2:

Electrophysiological Assay 2 was used to measure potencies of compounds of the present invention rBIIa/beta 1 sodium channels expressed in Xenopus oocytes.

Preparation of cRNA encoding cloned rat brain type IIa (rBIIa) and beta 1 (β1): cDNA clones encoding the rat brain beta 1 subunit were cloned in house using standard methods, and mRNA were prepared by standard methods. mRNA encoding rBIIa was provided by Dr. A. Golden (UC Irvine). The mRNAs were diluted and stored at −80° C. in 1 μL aliquots until injection.

Preparation of oocytes: Mature female *Xenopus laevis* were anaesthetized (20–40 min) using 0.15% 3-aminobenzoic acid ethyl ester (MS-222) following established procedures (Woodward, R. M., et al., *Mol. Pharmacol.* 41:89–103 (1992)).

Two to six ovarian lobes were surgically removed. Oocytes at developmental stages V–VI were dissected from the ovary, oocytes were still surrounded by enveloping ovarian tissues. Oocytes were defolliculated on the day of surgery by treatment with collagenase (0.5 mg/mL Sigma Type I, or Boehringer Mannheim Type A, for 0.5–1 hr). Treated oocytes were vortexed to dislodge epithelia, washed repeatedly and stored in Barth's medium containing 88 mM NaCl, 1 mM KCl, 0.41 mM $CaCl_2$, 0.33 mM $Ca(NO_3)_2$, 0.82 mM $MgSO_4$, 2.4 mM $NaHCO_3$, 5 mM HEPES, pH 7.4 adjusted with 0.1 mg/mL gentamycin sulphate.

Micro-injection of oocytes: Defolliculated oocytes were micro-injected using a Nanoject injection system (Drummond Scientific Co., Broomall, Pa.). Injection pipettes were beveled to minimize clogging. Tip diameter of injection pipettes was 15–35 μm. Oocytes were microinjected with approximately 50 nL 1:10 ratio mixtures of cRNAs for rBIIa and beta 1 respectively.

Electrophysiology: Membrane current responses were recorded in frog Ringer solution containing 115 mM NaCl, 2 mM KCl, 1.8 mM $CaCl_2$, 5 mM HEPES, pH 7.4. Electrical recordings were made using a conventional two-electrode voltage clamp (Dagan TEV-200) over periods ranging between 1–7 days following injection. The recording chamber was a simple gravity fed flow-through chamber (volume 100–500 mL depending on adjustment of aspirator). Oocytes were placed in the recording chamber, impaled with electrodes and continuously perfused (5–15 mL min$^{-1}$) with frog Ringer's solution. The tested compounds were applied by bath perfusion.

Voltage protocols for evoking sodium channel currents: The standard holding potential for whole oocyte clamp was −120 mV. Standard current-voltage relationships were elicited by 40 ms depolarizing steps starting from −60 mV to +50 mV in 10 mV increments. Peak currents were measured as the maximum negative current after depolarizing voltage steps. The voltage from maximum current response was noted and used for the next voltage protocol.

The purpose was to find compounds that are state dependent modifiers of neuronal sodium channels. Preferably, the compounds have a low affinity for the rested/closed state of the channel, but a high affinity for the inactivated state. The following voltage protocol was used to measure a compounds affinity for the inactivated state. Oocytes were held at a holding potential of −120 mV. At this membrane voltage, nearly all of the channels would be in the closed state. Then a 4 second depolarization was made to the voltage where the maximum current was elicited. At the end of this depolarization, nearly all the channels would be in the inactivated state. A 10 ms hyperpolarizing step was then made in order to remove some channels from the incativated state. A final depolarizing test pulse was used to assay the sodium current after this prolonged depolarization (see analysis below). Sodium currents were measured at this test pulse before and after the application of the tested compound. Data was acquired using pClamp 8.0 software and analyzed with clampfit software (Axon instruments).

Data analysis: Apparent inhibition constants ($K_i$ values) for antagonists were determined from single point inhibition data using the following equation (a generalized form of the Cheng-Prusoff equation) (Leff, P. and I. G. Dougall, TiPS 14:110–112 (1993)).

$$K_i=(FR/1-FR)*[drug] \qquad Eq.2$$

Where FR is the fractional response and is defined as sodium current elicited from the final depolarizing test pulse prior to application of the drug divided by the sodium current measured in the presence of the drug. [drug] is the concentration of the drug used.

Drugs: Drugs were initially made up at concentrations of 2–10 mM in DMSO. Dilutions were then made to generate a series of DMSO stocks over the range 0.3 μM to 10 mM—depending upon the potency of the compound. Working solutions were made by 1000–3000 fold dilution of stocks into Ringer. At these dilutions DMSO alone had little or no measurable effects on membrane current responses. DMSO stocks of drugs were stored in the dark at 4° C. Ringer solutions of drugs were made up fresh each day of use.

In vitro Binding Assay:

The ability of compounds of the present invention to modulate either site 1 or site 2 of the Na$^+$ channel was determined following the procedures fully described in Yasushi, *J. Biol. Chem.* 261:6149–6152 (1986) and Creveling, *Mol. Pharmacol.* 23:350–358 (1983), respectively. Rat forebrain membranes were used as sources of Na$^+$ channel proteins. The binding assays were conducted in 130 μM choline chloride at 37° C. for 60-minute incubation with [$^3$H] saxitoxin and [$^3$H] batrachotoxin as radioligands for site 1 and site 2, respectively.

In vivo Pharmacology:

The compounds of the present invention may be tested for in vivo anticonvulsant activity after i.v., p.o. or i.p. injection using a number of anticonvulsant tests in mice, including the maximum electroshock seizure test (MES). Maximum electroshock seizures were induced in male NSA mice weighing between 15–20 g and male Sprague-Dawley rats weighing between 200–225 g by application of current (50 mA, 60 pulses/sec, 0.8 msec pulse width, 1 sec duration, D.C., mice; 99 mA, 125 pulses/sec, 0.8 msec pulse width, 2 sec duration, D.C., rats) using a Ugo Basile ECT device (Model 7801). Mice were restrained by gripping the loose skin on their dorsal surface and saline-coated corneal electrodes were held lightly against the two corneae. Rats were allowed free movement on the bench top and ear-clip electrodes were used. Current was applied and animals were observed for a period of up to 30 seconds for the occurrence of a tonic hindlimb extensor response. A tonic seizure was defined as a hindlimb extension in excess of 90 degrees from the plane of the body. Results were treated in a quantal manner.

The compounds may be tested for their antinociceptive activity in the formalin model as described in Hunskaar, S., O. B. Fasmer, and K. Hole, *J. Neurosci. Methods* 14: 69–76 (1985). Male Swiss Webster NIH mice (20–30 g; Harlan, San Diego, Calif.) were used in all experiments. Food was withdrawn on the day of experiment. Mice were placed in Plexiglass jars for at least 1 hour to accommodate to the environment. Following the accommodation period mice were weighed and given either the compound of interest administered i.p. or p.o., or the appropriate volume of vehicle (10% Tween-80). Fifteen minutes after the i.p. dosing, and 30 minutes after the p.o. dosing mice were injected with formalin (20 µL of 5% formaldehyde solution in saline) into the dorsal surface of the right hind paw. Mice were transferred to the Plexiglass jars and monitored for the amount of time spent licking or biting the injected paw. Periods of licking and biting were recorded in 5 minute intervals for 1 hour after the formalin injection. All experiments were done in a blinded manner during the light cycle. The early phase of the formalin response was measured as licking/biting between 0–5 minutes, and the late phase was measured from 15–50 minutes. Differences between vehicle and drug treated groups were analyzed by one-way analysis of variance (ANOVA). A P value <0.05 was considered significant. Having activity in blocking the acute and second phase of formalin-induced paw-licking activity, the compounds are considered to be efficacious for acute and chronic pain.

The compounds may be tested for their potential for the treatment of chronic pain (antiallodynic and antihyperalgesic activities) in the Chung model of peripheral neuropathy. Male Sprague-Dawley rats weighing between 200–225 g were anesthetized with halothane (1–3% in a mixture of 70% air and 30% oxygen) and their body temperature controlled during anesthesia through use of a homeothermic blanket. A 2-cm dorsal midline incision was then made at the L5 and L6 level and the para-vertibral muscle groups retracted bilaterally. L5 and L6 spinal nerves were then be exposed, isolated, and tightly ligated with 6-0 silk suture. A sham operation was performed exposing the contralateral L5 and L6 spinal nerves as a negative control.

Tactile Allodynia: Rats were transferred to an elevated testing cage with a wire mesh floor and allowed to acclimate for five to ten minutes. A series of Semmes-Weinstein monofilaments were applied to the plantar surface of the hindpaw to determine the animal's withdrawal threshold. The first filament used possessed a buckling weight of 9.1 gms (0.96 log value) and was applied up to five times to see if it elicited a withdrawal response. If the animal had a withdrawal response then the next lightest filament in the series would be applied up to five times to determine if it could elicit a response. This procedure was repeated with subsequent lesser filaments until there was no response and the lightest filament that elicited a response was recorded. If the animal did not have a withdrawal response from the initial 9.1 gms filament then subsequent filaments of increased weight were applied until a filament elicited a response and this filament was then recorded. For each animal, three measurements were made at every time point to produce an average withdrawal threshold determination. Tests were performed prior to and at 1, 2, 4 and 24 hours post drug administration. Tactile allodynia and mechanical hyperalgesia tests were conducted concurrently.

Mechanical Hyperalgesia: Rats were transferred to an elevated testing cage with a wire mesh floor and allowed to acclimate for five to ten minutes. A slightly blunted needle was touched to the plantar surface of the hindpaw causing a dimpling of the skin without penetrating the skin. Administration of the needle to control paws typically produced a quick flinching reaction, too short to be timed with a stopwatch and arbitrarily given a withdrawal time of 0.5 second. The operated side paw of neuropathic animals exhibited an exaggerated withdrawal response to the blunted needle. A maximum withdrawal time of ten seconds was used as a cutoff time. Withdrawal times for both paws of the animals were measured three times at each time point with a five-minute recovery period between applications. The three measures were used to generate an average withdrawal time for each time point. Tactile allodynia and mechanical hyperalgesia tests were conducted concurrently.

The compounds may be tested for their neuroprotective activity after focal and global ischemia produced in rats or gerbils according to the procedures described in Buchan et al. (*Stroke, Suppl.* 148–152 (1993)) and Sheardown et al. (*Eur. J. Pharmacol.* 236:347–353 (1993)) and Graham et al. (*J. Pharmacol. Exp. Therap.* 276:1–4 (1996)).

The compounds may be tested for their neuroprotective activity after traumatic spinal cord injury according to the procedures described in Wrathall et al. (*Exp. Neurology* 137:119–126 (1996)) and Iwasaki et al. (*J. Neuro Sci.* 134:21–25 (1995)).

Compositions within the scope of this invention include all compositions wherein the compounds of the present invention are contained in an amount that is effective to achieve its intended purpose. While individual needs vary, determination of optimal ranges of effective amounts of each component is within the skill of the art. Typically, the compounds may be administered to mammals, e.g. humans, orally at a dose of 0.0025 to 50 mg/kg, or an equivalent amount of the pharmaceutically acceptable salt thereof, per day of the body weight of the mammal being treated for epilepsy, neurodegenerative diseases, anesthetic, arrhythmia, manic depression, and pain. For intramuscular injection, the dose is generally about one-half of the oral dose.

In the method of treatment or prevention of neuronal loss in global and focal ischemia, brain and spinal cord trauma, hypoxia, hypoglycemia, status epilepsy and surgery, the compound can be administrated by intravenous injection at a dose of about 0.025 to about 10 mg/kg.

The unit oral dose may comprise from about 0.01 to about 50 mg, preferably about 0.1 to about 10 mg of the compound. The unit dose may be administered one or more times daily as one or more tablets each containing from about 0.1 to about 10, conveniently about 0.25 to 50 mg of the compound or its solvates.

In addition to administering the compound as a raw chemical, the compounds of the invention may be administered as part of a pharmaceutical preparation containing suitable pharmaceutically acceptable carriers comprising excipients and auxiliaries which facilitate processing of the compounds into preparations which can be used pharmaceutically. Preferably, the preparations, particularly those preparations which can be administered orally and which can be used for the preferred type of administration, such as tablets, dragees, and capsules, and also preparations which can be administered rectally, such as suppositories, as well as suitable solutions for administration by injection or orally, contain from about 0.01 to 99 percent, preferably from about 0.25 to 75 percent of active compound(s), together with the excipient.

Also included within the scope of the present invention are the non-toxic pharmaceutically acceptable salts of the compounds of the present invention. Acid addition salts are formed by mixing a solution of the particular heteroaryl compound of the present invention with a solution of a pharmaceutically acceptable non-toxic acid such as hydrochloric acid, fumaric acid, maleic acid, succinic acid, acetic acid, citric acid, tartaric acid, carbonic acid, phosphoric acid, oxalic acid, dichloroacetic acid, and the like. Basic salts are formed by mixing a solution of the heteroaryl compound of the present invention with a solution of a pharmaceutically acceptable non-toxic base such as sodium hydroxide, potassium hydroxide, choline hydroxide, sodium carbonate and the like.

The pharmaceutical compositions of the invention may be administered to any animal that may experience the beneficial effects of the compounds of the invention. Foremost among such animals are mammals, e.g., humans, although the invention is not intended to be so limited.

The pharmaceutical compositions of the present invention may be administered by any means that achieve their intended purpose. For example, administration may be by parenteral, subcutaneous, intravenous, intramuscular, intraperitoneal, transdermal, or buccal routes. Alternatively, or concurrently, administration may be by the oral route. The dosage administered will be dependent upon the age, health, and weight of the recipient, kind of concurrent treatment, if any, frequency of treatment, and the nature of the effect desired.

The pharmaceutical preparations of the present invention are manufactured in a manner which is itself known, for example, by means of conventional mixing, granulating, dragee-making, dissolving, or lyophilizing processes. Thus, pharmaceutical preparations for oral use can be obtained by combining the active compounds with solid excipients, optionally grinding the resulting mixture and processing the mixture of granules, after adding suitable auxiliaries, if desired or necessary, to obtain tablets or dragee cores.

Suitable excipients are, in particular, fillers such as saccharides, for example lactose or sucrose, mannitol or sorbitol, cellulose preparations and/or calcium phosphates, for example tricalcium phosphate or calcium hydrogen phosphate, as well as binders such as starch paste, using, for example, maize starch, wheat starch, rice starch, potato starch, gelatin, tragacanth, methyl cellulose, hydroxypropylmethylcellulose, sodium carboxymethylcellulose, and/or polyvinyl pyrrolidone. If desired, disintegrating agents may be added such as the above-mentioned starches and also carboxymethyl-starch, cross-linked polyvinyl pyrrolidone, agar, or alginic acid or a salt thereof, such as sodium alginate. Auxiliaries are, above all, flow-regulating agents and lubricants, for example, silica, talc, stearic acid or salts thereof, such as magnesium stearate or calcium stearate, and/or polyethylene glycol. Dragee cores are provided with suitable coatings that, if desired, are resistant to gastric juices. For this purpose, concentrated saccharide solutions may be used, which may optionally contain gum arabic, talc, polyvinyl pyrrolidone, polyethylene glycol and/or titanium dioxide, lacquer solutions and suitable organic solvents or solvent mixtures. In order to produce coatings resistant to gastric juices, solutions of suitable cellulose preparations such as acetylcellulose phthalate or hydroxypropymethyl-cellulose phthalate, are used. Dye stuffs or pigments may be added to the tablets or dragee coatings, for example, for identification or in order to characterize combinations of active compound doses.

Other pharmaceutical preparations which can be used orally include push-fit capsules made of gelatin, as well as soft, sealed capsules made of gelatin and a plasticizer such as glycerol or sorbitol. The push-fit capsules can contain the active compounds in the form of granules which may be mixed with fillers such as lactose, binders such as starches, and/or lubricants such as talc or magnesium stearate and, optionally, stabilizers. In soft capsules, the active compounds are preferably dissolved or suspended in suitable liquids, such as fatty oils, or liquid paraffin. In addition, stabilizers may be added.

Possible pharmaceutical preparations, which can be used rectally, include, for example, suppositories, which consist of a combination of one or more of the active compounds with a suppository base. Suitable suppository bases are, for example, natural or synthetic triglycerides, or paraffin hydrocarbons. In addition, it is also possible to use gelatin rectal capsules which consist of a combination of the active compounds with a base. Possible base materials include, for example, liquid triglycerides, polyethylene glycols, or paraffin hydrocarbons.

Suitable formulations for parenteral administration include aqueous solutions of the active compounds in water-soluble form, for example, water-soluble salts and alkaline solutions. In addition, suspensions of the active compounds as appropriate oily injection suspensions may be administered. Suitable lipophilic solvents or vehicles include fatty oils, for example, sesame oil, or synthetic fatty acid esters, for example, ethyl oleate or triglycerides or polyethylene glycol-400 (the compounds are soluble in PEG-400). Aqueous injection suspensions may contain substances which increase the viscosity of the suspension, and include, for example, sodium carboxymethyl cellulose, sorbitol, and/or dextran. Optionally, the suspension may also contain stabilizers.

The following examples are illustrative, but not limiting, of the method and compositions of the present invention. Other suitable modifications and adaptations of the variety of conditions and parameters normally encountered in clinical therapy and which are obvious to those skilled in the art are within the spirit and scope of the invention.

EXAMPLE 1

4-[4-(4-Fluorophenoxy)phenyl]-pyrimidine-2-carboxamide a) 1-[4-(4-Fluorophenoxy)phenyl]ethanone: A mixture of 4-fluorophenol (4.45 g, 39.3 mmol), 4-fluoroacetophenone (4.4 mL, 36 mmol), and potassium carbonate (13 g, 94 mmol) in DMF (40 mL) was refluxed overnight. The mixture was allowed to cool to room temperature, then partitioned between ethyl acetate (200 mL) and water (200 mL). The separated aqueous layer was extracted with ethyl acetate (3×100 mL). The combined ethyl acetate layers were washed with an aqueous sodium hydroxide solution (2N, 200 mL), washed twice with water (200 mL each), dried over sodium sulfate, filtered, and evaporated under reduced pressure to give a dark oil. The oil solidified on standing at room temperature overnight. The weight of crude 1-[4-(4-fluorophenoxy)phenyl]ethanone was 6.7 g (80%). $^1$H NMR (CDCl$_3$): 7.96 (d, J 9.0 Hz, 2H), 7.11–7.06 (m, 4H), 6.98 (d, J=8.7 Hz, 2H), 2.59 (s, 3H).

b) 3-Dimethylamino-1-[4-(4-fluorophenoxy)phenyl]-propenone: A mixture of crude 1-[4-(4-fluorophenoxy) phenyl]ethanone (17.9 mmol) and N,N-dimethylformamide dimethylacetal (2.6 mL, 18.4 mmol) in DMF (20 mL) was refluxed for 24 hours. The solution was then partitioned between ethyl acetate and water. The aqueous layer was extracted twice with ethyl acetate and the combined ethyl acetate layers were washed twice with water, dried over sodium sulfate, filtered, and evaporated under reduce pressure to give 3-dimethylamino-1-[4-(4-fluorophenoxy) phenyl]-propenone as a yellow solid, mp 115°–118° C.

c) 2-Methyl-4-[4-(4-fluorophenoxy)phenyl]-pyrimidine: Acetamidine hydrochloride (2.00 g, 20.1 mmol) and potassium tert-butoxide (2.37 g, 20.1 mmol) in anhydrous THF (20 mL) were refluxed for 50 minutes. 3-Dimethylamino-1-[4-(4-fluorophenoxy)phenyl]-propenone (3.96 g, 13.9 mmol) in anhydrous THF (20 mL) was added to the reaction and refluxed for an additional 4 hours. The reaction was allowed to cool to room temperature and concentrated in vacuo. The residue was partitioned between ethyl acetate and water. The aqueous layer was extracted twice with ethyl acetate. The combined organic layers were dried over sodium sulfate, filtered, and evaporated under reduced pressure to give solid. The crude product was purified by column chromatography (7:3 hexane/ethyl acetate) to give 1.7 g (44%) of the title compound as a yellow solid. $^1$H NMR (CDCl$_3$) δ 8.61 (d, J=5.1 Hz, 1H), 8.05 (d, J=8.4 Hz, 2H), 7.42 (d, J=5.7 Hz, 1H), 7.05–7.02 (m, 6H), 2.77 (s, 3H).

d) 4-[4-(4-Fluorophenoxy)phenyl]-pyrimidine-2-carboxylic acid: 4-[4-(4-Fluorophenoxy)phenyl]-2-methyl-pyrimidine (1.70 g, 6.03 mmol) and selenium dioxide (1.16 g, 10.4 mmol) in pyridine (40 mL) were refluxed overnight. The mixture was filtered to remove a solid that had formed. The filtrate was evaporated under reduced pressure. The residue was added to a 2N aqueous sodium hydroxide solution. The resulting solid was collected by filtration and partitioned between aqueous hydrochloric acid (2N) and ethyl acetate. The aqueous layer was extracted two more times with ethyl acetate. The combined organic layers were dried over sodium sulfate, filtered, and evaporated under reduced pressure to give 1.5 g (80%) of the acid as a solid. $^1$H NMR (DMSO-d$_6$): δ 8.95 (d, J=5.4 Hz, 1H), 8.25 (d, J=8.7 Hz, 2H), 8.18 (d, J=5.4 Hz, 1H), 7.30 (t, J=8.7 Hz, 2H), 7.22–7.17 (m, 2H), 7.13 (d, J=9.3 Hz, 2H).

e) 4-[4-(4-Fluorophenoxy)phenyl]-pyrimidine-2-carboxamide: A mixture of 4-[4-(4-fluorophenoxy)phenyl]-pyrimidine-2-carboxylic acid (1.00 g, 3.23 mmol) and carbonyl diimidazole (1.10 g, 6.78 mmol) in DMF (10 mL) were stirred at room temperature for 2 hours. Solid ammonium acetate (2.10 g, 27.2 mmol) was then added to the reaction. After stirring overnight at room temperature, the reaction was diluted with ethyl acetate, washed several times with water, dried over sodium sulfate, filtered, and evaporated under reduced pressure. The crude product was purified by column chromatography (gradient from 100% ethyl acetate to 95:5 ethyl acetate/methanol) to give 669 mg (67%) of the desired product as yellow solid, mp 180°–182° C. $^1$H NMR (DMSO-d$_6$): δ 8.94 (d, J=5.1 Hz, 1H), 8.38 (d, J=8.7 Hz, 2H), 8.34 (bs, 1H), 8.15 (d, J=5.4 Hz, 1H), 7.83 (bs, 1H), 7.30 (t, J=8.4 Hz, 2H), 7.22–7.17 (m, 2H), 7.12, (d, J=8.7 Hz, 2H).

The following compounds were prepared similarly:
4-[4-(4-Fluorophenoxy)phenyl]-pyrimidine-2-carboxylic acid methylamide;
4-[4-(4-Fluorophenoxy)phenyl]-pyrimidine-2-carboxylic acid dimethylamide;
4-[4-(4-Fluorophenoxy)phenyl]-pyrimidine-2-carboxylic acid tert-butylamide;
4-[4-(4-Trifluoromethylphenoxy)phenyl]-pyrimidine-2-carboxamide;
4-[4-(2,4-Difluorophenoxy)phenyl]-pyrimidine-2-carboxamide; and
4-[4-(4-Nitrophenoxy)phenyl]-pyrimidine-2-carboxamide.

Further, the following compounds can be prepared similarly:
4-[4-(4-methoxyphenoxy)phenyl]pyrimidine-2-carboxamide;
4-[4-(3-chloro-2-cyanophenoxy)phenyl]pyrimidine-2-carboxamide; and
4-[4-(4-fluorophenoxy)-3-fluorophenyl]pyrimidine-2-carboxamide.

EXAMPLE 2

2-Methanesulfonyl-4-[4-(4-fluorophenoxy)phenyl] pyrimidine a) 2-Thiomethyl-4-[4-(4-fluorophenoxy)phenyl] pyrimidine: A mixture of 3-dimethylamino-1-[4-(4-fluorophenoxy)phenyl]-propenone (551 mg, 1.93 mmol) and thiourea (294 mg, 3.86 mmol) suspended in 5 mL of ethanol was treated with 1.6 mL (1.93 mmol) of a stock solution prepared from 382 mg of 85% KOH in 5 mL of ethanol added dropwise via syringe. The resulting solution was heated at reflux for 4 hours. Once at room temperature, the yellow precipitate (348 mg) that formed was isolated by filtration and washed with ethanol (2 mL). The solid (338 mg) was then suspended in 5 mL of water and 0.25 mL (2.6 mmol) of dimethyl sulfate was added. After 5 minutes, 1.6 mL of a 2N aqueous NaOH solution was added. After stirring overnight, the mixture was extracted with ether (3×15 mL). The organic layers were pooled, washed with water and brine, dried (Na$_2$SO$_4$) and concentrated. Flash chromatography (silica gel; 3:1 hexane/ethyl acetate) afforded 226 mg of the thiol as an off-white solid. $^1$H NMR (CDCl$_3$) δ 8.51 (d, 1H, J=5.1 Hz), 8.08 (d, 2H, J=8.8 Hz), 7.31 (d, 1H, J=5.5 Hz), 7.11–7.00 (m, 6H), 2.64 (s, 3H).

b) 2-Methanesulfonyl-4-[4-(4-fluorophenoxy)phenyl] pyrimidine: A solution of 205 mg, (0.656 mmol) of 2-thiomethyl-4-[4-(4-fluorophenoxy)phenyl]pyrimidine in 8 mL of CH$_2$Cl$_2$ was treated with a solution of 321 mg of m-chloroperoxybenzoic acid (57–86%) in CH$_2$Cl$_2$ (2 mL). After stirring for 2 hours at room temperature, the reaction was extracted with 20 mL each of water, a 5% aqueous sodium hydrogen sulfite solution, water and brine. After drying (Na$_2$SO$_4$), the solvent was removed in vacuo and the residue was purified by flash chromatography (silica gel; 3:1 EtOAc/hexane) affording 183 mg (81%) of the title compound as a white solid, mp 146°–147° C. $^1$H NMR (CDCl$_3$) δ 8.90 (d, 1H, J=5.5 Hz), 8.19 (d, 2H, J 8.8 Hz), 7.87 (d, 1H, J=5.5 Hz), 7.13–7.09 (m, 6H), 3.45 (s, 3H).

EXAMPLE 3

1-[4-[4-(4-Fluorophenoxy)phenyl]-pyrimidine-2-yl]-ethanone a) 4-[4-(4-Fluorophenoxy)phenyl]-pyrimidine-2-carboxylic acid ethyl ester: A mixture of 4-[4-(4-fluorophenoxy)phenyl]-pyrimidine-2-carboxylic acid (3.15 g, 10.2 mmol), iodoethane (2.0 mL, 25 mmol), and cesium carbonate (7.00 g, 21.5 mmol) in DMF (100 mL) was maintained at 70°–80° C. for 16 hours. The mixture was then partitioned between water and ethyl acetate. The aqueous layer was extracted twice with ethyl acetate. The combined organic layers were washed 3 times with water, dried over sodium sulfate, filtered, and evaporated under reduced pressure to give an oil. Purification by column chromatography (1:1 hexane/ethyl acetate) afforded the desired product (2.14 g, 62%) as an oil which solidified upon standing at room temperature overnight, mp 61°–63° C. $^1$H NMR (CDCl$_3$): δ 8.88 (d, J=5.4 Hz, 1H), 8.16 (d, J=8.7 Hz, 2H), 7.77 (d, J=5.4 Hz, 1H), 7.12–7.05 (m, 6H), 4.55 (q, J=7.5 Hz, 2H), 1.49 (t, J=7.5 Hz, 3H).

b) 1-[4-[4-(4-Fluorophenoxy)phenyl]-pyrimidine-2-yl]-ethanone: To a solution of 4-[4-(4-fluorophenoxy)phenyl]-pyrimidine-2-carboxylic acid ethyl ester (0.66 g, 1.95 mmol) in anhydrous THF (20 mL) at −78° C. under nitrogen was added a 1.4 M solution of methyl magnesium bromide in ether (1.4 mL, 1.96 mmol) in one portion. The reaction was stirred at −78° C. for 30 minutes, quenched with water and partitioned between water and ethyl acetate. The aqueous layer was extracted with ethyl acetate and the combined organic layers were dried over sodium sulfate, filtered, and evaporated under reduced pressure to give a solid. The crude product was then subjected to column chromatography (6:4 hexane/ethyl acetate) affording 0.36 g (60%) of the desired product as a solid. $^1$H NMR (CDCl$_3$): δ 8.90 (d, J=4.2 Hz, 1H), 8.16 (d, J=8.4 Hz, 2H), 7.76 (d, J=4.8 Hz, 1H), 7.09–7.06 (m, 6H), 2.85 (s, 3H).

EXAMPLE 4

2-[4-(4-Chloro-2-fluorophenoxy)phenyl]pyrimidine-4-carboxamide a) 4-(4-Chloro-2-fluorophenoxy)benzonitrile: A mixture of 4-fluorobenzonitrile (5.0 g, 41.3 mmol), 4-chloro-2-fluorophenol (4.7 mL, 44 mmol), and potassium carbonate (13.8 g, 99.8 mmol) in DMF (100 ml) was refluxed overnight. After cooling to room temperature, the mixture was diluted with ethyl acetate, washed twice with a 2N aqueous sodium hydroxide solution, washed with water, dried over sodium sulfate, filtered, and evaporated under reduced pressure to give very light yellow solid. The weight of crude product was 7.56 g (74%). $^1$H NMR (CDCl$_3$): δ 7.61 (d, J=8.1 Hz, 2H), 7.27–7.07 (m, 3H), 6.98 (d, J=8.7 Hz, 2H).

b) 2-[4-(4-Chloro-2-fluorophenoxy)phenyl]-4-methyl-pyrimidine: Hydrogen chloride gas was bubbled through a solution of 4-(4-chloro-2-fluorophenoxy)benzonitrile (1.64 g, 6.64 mmol) in ethanol (100 mL) under N$_2$ at 0° C. for 15 minutes. The solution was stoppered, and stirred at room temperature for 24 hours and concentrated to dryness. The residue was dissolved in ethanol (100 mL), ammonium carbonate (6.3 g, 65 mmol) was added and the resulting mixture was stirred at room temperature for 24 hours. The mixture was filtered and the filtrate was evaporated under reduced pressure to give a white solid. The crude intermediate was not purified, and was carried on to the next step. $^1$H NMR (DMSO-d$_6$): δ 7.90 (d, J=8.4, 2H), 7.40–7.25 (m, 3H), 7.18 (d, J=8.4, 2H).

A mixture of the crude amidine and potassium tert-butoxide (0.72 g, 6.1 mmol) in methanol (100 mL) was refluxed for 30 minutes. Acetylacetaldehyde dimethyl acetal (AADDA; 0.8 mL, 5.4 mmol) was added and the reaction was heated at reflux overnight. Additional potassium tert-butoxide (0.72 g, 6.1 mmol) and AADDA (0.8 mL, 5.4 mmol) were added. After 6 hours at reflux, the reaction was allowed to cool to room temperature and partitioned between water and ethyl acetate. The aqueous layer was extracted once with ethyl acetate. The combined organic layers were dried with sodium sulfate, filtered, and evaporated under reduced pressure to give a dark brown solid. Column chromatography (85/15 hexane/ethyl acetate to 8/2 hexane/ethyl acetate) afforded 0.90 g (43% yield from the benzonitrile) of the desired product as solid. $^1$H NMR (CDCl$_3$): δ 8.60 (d, J=5.1 Hz, 1H), 8.42 (d, J=8.4 Hz, 2H), 7.24–7.02 (m, 6H), 2.56 (s, 3H).

c) 2-[4-(4-Chloro-2-fluorophenoxy)phenyl]pyrimidine-4-carboxylic acid: A mixture of 2-[4-(4-chloro-2-fluorophenoxy)phenyl]-4-methyl-pyrimidine (0.90 g, 2.87 mmol), and selenium dioxide (0.62 g, 5.6 mmol) in pyridine (50 mL) was refluxed overnight. The mixture was allowed to cool to room temperature, then filtered through a bed of Celite. The filtrate was evaporated under reduced pressure. The residue was dissolved in ethyl acetate, and washed twice with a 2N aqueous hydrochloric acid solution. The organic layer was separated, dried over sodium sulfate, filtered, and evaporated under reduced pressure to give 0.808 g (82%) of a light yellow solid. $^1$H NMR (DMSO-d$_6$): δ 9.11 (d, J=5.1 Hz, 1H), 8.46 (d, J=8.7 Hz, 2H), 7.87 (d, J=4.5 Hz, 1H), 7.38–7.35 (m, 3H), 7.15 (d, J=9.0 Hz, 2H)

d) 2-[4-(4-Chloro-2-fluorophenoxy)phenyl]pyrimidine-4-carboxamide: A solution of 2-[4-(4-chloro-2-fluorophenoxy)phenyl]-pyrimidine-4-carboxylic acid (0.6 g, 1.74 mmol), and carbonyl diimidazole (0.54 g, 3.3 mmol) in DMF (20 mL) was stirred at room temperature under nitrogen for 30 minutes. Solid ammonium acetate (2.0 g, 26 mmol) was added and the reaction was stirred overnight. The reaction was then diluted with ethyl acetate, washed 3 times with water, dried over sodium sulfate, filtered, and evaporated under reduced pressure to give a yellow solid. The crude product was purified by column chromatography (4:1 dichloromethane/ethyl acetate) to give 331 mg (55%) of the final product as a white solid, mp 198°-200° C. $^1$H NMR (CDCl$_3$): δ 9.01 (d, J=4.8 Hz, 1H), 8.44 (d, J=8.4 Hz, 2H), 7.96 (d, J=4.2 Hz, 1H), 7.88 (bs, 1H), 7.26–7.23 (m, 1H), 7.16–7.10 (m, 2H), 7.06 (d, J=8.7 Hz, 2H), 5.75 (bs, 1H).

The following compound was prepared similarly: 2-[4-(4-Chloro-2-fluorophenoxy)phenyl]pyrimidine-4-carboxylic acid methylamide.

EXAMPLE 5

2-Chloropyrimidine-4-carboxamide a) 2-Hydroxy-4-pyrimidinecarboxaldehyde, oxime: A solution of 4-methyl-2-pyrimidinol hydrochloride (14.7 g, 0.100 mol) in 100 mL of 50% aqueous HOAc at 12° C. was treated with solid NaNO$_2$ (10.47 g, 0.150 mol) added in one portion. Brown gas evolved and a yellow precipitate formed as the reaction temperature rose to 42° C. After stirring at room temperature for 3 hours, the solid precipitate was isolated by filtration and washed with cold water (2×50 mL). The resulting solid was recrystallized from 550 mL of boiling water, affording 11.9 g (85%) of the oxime as yellow-brown needles, mp 222°–226° C. (decomp.). $^1$H NMR (DMSO-d$_6$): δ 12.4 (brs, 1H), 11.9 (br s, 1H), 7.95 (d, J=6.3 Hz, 1H), 7.79 (s, 1H), 6.68 (d, 1H, J=6.6 Hz).

b) 2-Chloro-4-cyanopyrimidine: To neat POCl$_3$ (40 mL, 65.8 g, 0.429 mol) cooled in an ice-water bath was added powdered solid 2-hydroxy-4-pyrimidinecarboxaldehyde, oxime (10.0 g, 71.9 mmol) in portions. The cold bath was removed and the mixture was slowly heated to reflux. When the reaction began to reflux on its own, heating was stopped. Once the reflux had subsided, neat N,N-dimethylaniline (5 mL, 4.78 g, 39.4 mmol) was added via syringe. The resulting dark solution was heated at reflux for 30 minutes. Once at room temperature, the reaction was slowly added to 300 g of crushed ice. The resulting dark mixture was extracted with ether (4×100 mL). The pooled ether layers were then washed with water (2×50 mL), a sat. aqueous NaHCO$_3$ solution (2×50 mL) and water (2×50 mL). After drying (Na$_2$SO$_4$) the mixture was filtered and concentrated in vacuo. 1.5 g of the resulting red oil was dissolved in a min. of CH$_2$Cl$_2$ and added to 15 cm of flash silica in a 4 cm. diameter column. Elution with 100% gave 1.4 g of a yellow solid. The remainder of the red oil (3.6 g) was chromatographed on silica gel, afforded a total of 4.72 g (47%) of the nitrile as a yellow solid, mp 49.5°–52° C. $^1$H NMR (CDCl$_3$): δ 8.89 (d, 1H, J=4.8 Hz), 7.62 (d, 1H, J=4.8 Hz).

c) 2-Chloropyrimidine-4-carboxamide: To 15 mL of concentrated H$_2$SO$_4$ at 15° C. was added finely ground 2-chloro-4-cyanopyrimidine (4.0 g, 28.7 mmol). The mixture that formed was allowed to warm to room temperature and stirred for 5 hours. The resulting light yellow solution was then slowly added to 80 g of crushed ice. The mixture was filtered, washed with cold water (2×25 mL) and a saturated aqueous NaHCO$_3$ solution (25 mL), to give 490 mg of the amide as a yellow solid, mp 151°–152° C. The mother liquor was extracted with EtOAc (3×50 mL). The pooled organic layers were washed with water (25 mL) and a saturated aqueous NaHCO$_3$ solution (2×25 mL). After drying (Na$_2$SO$_4$), the EtOAc was removed in vacuo, affording an additional 2.5 g of the amide as a yellow solid. Total yield of the title compound was 2.99 g (66%). $^1$H NMR (CDCl$_3$): δ 8.88 (d, 1H, J=4.8 Hz), 8.07 (d, 1H, J=4.8 Hz), 7.65 (br s, 1H), 5.93 (br s, 1H).

EXAMPLE 6

6-[(4-Trifluoromethoxy)phenyl]pyridine-2-carboxamide a) 6-Bromopyridine-2-carboxamide: Reaction of 6-bromopicolinic acid (Aldrich) with carbonyl diimidazole in DMF followed by the addition of an excess of ammonium acetate was carried out as described above, affording the amide as a white solid, mp 130°–135° C. $^1$H NMR (CDCl$_3$): δ 8.17 (d, 1H, J=7.5 Hz), 7.73 (t, 1H, J=7.8 Hz), 7.64 (d, 1H, J=7.5 Hz), 5.66 (br s, 1H).

b) 6-[(4-Trifluoromethoxy)phenyl]pyridine-2-carboxamide: A mixture of 6-bromopyridine-2-carboxamide (110 mg, 0.547 mmol), 4-(trifluoromethoxy)phenylboronic acid (Aldrich; 138 mg, 0.670 mmol), sodium carbonate (185 mg) and Pd(PPh$_3$)$_4$ (32 mg, 5 mol %) in 10 mL of toluene and 2.5 mL each of water and EtOH was heated at reflux overnight. After cooling to room temperature, the mixture was partitioned between water and EtOAc. The aqueous layer was washed twice with EtOAc and the pooled organic layers were washed with water (3×), dried (Na$_2$SO$_4$), filtered and concentrated to dryness. Flash chromatography (6:4 hexane/acetone) afforded 122 mg (79%) of the title compound as a white solid, mp 133°–135° C. $^1$H NMR (CDCl$_3$): δ 8.19 (d, J=7.5 Hz, 1H), 8.04 (d, J=9.0 Hz, 2H), 7.96 (t, J=7.8 Hz, 1H), 7.94 (bs, 1H), 7.87 (d, J=7.8 Hz, 1H), 7.35 (d, J=8.1 Hz, 2H), 5.76 (bs, 1H).

EXAMPLE 7

3-Dimethylamino-1-{4-[4-(4-fluorophenoxy)phenyl]pyrimidin-2-yl}propenone

A solution of 1-{4-[4-(4-fluorophenoxy)phenyl]pyrimidin-2-yl}ethanone (0.36 g, 1.17 mmol) and N,N-dimethylformamide dimethyl acetal (94%, 0.25 mL, 1.77 mmol) in DMF (10 mL) was refluxed for several hours. The reaction was cooled to room temperature, then partitioned between ethyl acetate (50 mL) and water (50 mL). The aqueous layer was extracted with ethyl acetate (2×50 mL). The combined organic layers were washed with water (3×50 mL), dried over sodium sulfate, filtered, and evaporated under reduced pressure to give an oil. The oil was purified by column chromatography (100% ethyl acetate to 8:2 ethyl acetate/methanol) to give 182 mg (43% yield) of the final product as a brownish yellow solid, mp 151°-153° C. $^1$H NMR (CDCl$_3$): δ 8.87 (d, J=5.1 Hz, 1H), 8.16 (d, J=9.0 Hz, 2H), 7.98 (d, J=12.9 Hz, 1H), 7.67 (d, J 5.4 Hz, 1H), 7.11–7.05 (m, 6H), 6.43 (bd, 1H), 3.19 (s, 3H), 3.00 (s, 3H).

EXAMPLE 8

4-[4-(4-Fluorophenoxy)phenyl]pyrimidine-2-carboxylic acid, (2-hydroxyethyl)amide To a mixture of 4-[4-(4-fluorophenoxy)phenyl]pyrimidine-2-carboxylic acid (1.03 g, 3.1 mmol), ethanolamine (0.31 mL, 5.08 mmol), and 1-hydroxybenzotriazol hydrate (0.53 g, 3.46 mmol) in DMF (20 mL) under nitrogen at 0° C. was added 4-methylmorpholine (0.76 mL, 6.9 mmol), and 1-[3-(dimethylamino)propyl]-3-ethyl carbodiimide hydrochloride (0.68 g, 3.48 mmol). The mixture was allowed to warm to room temperature overnight. The reaction was diluted with ethyl acetate, washed 3 times with water, dried over sodium sulfate, filtered, and evaporated under reduced pressure to give the desired product as an oil. $^1$H NMR (CDCl$_3$): δ 8.82 (d, J=5.7 Hz, 1H), 8.50 (bs, 1H), 8.10 (d, J=8.7 Hz, 2H), 7.71 (d, J=5.1 Hz, 1H), 7.08–7.03 (m, 6H), 3.88 (t, J=4.2 Hz, 2H), 3.70 (q, J=4.8 Hz, 2H), 3.25 (bs, 1H).

EXAMPLE 9

6-(4-Phenoxyphenyl)pyridine-2-carboxylic Acid Methylamide

6-Bromopicolinic acid (Aldrich) was coupled with methyl amine using carbonyl diimidazole (CDI) as coupling reagent to afford 6-bromopyridine-2-carboxylic acid methylamide. The 6-bromopyridine-2-carboxylic acid methylamide underwent Suzuki coupling with 4-phenoxyphenylboronic acid, in the presence of tetrakis(triphenylphosphine)palladium as catalyst to give 6-(4-phenoxyphenyl)pyridine-2-carboxylic acid methylamide as a solid. $^1$H NMR (CDCl$_3$): δ 8.12 (d, J=7.8 Hz, 1H), 7.98 (d, J=8.7 Hz, 2H), 7.90 (t, J=7.8 Hz, 1H), 7.81 (d, J=7.8 Hz, 1H), 7.38 (t, J=8.4 Hz, 2H), 7.18–7.06 (m, 5H), 3.08 (d, J=5.4 Hz, 3H).

EXAMPLE 10

6-[4-(4-Fluorophenoxy)phenyl]pyridine-2-carboxamide a) 2-Methyl-6-(4-bromophenyl)pyridine: To a mixture of 4-bromophenylboronic acid (3.14 g, 15.6 mmol), 2-bromo-6-methylpyridine (1.7 ml, 14.9 mmol), solid sodium carbonate (5.1 g, 31.9 mmol) in toluene (60 mL), water (15 mL), and ethanol (15 mL) was added tetrakis (triphenylphosphine)palladium (0) (890 mg, 0.77 mmol). The mixture was refluxed (100°–110° C.) overnight. The reaction was allowed to cool to room temperature, then partitioned between ethyl acetate and water. The aqueous layer was extracted one more time with ethyl acetate. The combined organic layers were dried over sodium sulfate, filtered, and evaporated under reduced pressure to give the crude product. Purification by flash chromatography (silica gel; 4% EtOAc/hexane) afforded 2.5 g (87%) of the product as a white solid. $^1$H NMR (CDCl$_3$): δ 7.88 (d, J=9.0 Hz, 2H), 7.67–7.56 (m, 3H), 7.48 (d, J=8.1 Hz, 1H), 7.11 (d, J=8.1 Hz, 1H), 2.61 (s, 3H).

b) 2-Methyl-6-[4-(4-fluorophenoxy)phenyl]pyridine: A mixture of 2-methyl-6-(4-bromophenyl)pyridine (3.25 g, 13 mmol), 4-fluorophenol (2.5 g, 22 mmol), cesium carbonate (11.2 g, 34 mmol), and copper powder (4.5 g) in DMF (50 mL) was refluxed overnight. The reaction was allowed to cool to room temperature, filtered and partitioned between ethyl acetate and water. The aqueous layer was extracted two times with ethyl acetate. The combined organic layers were washed three times with water, dried over sodium sulfate, filtered, and evaporated under reduced pressure to give a solid that was subjected to flash chromatography (silica gel; 4% EtOAc/hexane) to give 1.8 g (50%) of the product as a white solid. $^1$H NMR (CDCl$_3$): δ 7.94 (d, J=9.0 Hz, 2H), 7.61 (t, J=7.6 Hz, 1H), 7.46 (d, J=8.1 Hz, 1H), 7.08–7.01 (m, 7H), 2.61 (s, 3H).

c) 6-[4-(4-Fluorophenoxy)phenyl]pyridine-2-carboxamide: A mixture of 2 methyl-6-[4-(4-fluorophenoxy)phenyl]pyridine (1.8 g, 6.45 mmol), and selenium dioxide (3.6 g, 32.4 mmol) in pyridine (30 mL) was heated at reflux overnight. Once at room temperature, the reaction was filtered through Celite. The filtrate was partitioned between ethyl acetate and an aqueous hydrochloric acid solution (2N). The aqueous layer was extracted two more times with ethyl acetate. The combined organic layers were washed with an aqueous hydrochloric acid solution (2N), dried over sodium sulfate, filtered, and evaporated under reduced pressure to give 1.8 g (90%) of the crude acid as a yellow solid. The crude acid (1.2 g, 3.88 mmol) was dissolved in DMF (50 mL) and carbonyl diimidazole (1.3 g, 8.0 mmol) was added. The resulting solution was stirred at room temperature for 1 hour. Solid ammonium acetate (3.1 g, 39 mmol) was added and the mixture was stirred overnight. The reaction was partitioned between ethyl acetate and water. The aqueous layer was extracted two times with ethyl acetate. The combined organic layers were washed three times with water, dried over sodium sulfate, filtered, and evaporated under reduced pressure to give the crude product.

Purification by flash chromatography (silica gel column; 65/35 hexane/acetone) afforded 509 mg (42%) of the title compound, mp 150°–152° C. $^1$H NMR (DMSO-d$_6$): δ 8.32 (d, J=9.0 Hz, 2H), 8.31 (bs, 1H), 8.12 (d, J=8.1 Hz, 1H), 8.03 (dd, J=8.1, 7.2 Hz, 1H), 7.94 (d, J=7.2 Hz, 1H), 7.69 (bs, 1H), 7.27 (t, J=9.0 Hz, 2H), 7.18–7.13 (m, 2H), 7.07 (d, J=9.0, 2H).

The following compounds can be prepared similarly:
6-[4-(2,4-difluorophenoxy)phenyl]pyridine-2-carboxamide;
6-[4-(4-chloro-2-fluorophenoxy)phenyl]pyridine-2-carboxamide;
6-[4-(4-fluorophenoxy)-3-fluorophenyl]pyridine-2-carboxamide; and
6-[4-(4-trifluoromethylphenoxy)phenyl]pyridine-2-carboxamide.

EXAMPLE 11

6-(4-Phenoxyphenyl)pyridine-2-carboxamide 6-(4-Phenoxyphenyl)pyridine-2-carboxamide was prepared by the method used for its 4-fluoro analog in Example 10, except 4-phenoxyphenylboronic acid (Aldrich) was used in place of 4-bromophenylboronic acid.

a) 2-Methyl-6-(4-phenoxyphenyl)pyridine: $^1$H NMR (CDCl$_3$): δ 7.95 (d, J=9.0 Hz, 2H), 7.60 (t, J=7.5 Hz, 1H), 7.46 (d, J=7.5 Hz, 1H), 7.34 (t, J=7.8 Hz, 2H), 7.13–7.02 (m, 6H), 2.61 (s, 3H).

b) 6-(4-Phenoxyphenyl)pyridine-2-carboxylic acid: $^1$H NMR (DMSO-d$_6$): δ 13.1 (bs, 1H), 8.21 (d, J=8.4 Hz, 2H), 8.16 (d, J=7.8 Hz, 1H), 8.04 (t, J=7.2 Hz, 1H), 7.96 (d, J=7.2 Hz, 1H), 7.44 (t, J=7.6 Hz, 2H), 7.19 (t, J=7.4 Hz, 1H), 7.11 (dd, J=8.4, 7.5 Hz, 4H).

c) 6-(4-Phenoxyphenyl)pyridine-2-carboxamide: $^1$H NMR (DMSO-d$_6$): δ 8.33 (d, J=8.7 Hz, 2H), 8.31 (bs, 1H), 8.12 (d, J=7.8 Hz, 1H), 8.03 (t, J=7.6 Hz, 1H), 7.94 (d, J=7.8 Hz, 1H), 7.69 (bs, 1H), 7.43 (dd, J=8.7, 7.5 Hz, 2H), 7.19 (t, J=7.8 Hz, 1H), 7.09 (d, J=8.7 Hz, 4H), mp 178°-180° C., 45% yield from starting materials (3 steps).

EXAMPLE 12

2-[4-(4-Fluorophenoxy)phenyl]pyrimidine-4-carboxamide a) 4-(4-Fluorophenoxy)benzonitrile: A mixture of 4-fluorophenol (5.1 g, 45.5 mmol), 4-fluorobenzonitrile (4.58 g, 37.8 mmol) and potassium carbonate (12 g, 86.8 mmol) in DMF (150 mL) was refluxed overnight. The reaction was allowed to cool to room temperature and partitioned between ethyl acetate and water. The aqueous layer was extracted twice with ethyl acetate. The combined organic layers were washed three times with water, dried over sodium sulfate, filtered, and evaporated under reduced pressure to give 7.5 g (93%) of crude 4-(4-fluorophenoxy) benzonitrile as solid. $^1$H NMR (CDCl$_3$): δ 7.60 (d, J=9.0 Hz, 2H), 7.10–6.96 (m, 6H). Ref. Tanaka, A. et al. (*J. Med. Chem.* 41:4408–4420 (1998))

b) 4-(4-Fluorophenoxy)benzamidine acetate: 4-(4-Fluorophenoxy)benzonitrile (4.7 g, 22.4 mmol) was dissolved in ethanol. The solution was cooled to 0° C. and HCl gas was bubbled through the solution for 20 minutes. The reaction was stoppered and stirred at room temperature overnight. The solution was evaporated under reduced pressure and the solid residue that formed was dissolved in ethanol and treated with solid ammonium acetate (6.0 g, 75.5 mol). After stirring overnight, pure amidine was isolated by filtration. Additional product was isolated from the filtrate. The solid obtained after the filtrate was concentrated to dryness was triturated with hexane (4 times) and recrystallized twice from EtOH. The total weight of amidine obtained was 2.92 g (45% yield). $^1$H NMR (DMSO-d$_6$): δ 7.85 (d, J=8.0 Hz, 2H), 7.31 (t, J=8.7 Hz, 2H), 7.21–7.17 (m, 2H), 7.11 (d, J=8.0 Hz, 2H), 1.77 (s, 3H).

c) 2-[4-(4-Fluorophenoxy)phenyl]-4-methylpyrimidine: A 1M solution of potassium tert-butoxide in THF (11 mL, 11 mmol) was added via syringe to a solution of 4-(4-fluorophenoxy)benzamidine acetate (2.92 g, 10.2 mmol) in DMF. The resulting mixture was heated at 100° C. for 2 hours. Acetylacetaldehyde dimethyl acetal (2 mL, 13.6 mmol) was added via syringe. The reaction was maintained between 100°–110° C. overnight when TLC indicated complete reaction. The reaction was allowed to cool to room temperature and partitioned between water and EtOAc. The aqueous layer was extracted with EtOAc and the combined organic layers were washed with water (3 times), dried over MgSO$_4$, filtered, and evaporated under reduced pressure to give the desired product as a yellow oil. $^1$H NMR (CDCl$_3$): δ8.60 (d, J=5.1, 1H), 8.40 (d, J=9.0, 2H), 7.05–7.00 (m, 7H), 2.57 (s, 3H). This material was carried on without further purification.

d) 2-[4-(4-Fluorophenoxy)phenyl]pyrimidine-4-carboxylic acid: A mixture of 2-[4-(4-fluorophenoxy) phenyl]-4-methylpyrimidine (yellow oil from previous step), selenium dioxide (3.0 g, 27 mmol) and pyridine (30 mL) was refluxed overnight. The reaction was allowed to cool to room temperature and filtered to remove selenium metal. The filtrate was evaporated under reduced pressure and the residue was treated with an aqueous 2N HCl solution. The resulting solid was triturated with hexane (3x) and dried in vacuo, affording 2.72 g (86%) of the acid. $^1$H NMR (DMSO-d$_6$): δ 13.8 (bs, 1H), 9.10 (d, J=5.0 Hz, 1H), 8.45 (d, J=9.0 Hz, 2H), 7.86 (d, J=5.0Hz, 1H), 7.30 (t, J 9.0Hz, 2H), 7.22–7.17 (m, 2H), 7.11 (d, J=9.0Hz, 2H).

e) 2-[4-(4-Fluorophenoxy)phenyl]pyrimidine-4-carboxamide: To a solution of 2-[4-(4-fluorophenoxy) phenyl]pyrimidine-4-carboxylic acid (2.00 g, 6.45 mmol) in DMF was added carbonyl diimidazole (2.00 g, 12.3 mmol). After stirring at room temperature for 1 hour, solid ammonium acetate (5.00 g, 62.9 mmol) was added. After stirring overnight at room temperature, the reaction was partitioned between water and EtOAc. The aqueous layer was extracted with ethyl acetate and the pooled organic layers were washed with water (3 times), dried (Na$_2$SO$_4$), filtered, and evaporated under reduced pressure to give the crude product as solid. Column chromatography (silica gel) afforded 1.1 g (55%) of the desired product as a light tan solid (99.80% pure by HPLC), mp 195°–197° C. $^1$H NMR (CDCl$_3$): δ 9.01 (d, J=4.8 Hz, 1H), 8.43 (d, J=8.7 Hz, 2H), 7.95 (d, J=4.8 Hz, 1H), 7.89 (bs, 1H), 7.08–7.04 (m, 6H), 5.72 (bs, 1H).

The following compound can be prepared similarly:
2-[4-(4-fluorophenoxy)-3-fluorophenyl]pyrimidine-4-carboxamide; EXAMPLE 13

3,5-Diamino-6-(4-phenoxyphenyl)pyrazine-2-carboxamide

To a mixture of 4-phenoxyphenylboronic acid (0.22 g, 1.02 mmol), 3,5-diamino-6-chloropyrazine-2-carboxamide (0.176 g, 0.919 mmol), sodium carbonate (0.33 g, 2.06 mmol) in toluene (14 mL), ethanol (3.5 mL), and water (3.5 mL) was added tetrakis(triphenylphosphine)palladium (60 mg). The mixture was refluxed overnight. The reaction was allowed to cool to room temperature, then partitioned between water and ethyl acetate. The aqueous layer was extracted one more time with ethyl acetate. The combined organic layers were washed with water, dried over sodium sulfate, filtered, and evaporated under reduced pressure to give the crude product as a solid. Flash chromatography (Silica gel; 6:4 ethyl acetate/dichloromethane to 7:3 ethyl acetate/dichloromethane) and subsequent recrystalization from chloroform afforded 81 mg (27%) of the desired product as white solid. $^1$H NMR (CDCl$_3$): δ 7.58 (d, J=9.0 Hz, 2H), 7.37 (t, J=7.8 Hz, 2H), 7.38 (bs, 1H), 7.15 (t, J=8.4 Hz, 1H), 7.10–7.05 (m, 4H), 5.26 (bs, 1H), 4.97 (s, 4H).

EXAMPLE 14

6-(4-Phenoxyphenyl)pyrazine-2-carboxamide a) 2-Chloro-6-(4-phenoxyphenyl)pyrazine: A mixture of 4-phenoxyphenylboronic acid (0.54 g, 2.52 mmol), 2,6-dichloropyrazine (1.28 g, 7.73 mmol), sodium carbonate (1.15 g, 7.18 mmol), and tetrakis(triphenylphosphine)palladium (0.15 g, 0.13 mmol) in toluene (50 mL), ethanol (12 mL), and water (12 mL) was heated at reflux overnight. The reaction was allowed to cool to room temperature, then partitioned between water and ethyl acetate. The aqueous layer was extracted one more time with ethyl acetate. The combined organic layers were washed with water, dried over sodium sulfate, filtered, and evaporated under reduced pressure to give crude product as a solid. Purification by column chromatography gave 0.49 g (69%) of 2-chloro-6-(4-phenoxyphenyl)pyrazine as a solid. $^1$H NMR (CDCl$_3$): δ 8.87 (s, 1H), 8.47 (s, 1H), 7.99 (d, J=9.0 Hz, 2H), 7.38 (t, J=8.1 Hz, 2H), 7.15 (t, J=7.2 Hz, 1H), 7.12–7.06 (m, 4H).

b) 6-(4-Phenoxyphenyl)pyrazine-2-carboxamide: A mixture of 2-chloro-6-(4-phenoxyphenyl)pyrazine (0.49 g, 1.73 mmol), potassium cyanide (98%, 0.30 g, 4.51 mmol), and tetrakis(triphenylphosphine)palladium (0.10 g, 0.086 mmol) in DMF was refluxed overnight. Workup as described as above and column chromatography gave 35 mg (7%) of 6-(4-phenoxyphenyl)pyrazine-2-carboxamide as a solid. $^1$H NMR (CDCl$_3$): δ 9.30 (s, 1H), 9.16 (s, 1H), 8.01 (d, J=8.7 Hz, 2H), 7.75 (bs, 1H), 7.40 (t, J=8.4 Hz, 2H), 7.21–7.08 (m, 5H), 5.84 (bs, 1H).

EXAMPLE 15

2-[4-(4-Nitrophenoxy)phenyl]-4-methyl-[1,3,5] triazine a) N-Dimethylaminomethylene-4-(4-nitrophenoxy)benzamide: A solution of 4-(4-nitrophenoxy)benzonitrile (0.90 g, 3.75 mmol), potassium hydroxide (2.0 g, 30 mmol) in water (10 mL), a 30% aqueous hydrogen peroxide solution (4 mL, 39 mmol) and ethanol (50 mL) was refluxed for several hours. The reaction was allowed to cool to room temperature, then partitioned between water and ethyl acetate. The separated organic layer was washed several times with water, dried over MgSO$_4$, filtered, and evaporated under reduced pressure to give the amide intermediate as a solid. The amide and N,N-dimethylformide dimethyl acetal in DMF (20 mL) were heated to 100°–120° C. for 2 hours. Once at room temperature, water was added and 0.93 g (79%) of the amide was isolated by filtration as a yellow solid. $^1$H NMR (CDCl$_3$): δ 8.66 (s, 1H), 8.34 (d, J=8.7 Hz, 2H), 8.22 (d, J=9.0 Hz, 2H), 7.10 (d, J=9.0 Hz, 2H), 7.06 (d, J=9.0 Hz, 2H), 3.23 (s, 3H), 3.22 (s, 3H).

b) 2-[4-(4-Nitrophenoxy)phenyl]-4-methyl-[1,3,5] triazine: A mixture of N-dimethylaminomethylene-4-(4-nitrophenoxy)benzamide (0.93 g, 2.97 mmol), acetamidine hydrochloride (0.32 g, 3.2 mmol) and potassium tert-butoxide (95%, 0.33 g, 2.79 mmol) in dioxane was refluxed overnight. The reaction was allowed to cool to room temperature, then partitioned between water and ethyl acetate. The aqueous layer was extracted one more time with ethyl acetate. The combined organic layers were washed twice with water, dried over sodium sulfate, filtered, and evaporated under reduced pressure to give the crude product. Purification by column chromatography gave 24 mg (3%) of the title compound as a light yellow solid, mp 148°–149° C. $^1$H NMR (CDCl$_3$): δ 9.08 (s, 1H), 8.59 (d, J=8.1 Hz, 2H), 8.25 (d, J=8.1 Hz, 2H), 7.19 (d, J 9.3 Hz, 2H), 7.11 (d, J 8.4 Hz, 2H), 2.74 (s, 3H).

EXAMPLE 16

6-[4-(4-fluorophenoxy)Phenyl]Pyridine Carboxylic Acid N-piperidinylethylamide (3)

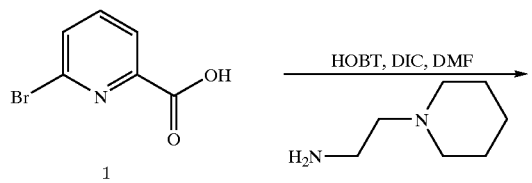

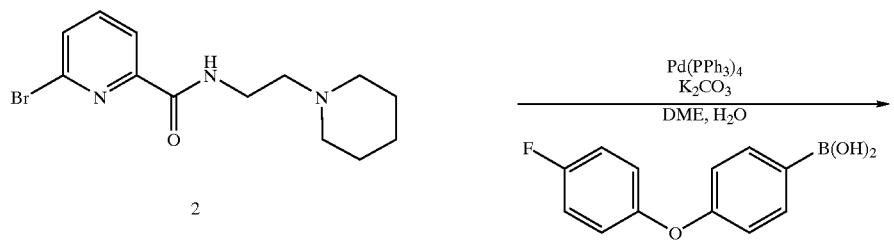

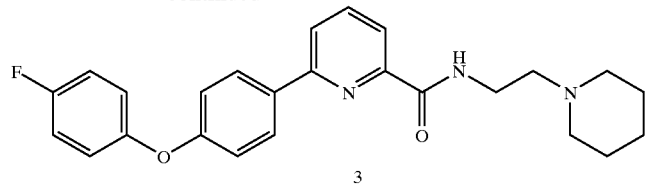

a) 6-Bromopyridine-2-carboxylic acid N-piperidinylethylamide (2): To a solution of 6-bromopicolinic acid (5.0 g, 24.8 mmol) (1) and 1-(2-aminoethyl)-piperidine (3.3 g, 26.0 mmol) in DMF was added N-hydroxybenzotriazole (HOBt) (3.4 g, 24.8 mmol) and 5-(3,4-dimethyl-1-triazenyl)-1H-imidazole-4-carboxamide (DIC) (3.1 g, 24.8 mmol). The reaction was allowed to stir 24 hours at ambient temperature. The reaction was diluted with dichloromethane, and water was then added. The phases were separated, and the aqueous phase was extracted twice with dichloromethane. The combined organic phases were dried over sodium sulfate. The solution was filtered and then concentrated to give the product as a pale-yellow solid. Purification of compound 2 was then carried out by silica gel chromatography.

b) 6-[4-(fluorophenoxy)phenyl]pyridine carboxylic acid N-piperidinylethylamide (3): 4-(4-fluorophenoxy)phenyl boronic acid (557 mg, 2.4 mmol) was added to a solution of compound 2 (624 mg, 2.0 mmol) in 1,2-dimethoxyethane (DME) (6 mL), followed by water (2 mL) and potassium carbonate (746 mg, 5.4 mmol). Pd(PPh$_3$)$_4$ (92 mg, 0.08 mmol) was added to this mixture, and the reaction was heated at 85° C. for 16 hours under an argon atmosphere. The reaction was allowed to cool to ambient temperature, and the phases were separated. The aqueous phase was extracted three times with ethyl acetate, and the combined organic phases were dried over sodium sulfate. The solution was filtered, concentrated, and then filtered over a bed of florisil to give crude compound 3. Purification of compound 3 was then carried out by silica gel chromatography. $^1$H NMR (400 MHz, CDCl$_3$): δ 1.48 (bs, 2H), 1.61–1.67 (m, 4H), 2.48 (bs, 2H), 2.59 (t, 2H, J=6.3 Hz), 7.05–7.07 (m, 5H), 7.64–7.71 (m, 1H), 7.81–7.91 (m, 5H), 8.80 (bs, 1H).

EXAMPLE 17

6-(4-tert-butylphenyl)pyridine-2-carboxamide (8a)

6-(4-n-butylphenyl)pyridine-2-carboxamide (8b)

6-(4-i-propylphenyl)pyridine-2-carboxamide (8c)

6-(4-thiomethylphenyl)pyridine-2-carboxamide (8d)

6-(4-ethoxyphenyl)pyridine-2-carboxamide (8e)

6-(4-methoxyphenyl)pyridine-2-carboxamide (8f)

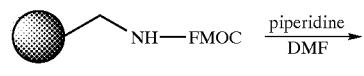

a R = tert-butyl
b R = n-butyl
c R = i-Pr
d R = SMe
e R = OEt
f R = OMe a) Compound 6: 20% piperidine in DMF was added to polystyrene-Rink-amide resin having 9-fluorenylmethoxycarbonyl (FMOC) protective group (PS-rink-NH-FMOC resin) (4) (4.45 g, 4.14 mmol) in a solid-phase reaction vessel, and the reaction was shaken for 1.5 hours at ambient temperature. The resin was washed (DMF twice, dichloromethane twice, DMF) and then treated again with 20% piperidine in DMF. It was shaken for an additional 1 hour, and the washing sequence was repeated. DMF was added to the resin, followed by N-hydroxybenzotriazole (HOBt) (3.4 g, 24.8 mmol), 6-bromopicolinic acid (1, 5.0 g, 24.8 mmol), and a solution of 5-(3,4-dimethyl-1-triazenyl)-1H-imidazole-4-carboxamide (DIC) (3.1 g, 24.8 mmol) in DMF. The mixture was shaken for 24 hours at ambient temperature and then drained. The resin was washed (DMF twice, dichloromethane twice, DMF) and dried. Compound 6 was split into individual reaction vessels.

b) Compounds 7a–7f: 1,2-Dimethoxyethane (DME) (2.5 mL) was added to the individual reaction vessels containing compound 6 (0.25 mmol), followed by the addition of the phenyl boronic acid (1.5 mmol). To this mixture was added water (1.0 mL), potassium carbonate (3.8 mmol), and Pd(PPh$_3$)$_4$ (0.043 mmol). The reactions were heated at 85° C. for 16 hours. After returning to ambient temperature, the reactions were drained, and the resin was washed (1:1 DME-water twice, water, 1:1 DME-water twice, DME twice, water twice, THF twice, dichloromethane twice) to yield 7a–7f.

c) Compounds 8a–8f: Compounds 7a–7f were shaken in the presence of 1:1 trifluoroacetic acid (TFA)-dichloromethane for 1.5 hours. The reactions were filtered, the resins were washed with dichloromethane, and the solvent was then evaporated. Purification of compounds 8a–8f was carried out by first filtering over a bed of florisil followed by subjection to silica gel chromatography.

6-(4-tert-butylphenyl)pyridine-2-carboxamide (8a): $^1$H NMR (400 MHz, CDCl$_3$): δ 1.38 (s, 9H), 5.65 (bs, 1H), 7.55 (d, 2H, J=8.9 Hz), 7.85–7.99 (m, 4H), 8.05 (bs, 1H), 8.15 (d, 1H, J=8.6 Hz).

6-(4-n-butylphenyl)pyridine-2-carboxamide (8b): $^1$H NMR (400 MHz, CDCl$_3$): δ 0.95 (t, 3H, J=7.3 Hz), 1.36–1.42 (m, 2H), 1.61–1.69 (m, 2H), 2.69 (t, 2H, J=7.6 Hz), 5.68 (bs, 1H), 7.32 (d, 2H, J=8.4 Hz), 7.86–7.94 (m, 4H), 8.03 (bs, 1H), 8.13 (d, 1H, J=7.3 Hz).

6-(4-i-propylphenyl)pyridine-2-carboxamide (8c): $^1$H NMR (400 MHz, CDCl$_3$): δ 1.31 (d, 6H, J=6.9 Hz), 2.95–3.02 (m, 1H), 5.65 (bs, 1H), 7.37 (d, 2H, J=8.2 Hz), 7.86–7.95 (m, 4H), 8.05 (bs, 1H), 8.14 (d, 1H, J=7.3 Hz).

6-(4-thiomethylphenyl)pyridine-2-carboxamide (8d): $^1$H NMR (400 MHz, CDCl$_3$): δ 2.56 (s, 3H), 7.38 (d, 2H, J=8.7 Hz), 7.93–8.09 (m, 5H).

6-(4-ethoxyphenyl)pyridine-2-carboxamide (8e): $^1$H NMR (400 MHz, CDCl$_3$): δ 1.46 (t, 3H, J=7.0 Hz), 4.11 (q, 2H, J=6.8 Hz), 7.01 (d, 2H, J=8.9 Hz), 7.82–7.91 (m, 2H), 7.97 (d, 2H, J=8.9 Hz), 8.01 (bs, 1H), 8.10 (d, 1, J=8.6 Hz H).

6-(4-methoxyphenyl)pyridine-2-carboxamide (8f): $^1$H NMR (400 MHz, CDCl$_3$): δ 3.90 (s, 3H), 7.05 (d, 2H, J=8.9 Hz), 7.90–8.05 (m, 5H).

EXAMPLE 18

2-Methyl-4-dimethylamino-6-[4-(4-fluorophenoxy)phenyl]pyridine (14)

4-Methoxy-6-[4-(4-fluorophenoxy)phenyl]pyridine-2-carboxamide (18)

4-Methoxy-6-[4-(4-fluorophenoxy)phenyl]pyridine-2-carboxylic acid dimethylaminoethylamide (19)

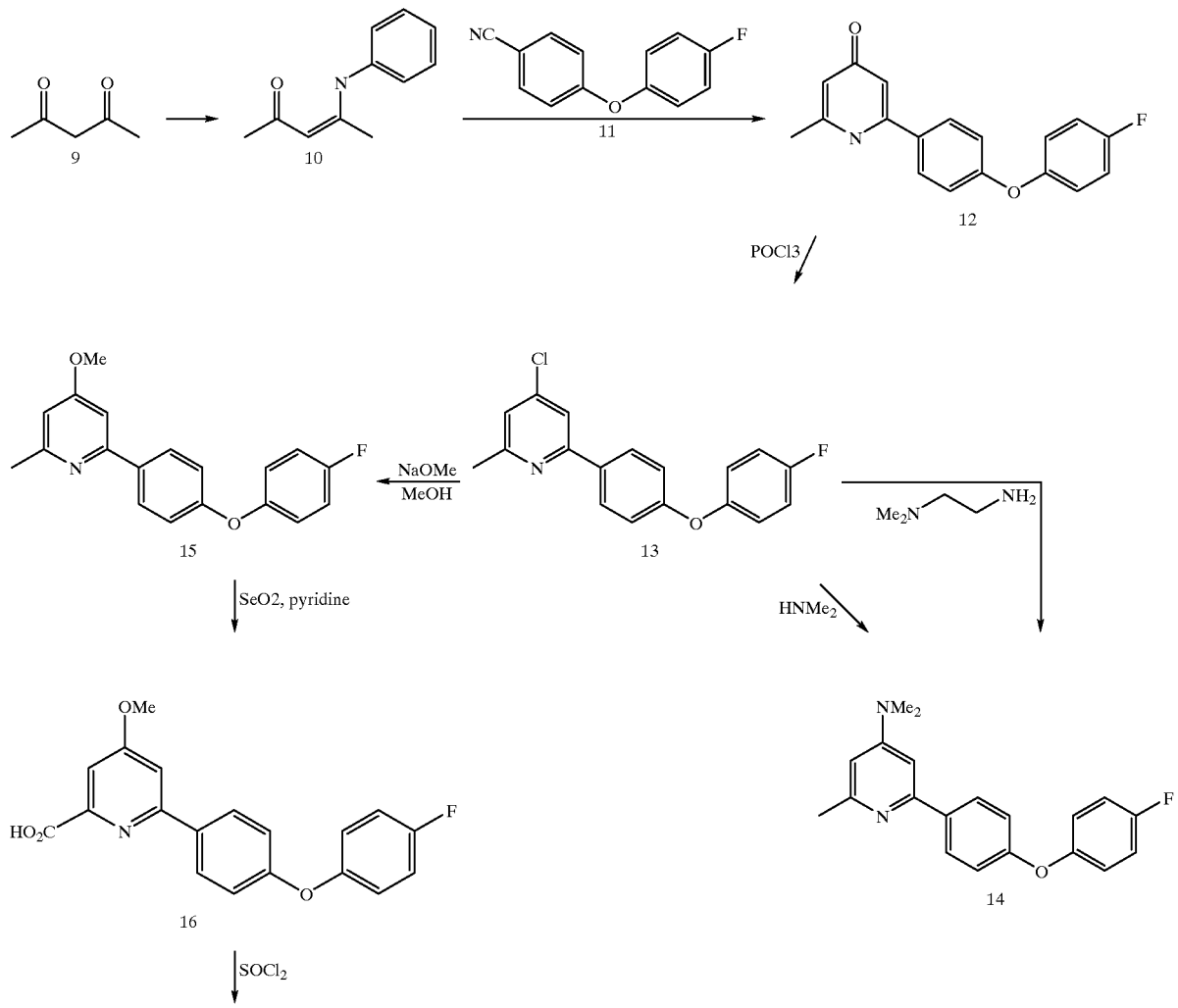

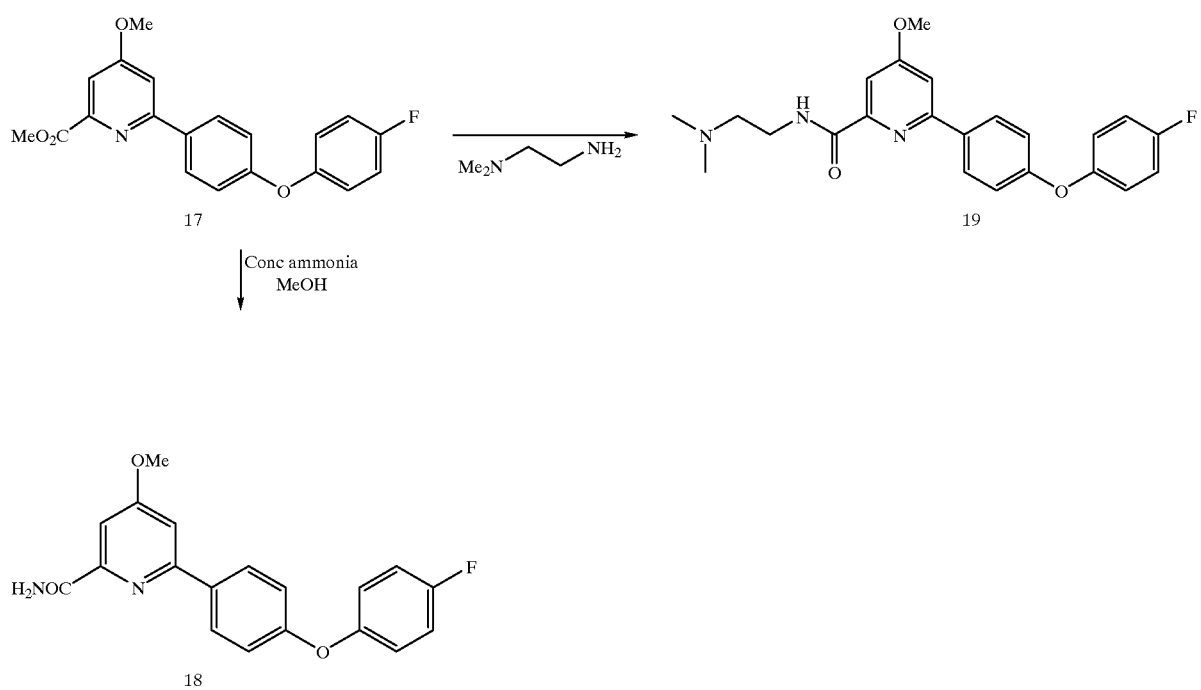

Yields of the above reactions were not optimized. MS spectra for all compounds were obtained with LCMS. The reactions were followed by either TLC or/and LCMS or/and $^1$H NMR.

a) Compound 10: A solution of 10 g (100 mmol) of 2,4-pentadione (9) and 11.2 g (120 mmol) of aniline in 100 mL toluene and catalytical amount of p-toluenesulfonic acid monohydrate was refluxed in a round bottom flask equipped with azotropic apparatus and condenser for 12 hours. The solution was concentrated to dryness and the product was used without purification. $^1$H NMR (CDCl$_3$): δ 7.35 (t, 2H, J=5.69 Hz), 7.19 (t, 1H, J=6.4 Hz), 7.10 (d, 2H, J=7.5 Hz), 5.19 (s, 1H), 2.10 (s, 3H), 1.99 (s,3H).

b) 2-Methyl-6-[4-(4-fluorophenoxy)phenyl]-4-pyridinone (12): 31 mL of 1.6 M n-BuLi (50 mmol) was added dropwise to a solution of 7.21 g (51 mmol) of 2,2,6,6-tetrametylpiperidine in 80 mL THF at −78° C. under inert atomosphere. After the addition, the reaction mixture was stirred for 30 minutes at the same temperature. A solution of 3 g (17 mmol) of compound 10 in 10 mL of THF at −78° C. was added to this solution dropwise. After the addition, the reaction mixture was stirred for 30 minutes. To the resulting dark red solution was added dropwise a solution of 2.7 g (17 mmol) of compound 11 in 13 mL of THF at −78° C. After the addition, the mixture was slowly warmed to −50° C. and stirred at that temperature for one hour. The reaction mixture was poured into cold, saturated aqueous solution of NH$_4$Cl and extracted twice with ethyl acetate. The organic phase was washed with saturated brine, dried with magnesium sulfate, and filtrated. The filtrate was concentrated to dryness. 2-Methyl-6-[4-(4-fluorophenoxy)phenyl]-4-pyridinone was used without purification. $^1$H NMR (CDCl$_3$): δ 7.54 (d, 2H, H=3.8 Hz), 7.31 (m, 2H), 6.90–7.10 (m, 4H), 5.23 (s, 1H), 5.08 (s,1H), 2.03 (s, 3H).

c) 4-Chloro-2-methyl-6-[4-(4-fluorophenoxy)phenyl]pyridine (13): To a flask containing 20 mL of POCl$_3$ at 120° C. oil bath was carefully added a solution of 5 g (17 mmol) of crude compound 12 and 2.6 mL of 1,8-diazabicyclo[5,4,0]undec-7-ene (DBU) (17 mmol) in 20 mL of methylene chloride. After the addition, the reaction mixture was refluxed for one hour. The resulting mixture was concentrated to dryness and diluted with ethyl acetate (EtOAc). Saturated aqueous NaHCO$_3$ was carefully added to the solution to adjust pH to 5–6. The organic phase was separated and the aqueous phase was extracted with the same volume of EtOAc. The combined organic phases were then washed with brine and dried with magnisium sulfate, filtered and concentrated to dryness. The residue was purified with flash chromatography (silica gel, 5% EtOAc/hexane) to get 1.8 g of compound 13 and 850 mg of a mixture of compound 13 and unreacted compound 11. $^1$H NMR (CDCl$_3$): δ 7.93 (d, 2H, J=6.7 Hz), 7.48 (d, 1H, J=1.36 Hz), 7.09 (d, 1H, J=1.5 Hz), 7.00 (m, 6H), 2.59 (s, 3H). MS: 314.1.

d) 2-Methyl-4-dimethylamino-6-[4-(4-fluorophenoxy)phenyl]pyridine (14):

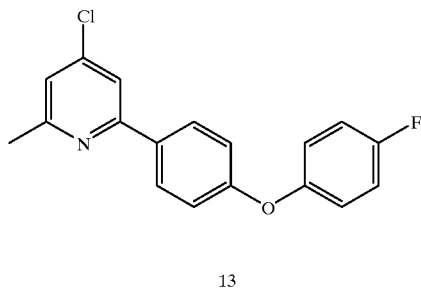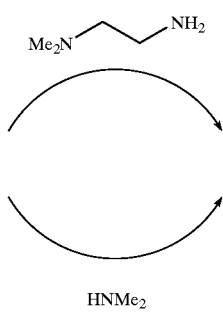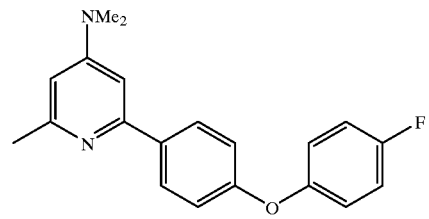

13

HNMe₂

14

15

Method 1: A mixture of 800 mg (2.5 mmol) of compound 13 and 101 mg of 60% NaH (2.5 mmol) in 5 ml N,N-dimethyl ethylendiamine was heated in a sealed tube at 120° C. for six hours. To the cooled reaction mixture was carefully added methanol to quench NaH. The resulting mixture was concentrated to dryness, and the residue was purified by flash chromatography (silica gel, 10% MeOH/CH₂Cl₂ with 1% NH₄OH) to get 100 mg of compound 14.

Method 2: To a 3-neck round bottom flask at −78° C, dimethylamine was condensed and then transferred to a sealed vessel containing compound 13 at −78° C. The sealed vessel was slowly warmed to room temperature and stirred for 48 hours to give a 10% clean conversion. ¹H NMR (CDCl₃): δ 7.89 (d, 2H, J=6.7 Hz), 7.00 (m, 6H), 6.69 (d, 1H, J=2.3 Hz), 6.35 (d, 1H, J=2.3 Hz), 3.03 (s, 6H), 2.51 (s, 3H). MS: 323.2.

e) 2-Methyl-4-methoxy-6-[4-(4-fluorophenoxy)phenyl] pyrimidine (15): A sealed tube containing 1.8 g (4.8 mmol) of compound 13 in 10 ml of 25 wt-% NaOMe in methanol was heated in 85° C. for four hours. The cooled reaction mixture was concentrated to dryness and diluted with ethyl acetate. The mixture was washed with saturated aqueous NH₄Cl and then brine. The organic phase was dried with magnesium sulfate, filtered, and concentrated to dryness to give 1.5 g of clean compound 15. ¹H NMR (CDCl₃): δ 7.92 (d, 2H, J=6.8 Hz), 7.00 (m, 7H), 6.62 (d, 1H, J=2.1 Hz), 3.88 (s, 3H), 2.57 (s, 3H). MS: 310.2.

f) 4-Methoxy-6-[4-(4-fluorophenoxy)phenyl]pyridine-2-carboxylic acid (16): To a solution of 1.5 g (4.8 mmol) of compound 15 in 36 ml of pyridine was added 2.1 g of SeO2 (19 mmol) and the resulting solution was refluxed for 3 days. The cooled reaction mixture was concentrated to dryness and diluted with methanol, filtered, and concentrated to give 100% conversion. ¹H NMR (CDCl₃): δ 7.92 (d, 2H, J=8.8 Hz), 7.69 (s, 1H), 7.38 (m, 3H), 7.07 (m, 4H), 3.97 (s, 3H). MS: 320.9.

g) 4-Methoxy-6-[4-(4-fluorophenoxy)phenyl]pyridine-2-carboxylic acid methyl ester (17): To the methanol solution of the crude compound 16 was slowly added 0.701 ml (9.6 mmol) of thionyl chloride carefully. After the addition, the resulting solution was refluxed for 12 hours. The cooled reaction mixture was filtered, and concentrated to dryness. The residue was then filtered through a plug of silica gel with 10% Et₃N in EtOAc. The filtrate was concentrated to dryness to yield 1.6 g of clean compound 17. ¹H NMR (CDCl₃): δ 7.98 (d, 2H, J=8.7 Hz), 7.61 (d, 1H, J=2.2 Hz), 7.33 (d, 1H, J=2.2 Hz), 7.00 (m, 6H), 4.05 (s, 3H), 4.00 (s, 3H). MS: 354.1.

h) 4-Methoxy-6-[4-(4-fluorophenoxy)phenyl]pyridine-2-carboxamide (18): 140 mg (0.39 mmol) of compound 17 was added to a solution of 10 ml of 2M NH₃ in methanol and the resulting solution was stirred for 12 hours. The mixture was then concentrated to dryness and the resulting solid was recrystalized in methanol to give 67 mg clean 4-methoxy-6-[4-(4-fluorophenoxy)phenyl]pyridine-2-carboxamide (18). ¹H NMR (DMSO-d₆): δ 8.31 (d, 2H, J=8.9 Hz), 8.27 (bs, 1H, N-H), 7.70 (bs, 1H, N-H), 7.61 (d, 1H, J=2.3 Hz), 7.47 (d, 1H, J=2.3 Hz), 7.26 (t, 2H, 8.7 Hz), 7.13 (m, 2H), 7.03 (d, 2H, J=9.0 Hz), 3.94 (s, 3H). MS: 339.2.

i) 4-Methoxy-6-[4-(4-fluorophenoxy)phenyl]pyridine-2-carboxylic acid dimethylaminoethylamide (19): Excess of N,N-dimethyl ethylene diamine was added to the solution of 200 mg (0.56 mmol) of compound 17 in 10 ml methanol, and the resulting solution was stirred at room temperature for 4 days at which time the conversion was complete. The reaction mixture was concentrated to dryness. HCl in Et₂O was added to the residue and the solid was recrystalized to yield clean compound 19. ¹H NMR (CDCl₃): δ 8.97 (bs, 1H, N-H), 8.10 (d, 2H, J=8.8 Hz), 7.61 (d, 1H, J=2.2 Hz), 7.32 (d, 1H, J=2.2 Hz), 7.05 (m, 6H), 4.00 (m, 1H), 3.96 (s, 3H), 3.78 (m, 1H), 3.63 (m, 1H), 3.45 (s, 3H), 3.27 (bs, 1H), 2.85 (s, 3H). MS: 410.2.

EXAMPLE 19

4-[4-(4-Fluorophenoxy)phenyl]-pyrimidine-2-carboxamide as Anticonvulsant

The ability of 4-[4-(4-fluorophenoxy)phenyl]-pyrimidine-2-carboxamide to block maximal electroshock-induced seizures (MES) was determined according to the method above.

4-[4-(4-Fluorophenoxy)phenyl]-pyrimidine-2-carboxamide was administered p.o. to mice 30 minutes before the test procedure. The compound exhibited protection against MES with an $ED_{50}$ (the dose protecting 50% of animals) of 1.6 mg/kg.

The following compounds on Table 1 were tested accordingly after a p.o. administration and also after an i.v. injection. The compounds were injected i.v. 15 minutes before the test procedure.

TABLE 1

Anticonvulsant Evaluation after Oral Administration to Mice and Intravenous Injection into Mice

| Compound name | MES p.o. $ED_{50}$/mg/kg | MES i.v. $ED_{50}$/mg/kg |
|---|---|---|
| 4-[4-(4-fluorophenoxy)phenyl]pyrimidine-2-carboxamide | 1.6 | 0.7 |
| 4-[4-(4-fluorophenoxy)phenyl]pyrimidine-2-carboxylic acid methylamide | 6.1 | 2.8 |
| 4-[4-(4-trifluoromethylphenoxy)phenyl]-pyrimidine-2-carboxamide | 2.5 | 0.5 |
| 2-[4-(4-chloro-2-fluorophenoxy)phenyl]-pyrimidine-4-carboxamide | 5.7 | 2.3 |

TABLE 1-continued

Anticonvulsant Evaluation after Oral Administration
to Mice and Intravenous Injection into Mice

| Compound name | MES p.o. ED$_{50}$/mg/kg | MES i.v. ED$_{50}$/mg/kg |
|---|---|---|
| 4-[4-(2,4-difluorophenoxy)phenyl]-pyrimidine-2-carboxamide | 1.4 | 0.9 |
| 4-[4-(nitrophenoxy)phenyl]pyrimidine-2-carboxamide | 10.0 | 3.1 |
| 4-[4-(4-fluorophenoxy)phenyl]pyrimidine-2-carboxylic acid hydroxymethyleneamide | 5.0 | 1.5 |
| 2-[4-(4-fluorophenoxy)phenyl]pyrimidine-4-carboxamide | 7.5 | 2.5 |
| 6-[4-(4-fluorophenoxy)phenyl]pyridine-2-carboxamide | 3.3 | 1.2 |
| 6-(4-phenoxyphenyl)pyridine-2-carboxamide | 10.5 | 3.2 |
| 2-(4-phenoxyphenyl)-6-(dimethylamino)-pyrimidine-4-carboxylic acid dimethylamide | | 2.10 |
| 2-[4-(4-chloro-2-fluorophenoxy)phenyl]-pyrimidine-4-carboxylic acid dimethylaminomethyleneamide | 4.10 | 1.50 |

EXAMPLE 20

Activity of 4-[4-(4-Fluorophenoxy)phenyl]-pyrimidine-2-carboxamide as Sodium Channel Blocker 4-[4-(4-Fluorophenoxy)phenyl]-pyrimidine-2-carboxamide was tested in the electrophysiological assay 1 and binding assay as described above and produced dose-dependent inhibition of voltage-gated sodium currents recorded in HEK-293 cells stably expressing the rBIIA isoform of Na$^+$ channels. The blocking effect of this compound on Na$^+$ currents was highly sensitive to the holding voltage, indicating that 4-[4-(4-fluorophenoxy)phenyl]-pyrimidine-2-carboxamide binds to voltage-sensitive Na$^+$ channels in their inactivated states and has weak potency towards Na$^+$ channels in their resting states (Ragsdale et al., *Mol. Pharmacol.* 40:756–765 (1991); Kuo and Bean, *Mol. Pharmacol.* 46:716–725 (1994)). The apparent antagonist dissociation constant (K$_i$) of this compound for inactivated sodium channels is 0.49 µM.

The K$_i$ (the concentration of a compound that produces half maximal inhibition) value for 4-[4-(4-fluorophenoxy)phenyl]-pyrimidine-2-carboxamide and other tested compounds are presented in Table 2.

TABLE 2

Evaluation of the Tested Compounds as Sodium Channel
Blockers after an Electrophysiological in vitro Assay 1

| Compound name | RBIIA K$_i$/µM |
|---|---|
| 4-[4-(4-fluorophenoxy)phenyl]pyrimidine-2-carboxamide | 0.49 |
| 4-[4-(4-fluorophenoxy)phenyl]pyrimidine-2-carboxylic acid dimethylamide | 13.50 |
| 4-[4-(4-fluorophenoxy)phenyl]pyrimidine-2-carboxylic acid tert-butylamide | 0.18 |
| 4-[4-(4-trifluoromethylphenoxy)phenyl]pyrimidine-2-carboxamide | 0.21 |
| 2-[4-(4-chloro-2-fluorophenoxy)phenyl]pyrimidine-4-carboxamide | 0.22 |
| 4-[4-(4-fluorophenoxy)phenyl]pyrimidine-2-carboxylic acid | 51 |
| 4-[4-(2,4-difluorophenoxy)phenyl]-pyrimidine-2-carboxamide | 0.36 |
| 2-[4-(4-fluorophenoxy)phenyl]pyrimidine-4-carboxamide | 0.10 |

TABLE 2-continued

Evaluation of the Tested Compounds as Sodium Channel
Blockers after an Electrophysiological in vitro Assay 1

| Compound name | RBIIA K$_i$/µM |
|---|---|
| 6-[4-(4-fluorophenoxy)phenyl]pyridine-2-carboxamide | 0.07 |
| 2-[4-(4-fluorophenoxy)phenyl]-4-[3-(1,2,4-triazolyl)]pyrimidine | 20.00 |
| 3,5-diamino-6-(4-phenoxyphenyl)pyrazine-2-carboxamide | 2.20 |

EXAMPLE 21

Activity of 6-[4-(4-fluorophenoxy)phenyl]pyridine carboxylic acid N-piperidinylethylamide as Sodium Channel Blocker 6-[4-(4-fluorophenoxy)phenyl]pyridine carboxylic acid N-piperidinylethylamide was tested in the electrophysiological assay 2 as described above. The result of 6-[4-(4-fluorophenoxy)phenyl]pyridine carboxylic acid N-piperidinylethylamide and other compounds are represented in Table 3.

TABLE 3

Evaluation of the Tested Compounds as Sodium Channel
Blockers after an Electrophysiological in vitro Assay 2

| Compound name | RBIIA/β1 K$_i$/µM |
|---|---|
| 6-[4-(4-fluorophenoxy)phenyl]pyridine carboxylic acid N-piperidinylethylamide (3) | 0.06 |
| 6-(4-tert-butylphenyl)pyridine-2-carboxamide (8a) | 6.13 |
| 6-(4-n-butylphenyl)pyridine-2-carboxamide (8b) | 10.53 |
| 6-(4-i-propylphenyl)pyridine-2-carboxamide (8c) | 41.61 |
| 6-(4-thiomethylphenyl)pyridine-2-carboxamide (8d) | 52.73 |
| 6-(4-ethoxyphenyl)pyridine-2-carboxamide (8e) | 58.72 |
| 6-(4-methoxyphenyl)pyridine-2-carboxamide (8f) | 23.87 |
| 2-methyl-4-dimethylamino-6-[4-(4-fluorophenoxy)phenyl]pyridine (14) | 0.33 |
| 4-methoxy-6-[4-(4-fluorophenoxy)phenyl]pyridine-2-carboxamide (18) | 3.43 |
| 4-methoxy-6-[4-(4-fluorophenoxy)phenyl]pyridine-2-carboxylic acid dimethylaminoethylamide (19) | 0.32 |
| 2-dimethylamino-4-[4-(4-fluorophenoxy)phenyl]pyrimidine | 27.57 |
| 4-[4-(4-fluorophenoxy)phenyl]pyrimidine-2-carboxylic acid ethyl ester | 9.86 |
| 4-[4-(4-fluorophenoxy)phenyl]pyrimidine-2-carbamate | 8.70 |
| 4-[4-(4-fluorophenoxy)phenyl]pyrimidine-2-carboxylic acid 2-chloroethylamide | 2.62 |
| 1-[4-[4-(4-fluorophenoxy)phenyl]pyrimidine-2-yl]-2,2-dibromoethanone | 10.63 |
| 4-[4-(4-fluorophenoxy)phenyl]pyrimidine-2-carboxylic acid methylaminomethyleneamide hydrochloride | 11.36 |
| 2-[3-(1,2,4-triazolyl)]-4-[4-(4-fluorophenoxy)phenyl]pyrimidine | 5.91 |
| 4-[4-(2,4-difluorophenoxy)phenyl]pyrimidine-2-carboxylic acid methyl ester | 139 |
| 2-[4-(4-fluorophenoxy)phenyl]pyrimidine-4-carboxylic acid methyl ester | 71.53 |
| 6-[4-(4-fluorophenoxy)phenyl]pyridine-2,3-dicarboxamide | 4.54 |
| 2-methyl-6-[4-(4-fluorophenoxy)phenyl]pyridine-3-carboxamide | 8.45 |
| 5-cyano-6-(4-phenoxyphenyl)pyridine-2-carboxamide | 11.9 |
| 5-hydroxy-6-(4-phenoxyphenyl)pyridine-2-carboxamide | 99.3 |
| 2-(5-isoxazolyl)-4-[4-(4-fluorophenoxy)phenyl]pyrimidine | 2.63 |
| 4-[4-(4-fluorophenoxy)phenyl]pyrimidine-2-carboxylic acid hydroxymethyleneamide | 3.53 |
| 4-[4-(4-nitrophenoxy)phenyl]pyrimidine-2-carboxamide | 1.13 |

EXAMPLE 22

Activity of 6-[4-(4-fluorophenoxy)phenyl]pyridine carboxylic acid N-piperidinylethylamide as Sodium Channel Blocker The tactile antiallodynia effect of the compounds listed in Table 4 was tested in the Chung model of neuropathic pain in rats as described above and described by Kim and Chung (*Pain* 50:355–363 (1992)). The tested compounds showed activity in the Chung model. The results for each tested compound are shown as minimal effective dose (MED) in Table 4.

TABLE 4

Evaluation of the Tested Compounds in Chung Model of Neuropathic Pain in Rats

| Compound name | MED Mg/kg p.o. |
| --- | --- |
| 2-[4-(4-chloro-2-fluorophenoxy)phenyl]pyrimidine-4-carboxamide | 1.25 |
| 2-[4-(4-fluorophenoxy)phenyl]pyrimidine-4-carboxamide | 2.50 |
| 6-[4-(4-fluorophenoxy)phenyl]pyridine-2-carboxamide | 2.50 |

Having now fully described this invention, it will be understood by those of ordinary skill in the art that the same can be performed within a wide and equivalent range of conditions, formulations and other parameters without affecting the scope of the invention or any embodiment thereof.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

All patents and publications cited herein are fully incorporated by reference herein in their entirety.

What is claimed is:

1. A compound having the Formula I:

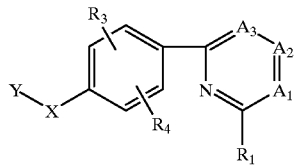

or a pharmaceutically acceptable salt or solvate thereof, wherein:

Y is

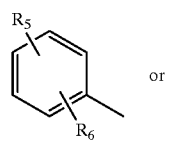

or $R_7$, provided that when Y is $R_7$, $R_1$ is —C(O)NH$_2$;

$A_1$ is N and $A_2$ and $A_3$ are CR$_2$, or $A_3$ is N and $A_1$ and $A_2$ are CR$_2$;

$R_1$ is selected from the group consisting an optionally substituted alkyl, amino, alkylthio, C(O)R$_8$, SO$_2$R$_8$, OC(O)NH$_2$, 2-imidazolinyl, 2-imidazolyl, 3-pyrazolyl, 5-isoxazolyl, and 3-(1,2,4)-triazolyl;

each $R_2$ is selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino; or $R_1$ and $R_2$ are taken together with the carbon atoms to which they are attached to form a heterocyclic ring;

$R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, and alkylthiol;

$R_7$ is an optionally substituted alkyl;

$R_8$ is selected from the group consisting of alkyl, alkenyl, alkynyl, OR$_9$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted, provided that $R_8$ is not OR$_9$ when $R_1$ is SO$_2$R$_8$; wherein $R_9$ is selected from the group consisting of hydrogen, optionally substituted alkyl, and an alkali metal; and X is one of O, S, NH, or CH$_2$ when Y is other than $R_7$; or X is one of O, S, NH, CH$_2$ or absent when Y is $R_7$;

with the provisos that $R_2$ is not methoxy if $R_5$ is trifluoromethyl, $R_6$ is H, X is O and $R_1$ is SO$_2$CH$_2$Ph; or each $R_2$ is hydrogen when $R_1$ is carboxy, X is O, $A_1$ is N, and Y is

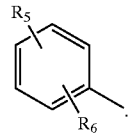

2. A compound having the Formula II:

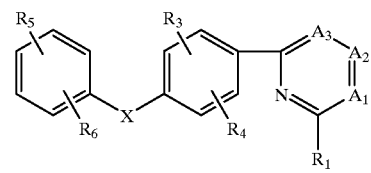

or a pharmaceutically acceptable salt or solvate thereof, wherein:

$A_1$ is N and $A_2$ and $A_3$ are CR$_2$, or $A_3$ is N and $A_1$ and $A_2$ are CR$_2$;

$R_1$ is selected from the group consisting an optionally substituted alkyl, amino, alkylthio, C(O)R$_8$, SO$_2$R$_8$, OC(O)NH$_2$, 2-imidazolinyl, 2-imidazolyl, 3-pyrazolyl, 5-isoxazolyl, and 3-(1,2,4)-triazolyl;

each $R_2$ is selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino; or $R_1$ and $R_2$ are taken together with the carbon atoms to which they are attached to form a heterocyclic ring;

$R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, and alkylthiol; and $R_8$ is selected from the group consisting of alkyl, alkenyl, alkynyl, $OR_9$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted, provided that $R_8$ is not $OR_9$ when $R_1$ is $SO_2R_8$; wherein $R_9$ is selected from the group consisting of hydrogen, optionally substituted alkyl, and an alkali metal; and X is one of O, S, NH, or $CH_2$;

with the provisos that $R_2$ is not methoxy if $R_5$ is trifluoromethyl, $R_6$ is H, X is O and $R_1$ is $SO_2CH_2Ph$; or each $R_2$ is hydrogen when $R_1$ is carboxy, X is O, and $A_1$ is N.

3. The compound of claim 2, wherein $A_3$ is N and $A_1$ and $A_2$ are $CR_2$.

4. The compound of claim 2, wherein $R_1$ is selected from the group consisting of an alkyl optionally substituted by halogen or hydroxy, $C(O)R_8$, $SO_2R_8$, 2-imidazolinyl, 2-imidazolyl, 3-pyrazolyl, and 5-isoxazolyl, wherein $R_8$ is as defined in claim 2, provided that $R_8$ is not $OR_9$ when $R_1$ is $SO_2R_8$.

5. The compound of claim 4, wherein $R_8$ is selected from the group consisting of alkyl, alkenyl, $OR_9$, amino, alkylamino, dialkylamino, alkenylamino, dialkylaminoalkenyl, dialkylaminoalkylamino, and heterocycloalkylamino, all of which can be optionally substituted, and wherein $R_9$ is as defined in claim 2.

6. The compound of claim 2, wherein $R_2$ is selected from the group consisting of hydrogen, alkyl, alkenyl, alkynyl, aminoalkyl, amino, hydroxyalkyl, alkoxy, aminocarbonyl, alkylaminocarbonyl, arylaminocarbonyl, aralkylaminocarbonyl, alkylcarbonylamino, arylcarbonylamino, and aralkylcarbonylamino.

7. The compound of claim 6, wherein $R_2$ is selected from the group consisting of hydrogen, alkyl, alkoxy, aminoalkyl and aminocarbonyl.

8. The compound of claim 2, wherein $R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, and cyano.

9. The compound of claim 8, wherein $R_3$ and $R_4$ are both hydrogen and $R_5$ and $R_6$ are independently selected from the group consisting of hydrogen, alkyl, halogen, haloalkyl, and nitro.

10. The compound of claim 2, wherein X is O or S.

11. The compound of claim 10, wherein X is O.

12. The compound of claim 2, wherein $R_2$ is hydrogen, X is O or S and $R_1$ is aminocarbonyl.

13. The compound of claim 2, wherein $A_1$ is N, $A_2$ is $CR_2$, wherein $R_2$ is other than H and $A_3$ is CH.

14. The compound of claim 2, wherein $A_3$ is N, $A_2$ is $CR_2$, wherein $R_2$ is other than H and $A_1$ is CH.

15. The compound of claim 2, having the Formula III:

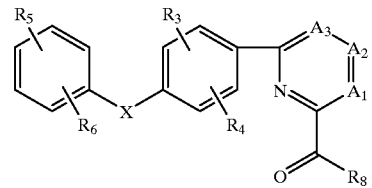

or a pharmaceutically acceptable salt or solvate thereof, wherein;

$A_1$–$A_3$, $R_2$–$R_6$, $R_8$ and X are as defined in claim 2.

16. The compound of claim 15, wherein $A_3$ is N and $A_1$ and $A_2$ are $CR_2$.

17. The compound of claim 15, wherein $R_2$ is selected from the group consisting of hydrogen, alkyl, alkenyl, alkynyl, aminoalkyl, amino, hydroxyalkyl, alkoxy, aminocarbonyl, alkylaminocarbonyl, arylaminocarbonyl, aralkylaminocarbonyl, alkylcarbonylamino, arylcarbonylamino, and aralkylcarbonylamino.

18. The compound of claim 17, wherein $R_2$ is selected from the group consisting of hydrogen, alkyl, alkoxy, aminoalkyl and aminocarbonyl.

19. The compound of claim 15, wherein $R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, and cyano.

20. The compound of claim 19, wherein $R_3$ and $R_4$ are both hydrogen and $R_5$ and $R_6$ are independently selected from the group consisting of hydrogen, alkyl, halogen, haloalkyl, and nitro.

21. The compound of claim 15, wherein $R_8$ is selected from the group consisting of alkyl, alkenyl, $OR_9$, amino, alkylamino, dialkylamino, alkenylamino, dialkylaminoalkenyl, dialkylaminoalkylamino, and heterocycloalkylamino, all of which can be optionally substituted, provided that $R_8$ is not $OR_9$ when $R_1$ is $SO_2R_8$.

22. The compound of claim 15, wherein X is O or S.

23. The compound of claim 22, wherein X is O.

24. The compound of claim 15, wherein

X is O;

$A_1$ is N and $A_2$ and $A_3$ are $CR_2$; or $A_3$ is N and $A_1$ and $A_2$ are $CR_2$; wherein $R_2$ is selected from the group consisting of hydrogen, alkyl, alkoxy, aminoalkyl, and aminocarbonyl;

$R_3$ and $R_4$ are both hydrogen;

$R_5$ and $R_6$ are independently selected from the group consisting of hydrogen, alkyl, halogen, haloalkyl, and nitro; and $R_8$ is amino.

25. The compound of claim 15, wherein $A_1$ is N, $A_2$ is $CR_2$, wherein $R_2$ is other than H and $A_3$ is CH.

26. The compound of claim 15, wherein $A_3$ is N, $A_2$ is $CR_2$, wherein $R_2$ is other than H and $A_1$ is CH.

27. The compound of claim 2, having Formula IV:

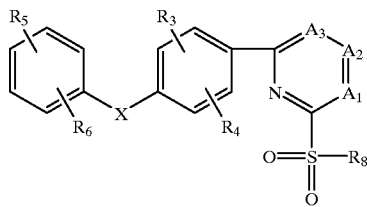

or a pharmaceutically acceptable salt or solvate thereof; wherein:

$A_1$–$A_3$, $R_2$–$R_6$, and X are as defined in claim 2 and $R_8$ is selected from the group consisting of alkyl, alkenyl, alkynyl, amino, alkylamino, dialkylamino, alkenylamino, dialkylaminoalkenyl, dialkylaminoalkylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted.

28. The compound of claim 27, wherein $R_2$ is selected from the group consisting of hydrogen, alkyl, alkenyl, alkynyl, aminoalkyl, amino, hydroxyalkyl, alkoxy, aminocarbonyl, alkylaminocarbonyl, arylaminocarbonyl, aralkylaminocarbonyl, alkylcarbonylamino, arylcarbonylamino, and aralkylcarbonylamino.

29. The compound of claim 28, wherein $R_2$ is selected from the group consisting of hydrogen, alkyl, alkoxy, aminoalkyl and aminocarbonyl.

30. The compound of claim 27, wherein $R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, and cyano.

31. The compound of claim 30, wherein $R_3$ and $R_4$ are both hydrogen and $R_5$ and $R_6$ are independently selected from the group consisting of hydrogen, alkyl, halogen, haloalkyl, and nitro.

32. The compound of claim 27, wherein $R_8$ is selected from the group consisting of alkyl, alkenyl, amino, alkylamino, dialkylamino, alkenylamino, dialkylaminoalkenyl, and heterocycloalkylamino, all of which can be optionally substituted.

33. The compound of claim 27, wherein X is O or S.
34. The compound of claim 33, wherein X is O.
35. A compound, wherein said compound is:
4-[4-(4-fluorophenoxy)phenyl]pyrimidine-2-carboxamide;
4-[4-(4-nitrophenoxy)phenyl]pyrimidine-2-carboxamide;
4-[4-(4-methoxyphenoxy)phenyl]pyrimidine-2-carboxamide;
4-[4-(4-trifluoromethylphenoxy)phenyl]pyrimidine-2-carboxamide;
4-[4-(3-chloro-2-cyanophenoxy)phenyl]pyrimidine-2-carboxamide;
4-[4-(4-chloro-2-fluorophenoxy)phenyl]pyrimidine-2-carboxamide;
4-[4-(2,4-difluorophenoxy)phenyl]pyrimidine-2-carboxamide;
4-[4-(2-chloro-4-fluorophenoxy)phenyl]pyrimidine-2-carboxamide;
1-[4-[4-(4-fluorophenoxy)phenyl]pyrimidine-2-yl]-ethanone;
2-[4-(4-fluorophenoxy)phenyl]pyrimidine-4-carboxamide;
2-[4-(4-fluorophenoxy)phenyl]-4-methylpyrimidine;
2-methyl-4-[4-(4-fluorophenoxy)phenyl]pyrimidine;
4-[4-(4-fluorophenoxy)phenyl]pyrimidine-2-carboxylic acid;
4-[4-(4-fluorophenoxy)phenyl]pyrimidine-2-carboxylic acid sodium salt;
4-[4-(4-fluorophenoxy)phenyl]pyrimidine-2-carboxylic acid methylamide;
4-[4-(4-fluorophenoxy)phenyl]pyrimidine-2-carboxylic acid dimethylamide;
4-[4-(4-fluorophenoxy)phenyl]pyrimidine-2-carboxylic acid tert-butylamide;
2-[4-(4-chloro-2-fluorophenoxy)phenyl]pyrimidine-4-carboxamide;
2-[4-(4-chloro-2-fluorophenoxy)phenyl]pyrimidine-4-carboxylic acid;
2-(4-phenoxyphenyl)-6-(dimethylamino)pyrimidine-4-carboxylic acid dimethylamide;
4-[4-(4-fluorophenoxy)phenyl]pyrimidine-2-carboxylic acid 2-hydroxyethylamide;
4-[4-(4-fluorophenoxy)phenyl]pyrimidine-2-carboxylic acid hydroxymethyleneamide;
2-(2-hydroxyprop-2-yl)-4-[4-(4-fluorophenoxy)phenyl]pyrimidine;
4-[4-(2,4-difluorophenoxy)phenyl]pyrimidine-2-carboxylic acid 2-morpholin-4-yl-ethyl amide;
2-(4,5-dihydro-1H-imidazol-2-yl)-4-[4-(4-fluorophenoxy)phenyl]-pyrimidine;
2-(3-pyrazolyl)-4-[4-(4-fluorophenoxy)phenyl]pyrimidine;
2-(5-isoxazolyl)-4-[4-(4-fluorophenoxy)phenyl]pyrimidine;
2-(1-methyl-3-pyrazolyl)-4-[4-(4-fluorophenoxy)phenyl]pyrimidine;
2-[4-(4-chloro-2-fluorophenoxy)phenyl]pyrimidine-4-carboxylic acid methylamide;
3-dimethylamino-1-{4-[4-(4-fluorophenoxy)phenyl}pyrimidin-2-yl]propenone;
2-thiomethyl-4-[4-(4-fluorophenoxy)phenyl]pyrimidine;
2-methanesulfonyl-4-[4-(4-fluorophenoxy)phenyl]pyrimidine;
2-[4-(4-chloro-2-fluorophenoxy)phenyl]-4-methyl-pyrimidine;
4-[4-(4-fluorophenoxy)-3-fluorophenyl]pyrimidine-2-carboxamide; or
2-[4-(4-fluorophenoxy)-3-fluorophenyl]pyrimidine-4-carboxamide;
or a pharmaceutically acceptable salt, prodrug or solvate thereof.

36. The compound of claim 1, having the Formula V:

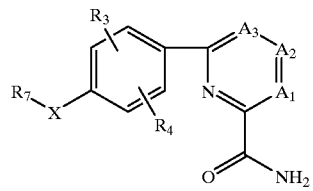

or a pharmaceutically acceptable salt or solvate thereof, wherein;

$A_1$–$A_3$, $R_2$–$R_4$, and $R_7$ are as defined in claim 1; and X is one of O, S, NH, $CH_2$ or absent.

37. The compound of claim 36, wherein $A_3$ is N and $A_1$ and $A_2$ are $CR_2$.

38. The compound of claim 36, wherein $R_7$ is a $C_{1-6}$ alkyl optionally substituted with one or more of halogen, hydroxy, nitro, amino, cyano and alkoxy.

39. The compound of claim 36, wherein $R_2$ is selected from the group consisting of hydrogen, alkyl, alkoxy, aminoalkyl and aminocarbonyl.

40. The compound of claim 36, wherein $R_3$ and $R_4$ are independently selected from the group consisting of hydrogen, alkyl, alkenyl, alkynyl, halogen, haloalkyl, hydroxyalkyl, hydroxy, nitro, amino, and cyano.

41. The compound of claim 40, wherein $R_3$ and $R_4$ are both hydrogen.

42. The compound of claim 36, wherein X is O or S.

43. The compound of claim 42, wherein x is O.

44. A pharmaceutical composition, comprising the compound of formula:

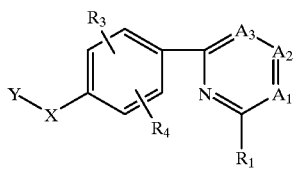

or a pharmaceutically acceptable salt or solvate thereof, wherein:

Y is

[structure with $R_5$, $R_6$] or $R_7$, provided that when Y is $R_7$, $R_1$ is —C(O)NH$_2$;

$A_1$ is N and $A_2$ and $A_3$ are $CR_2$; or $A_3$ is N and $A_1$ and $A_2$ are $CR_2$;

$R_1$ is selected from the group consisting an optionally substituted alkyl, amino, alkylthio, C(O)R$_8$, SO$_2$R$_8$, OC(O)N$_2$, 2-imidazolinyl, 2-imidazolyl, 3-pyrazolyl, 5-isoxazolyl, and 3-(1,2,4)-triazolyl;

each $R_2$ is selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino; or $R_1$ and $R_2$ are taken together with the carbon atoms to which they are attached to form a heterocyclic ring;

$R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, and alkylthiol;

$R_7$ is an optionally substituted alkyl;

$R_8$ is selected from the group consisting of alkyl, alkenyl, alkynyl, OR$_9$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted, provided that R$_8$ is not OR$_9$ when R$_1$ is SO$_2$R$_8$; wherein $R_9$ is selected from the group consisting of hydrogen, optionally substituted alkyl, and an alkali metal; and X is one of O, S, NH, or CH$_2$ when Y is other than R$_7$; or X is one of O, S, NH, CH$_2$ or absent when Y is R$_7$;

with the proviso that each $R_2$ is hydrogen when $R_1$ is carboxy, X is O, $A_1$ is N, and Y is

[structure with $R_5$, $R_6$];

and a pharmaceutically acceptable carrier or diluent.

45. A compound, wherein said compound is 2-[4-(4-chloro-2-fluorophenoxy)phenyl]pyrimidine-4-carboxamide or a pharmaceutically acceptable salt, prodrug or solvate thereof.

46. The compound of claim 45, which is 2-[4-(4-chloro-2-fluorophenoxy)phenyl]pyrimidine-4-carboxamide.

47. A pharmaceutical composition, comprising the compound of claim 45 or claim 46 and a pharmaceutically acceptable carrier or diluent.

48. A compound having the Formula I:

[structure]

or a pharmaceutically acceptable salt or solvate thereof, wherein:

Y is

[structure with $R_5$, $R_6$] or $R_7$, provided that when Y is $R_7$, $R_1$ is —C(O)NH$_2$;

$A_1$ is N and $A_2$ and $A_3$ are $CR_2$; or $A_3$ is N and $A_1$ and $A_2$ are $CR_2$;

$R_1$ is selected from the group consisting an optionally substituted alkyl, amino, alkylthio, C(O)R$_8$, SO$_2$R$_8$, OC(O)NH$_2$, 2-imidazolinyl, 2-imidazolyl, 3-pyrazolyl, 5-isoxazolyl, and 3-(1,2,4)-triazolyl;

each $R_2$ is selected from the group consisting of hydrogen, optionally substituted alkyl, alkenyl, or alkynyl, halogen, hydroxy, cycloalkyl, cyano, alkylamino, dialkylamino, alkoxy, aminocarbonyl, alkylaminocarbonyl, arylaminocarbonyl, aralkylaminocarbonyl, and aralkylcarbonylamino; or $R_1$ and $R_2$ are taken together with the carbon atoms to which they are attached to form a heterocyclic ring;

$R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, and alkylthiol;

$R_7$ is an optionally substituted alkyl;

$R_8$ is selected from the group consisting of alkyl, alkenyl, alkynyl, $OR_9$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted, provided that $R_8$ is not $OR_9$ when $R_1$ is $SO_2R_8$; wherein $R_9$ is selected from the group consisting of hydrogen, optionally substituted alkyl, and an alkali metal; and X is one of O, S, NH, or $CH_2$ when Y is other than $R_7$; or X is one of O, S, NH, $CH_2$ or absent when Y is $R_7$;

with the proviso that $R_2$ is not methoxy if $R_5$ is trifluoromethyl, $R_6$ is H, X is O and $R_1$ is $SO_2CH_2Ph$.

49. The compound of claim 2, wherein $A_1$ is N and $A_2$ and $A_3$ are $CR_2$.

50. The compound of claim 15, wherein $A_1$ is N and $A_2$ and $A_3$ are $CR_2$.

51. The compound of claim 36, wherein $A_1$ is N and $A_2$ and $A_3$ are $CR_2$.

52. A pharmaceutical composition, comprising the compound of formula:

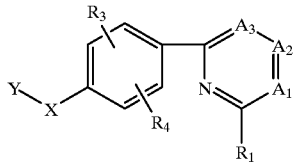

or a pharmaceutically acceptable salt or solvate thereof, wherein:

Y is

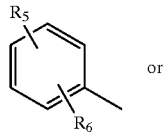

$R_7$, provided that when Y is $R_7$, $R_1$ is —C(O)NH$_2$;

$A_1$ is N and $A_2$ and $A_3$ are $CR_2$; or $A_3$ is N and $A_1$ and $A_2$ are $CR_2$;

$R_1$ is selected from the group consisting an optionally substituted alkyl, amino, alkylthio, C(O)$R_8$, SO$_2$R$_8$, OC(O)NH$_2$, 2-imidazolinyl, 2-imidazolyl, 3-pyrazolyl, 5-isoxazolyl, and 3-(1,2,4)-triazolyl;

each $R_2$ is selected from the group consisting of hydrogen, optionally substituted alkyl, alkenyl, or alkynyl, halogen, hydroxy, cycloalkyl, cyano, alkylamino, dialkylamino, alkoxy, aminocarbonyl, alkylaminocarbonyl, arylaminocarbonyl, aralkylaminocarbonyl, and aralkylcarbonylamino; or $R_1$ and $R_2$ are taken together with the carbon atoms to which they are attached to form a heterocyclic ring;

$R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, and alkylthiol;

$R_7$ is an optionally substituted alkyl;

$R_8$ is selected from the group consisting of alkyl, alkenyl, alkynyl, $OR_9$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted, provided that $R_8$ is not $OR_9$ when $R_1$ is $SO_2R_8$; wherein $R_9$ is selected from the group consisting of hydrogen, optionally substituted alkyl, and an alkali metal; and X is one of O, S, NH, or $CH_2$ when Y is other than $R_7$; or X is one of O, S, NH, $CH_2$ or absent when Y is $R_7$; and a pharmaceutically acceptable carrier or diluent.

53. A compound having the Formula I:

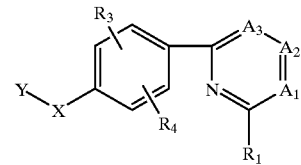

or a pharmaceutically acceptable salt or solvate thereof, wherein:

Y is

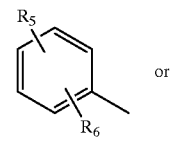

$R_7$, provided that when Y is $R_7$, $R_1$ is —C(O)NH$_2$;

$A_1$ is N and $A_2$ and $A_3$ are $CR_2$, or $A_3$ is N and $A_1$ and $A_2$ are $CR_2$;

$R_1$ is selected from the group consisting an optionally substituted alkyl, amino, alkylthio, C(O)$R_8$, SO$_2$R$_8$, OC(O)NR$_2$, 2-imidazolinyl, 2-imidazolyl, 3-pyrazolyl, 5-isoxazolyl, and 3-(1,2,4)-triazolyl;

each $R_2$ is selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino; or $R_1$ and $R_2$ are taken together with the carbon atoms to which they are attached to form a heterocyclic ring;

$R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, and alkylthiol;

$R_7$ is an optionally substituted alkyl;

$R_8$ is selected from the group consisting of alkyl, alkenyl, alkynyl, $OR_9$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted, provided that $R_8$ is not $OR_9$ when $R_1$ is $SO_2R_8$; wherein $R_9$ is selected from the group consisting of hydrogen, optionally substituted alkyl, and an alkali metal; and X is one of S, NH, or $CH_2$ when Y is other than $R_7$; or X is one of O, S, NH, $CH_2$ or absent when Y is $R_7$.

54. The compound of claim 2 having the Formula II:

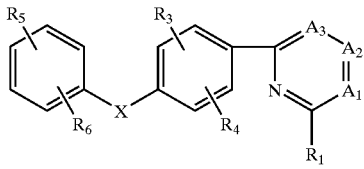

or a pharmaceutically acceptable salt or solvate thereof, wherein:

$A_1$ is N and $A_2$ and $A_3$ are $CR_2$;

$R_1$ is selected from the group consisting an optionally substituted alkyl, amino, alkylthio, $C(O)R_8$, $SO_2R_8$, $OC(O)NH_2$, 2-imidazolinyl, 2-imidazolyl, 3-pyrazolyl, 5-isoxazolyl, and 3-(1,2,4)-triazolyl;

each $R_2$ is selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino; or $R_1$ and $R_2$ are taken together with the carbon atoms to which they are attached to form a heterocyclic ring;

$R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, and alkylthiol; and $R_8$ is selected from the group consisting of alkyl, alkenyl, alkynyl, $OR_9$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted, provided that $R_8$ is not $OR_9$ when $R_1$ is $SO_2R_8$; wherein $R_9$ is selected from the group consisting of optionally substituted alkyl and an alkali metal; and X is one of O, S, NH, or $CH_2$;

with the proviso that $R_2$ is not methoxy if $R_5$ is trifluoromethyl, $R_6$ is H, X is O and $R_1$ is $SO_2CH_2Ph$.

55. The compound of claim 2 having the Formula II:

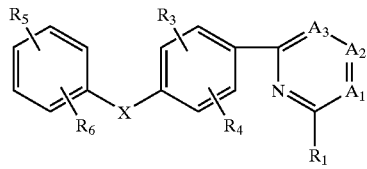

or a pharmaceutically acceptable salt or solvate thereof, wherein:

$A_3$ is N and $A_1$ and $A_2$ are $CR_2$;

$R_1$ is selected from the group consisting an optionally substituted alkyl, amino, alkylthio, $C(O)R_8$, $SO_2R_8$, $OC(O)NH_2$, 2-imidazolinyl, 2-imidazolyl, 3-pyrazolyl, 5-isoxazolyl, and 3-(1,2,4)-triazolyl;

each $R_2$ is selected from the group consisting of hydrogen, optionally substituted alkyl, alkenyl, or alkynyl, halogen, hydroxy, cycloalkyl, cyano, amino, alkylamino, dialkylamino, alkoxy, aminocarbonyl, alkylaminocarbonyl, arylaminocarbonyl, aralkylaminocarbonyl, alkylcarbonylamino, arylcarbonylamino, and aralkylcarbonylamino; or $R_1$ and $R_2$ are taken together with the carbon atoms to which they are attached to form a heterocyclic ring;

$R_3$, $R_4$, $R_5$, and $R_6$ are independently selected from the group consisting of hydrogen, alkyl, alkenyl, alkynyl, halogen, haloalkyl, hydroxyalkyl, hydroxy, nitro, amino, cyano, amide, carboxyalkyl, alkoxyalkyl, ureido, acylamino, thiol, acyloxy, azido, alkoxy, carboxy, and alkylthiol; and $R_8$ is selected from the group consisting of alkyl, alkenyl, alkynyl, $OR_9$, amino, alkylamino, dialkylamino, alkenylamino, dialkylaminoalkenyl, dialkylaminoalkylamino, dialkylaminoalkenylamino, alkylaminoalkenyl-amino, hydroxyaminoalkenylamino, cycloalkyl, heterocycloalkyl, cycloalkylalkylamino, heterocycloalkylamino, aryl, arylalkyl, arylalkenyl, arylalkynyl, and arylalkylamino, all of which can be optionally substituted, provided that $R_8$ is not $OR_9$ when $R_1$ is $SO_2R_8$; wherein $R_9$ is selected from the group consisting of hydrogen, optionally substituted alkyl, and an alkali metal; and X is one of O, S, NH, or $CH_2$;

with the proviso that $R_2$ is not methoxy if $R_5$ is trifluoromethyl, $R_6$ is H, X is O and $R_1$ is $SO_2CH_2Ph$.

56. A pharmaceutical composition, comprising the compound of claim 35 and a pharmaceutically acceptable carrier or diluent.

57. The composition of claim 44, wherein the compound is as claimed in any one of claims 1, 2, 48, 53, 54, or 55.

* * * * *